US012268830B2

(12) United States Patent
Fell et al.

(10) Patent No.: US 12,268,830 B2
(45) Date of Patent: Apr. 8, 2025

(54) SURGICAL METHOD, DEVICE, SYSTEM AND KIT FOR THE TREATMENT OF HYDROCEPHALUS

(71) Applicant: The Penn State Research Foundation, University Park, PA (US)

(72) Inventors: Barry M. Fell, Hummelstown, PA (US); Randy S. Haluck, Lititz, PA (US); Sprague W. Hazard, III, Hummelstown, PA (US); Elias B. Rizk, Harrisburg, PA (US)

(73) Assignee: The Penn State Research Foundation, University Park (PA)

( * ) Notice: Subject to any disclaimer, the term of this patent is extended or adjusted under 35 U.S.C. 154(b) by 716 days.

(21) Appl. No.: 17/441,774

(22) PCT Filed: Mar. 25, 2020

(86) PCT No.: PCT/US2020/024585
§ 371 (c)(1),
(2) Date: Sep. 22, 2021

(87) PCT Pub. No.: WO2020/198289
PCT Pub. Date: Oct. 1, 2020

(65) Prior Publication Data
US 2022/0176090 A1  Jun. 9, 2022

Related U.S. Application Data

(60) Provisional application No. 62/823,223, filed on Mar. 25, 2019.

(51) Int. Cl.
*A61M 27/00* (2006.01)
*A61B 17/17* (2006.01)
(Continued)

(52) U.S. Cl.
CPC ....... *A61M 27/006* (2013.01); *A61B 17/1739* (2013.01); *A61M 39/10* (2013.01); *A61B 2090/103* (2016.02); *A61M 2039/025* (2013.01)

(58) Field of Classification Search
CPC ................ A61M 27/006; A61M 39/10; A61M 2039/025; A61B 2090/103; A61B 17/1739
See application file for complete search history.

(56) References Cited

U.S. PATENT DOCUMENTS

| | | |
|---|---|---|
| 9,402,982 B2 | 8/2016 | Baert et al. |
| 9,737,697 B2 | 8/2017 | Heilman et al. |
| | (Continued) | |

FOREIGN PATENT DOCUMENTS

| | | | | |
|---|---|---|---|---|
| WO | WO-9633766 A1 | * | 10/1996 | ............ A61M 25/02 |
| WO | WO-2018005621 A1 | * | 1/2018 | |
| WO | 2020198289 A1 | | 10/2020 | |

OTHER PUBLICATIONS

Sharkey, Paul, Ventriculosagittal-Sinus Shunt, Journal of Neurosurgery, Publication dated May 11, 1964, pp. 362-367.
(Continued)

*Primary Examiner* — Ariana Zimbouski
(74) *Attorney, Agent, or Firm* — Dinsmore & Shohl LLP

(57) ABSTRACT

A modular cerebrospinal fluid (CSF) drain system for treating hydrocephalus without penetration of the gray matter of the brain is disclosed. Modular components of the CSF drain system may include a subarachnoid space (SAS) inlet drain implant, a SAS implant plug, a connector implant, a dural venous sinus (DVS) implant plug, and a DVS outlet drain implant. When implanted, the modular components may be fluidly coupled such that cerebrospinal fluid may flow from a subjects subarachnoid space through the modular components and into the subjects cerebral venous sinuses. A kit
(Continued)

including a guide device and the CSF drain system, as well as a method for installing the CSF drain system are also disclosed.

12 Claims, 36 Drawing Sheets

(51) Int. Cl.
*A61B 90/10* (2016.01)
*A61M 39/10* (2006.01)
*A61M 39/02* (2006.01)

(56) References Cited

U.S. PATENT DOCUMENTS

| | | | |
|---|---|---|---|
| 2003/0199831 A1 | 10/2003 | Morris et al. | |
| 2005/0059922 A1* | 3/2005 | Kuhlman | A61M 27/006 604/8 |
| 2005/0085764 A1 | 4/2005 | Borgesen | |
| 2008/0195178 A1 | 8/2008 | Kuzma | |
| 2014/0073859 A1* | 3/2014 | Schorn | A61N 1/0539 600/300 |
| 2015/0165166 A1* | 6/2015 | Gill | A61B 17/3415 604/164.01 |
| 2017/0119527 A1 | 5/2017 | Chavez et al. | |
| 2018/0256866 A1 | 9/2018 | Malek et al. | |
| 2019/0030322 A1 | 1/2019 | Schulte et al. | |

OTHER PUBLICATIONS

Baert, Edward Jozef, Treating Hydrocephalus with Retrograde Ventriculosinus Shunt: Prospective Clinical Study, www.sciencedirect.com; Oct. 2018, 9 pages.

Børgesen, Svend Erik, Shunting to the cranial venous sinus using the SinuShunt, Childs Nerv Syst (2004) 20:397-404 DOI 10.1007/s00381-004-0914-6, pp. 397-404.

El-Shafei, Ismail L., The retrograde ventriculosinus shunt: concept and technique for treatment of hydrocephalus by shunting the cerebrospinal fluid to the superior sagittal sinus against the direction of blood flow, Child's Nerv Syst (2001) 17:457-465 DOI 10.1007/s003810100456, p. 457-465.

Taylor, Joshua, Development of a computational model for macroscopic predictions of device-induced thrombosis, Biomech Model Mechanobiol (2016) 15:1713-1731 DOI 10.1007/s10237-016-0793-2.

Toma, Ahmed K., Ventriculosinus shunt, Received: Jun. 16, 2009 / Revised: Nov. 2, 2009 / Accepted: Jan. 2, 2010 / Published online: Feb. 23, 2010, Neurosurg Rev (2010) 33:147-153.

* cited by examiner

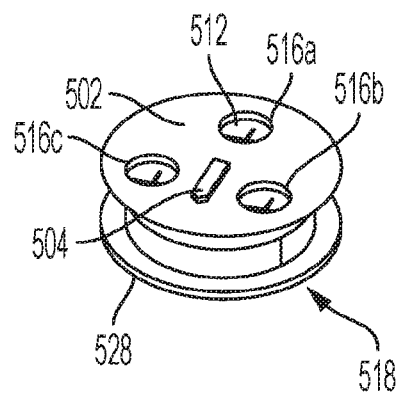
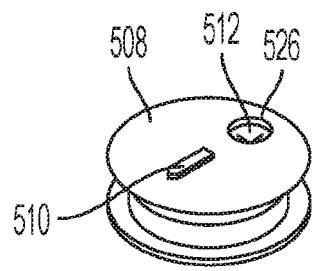
FIG. 5A  FIG. 5C
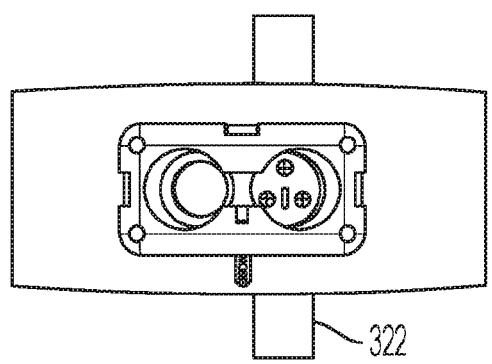
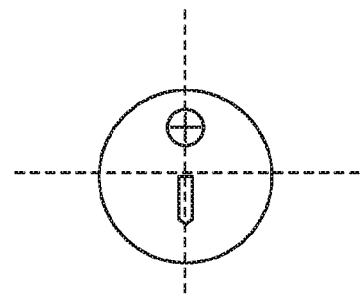
FIG. 5B  FIG. 5D
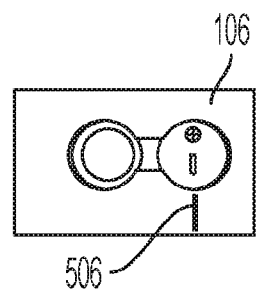
FIG. 5E
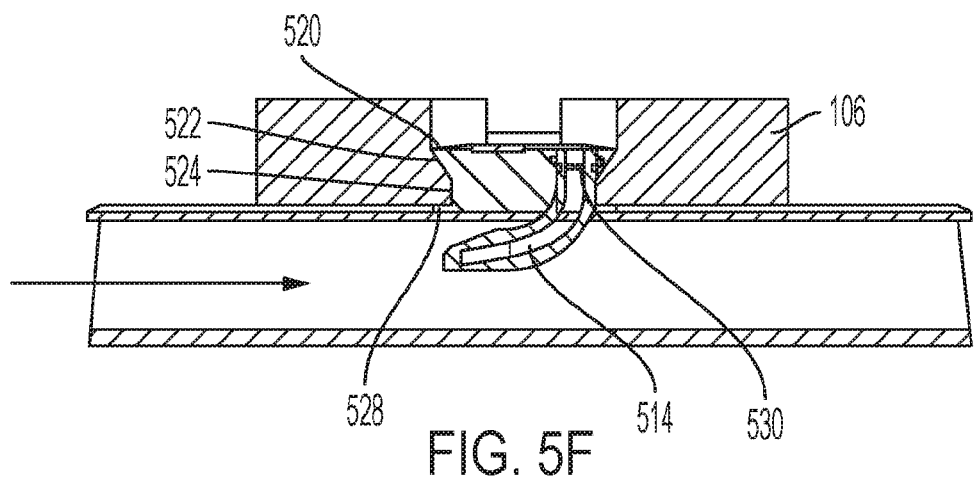
FIG. 5F

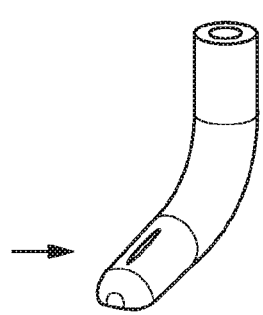
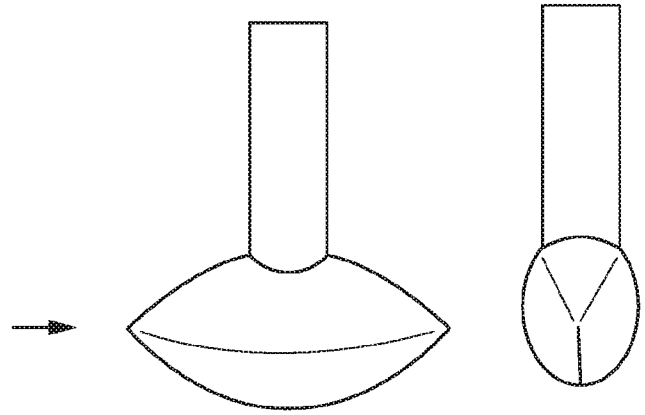
FIG. 7A    FIG. 7B
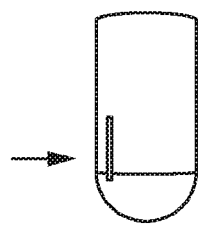
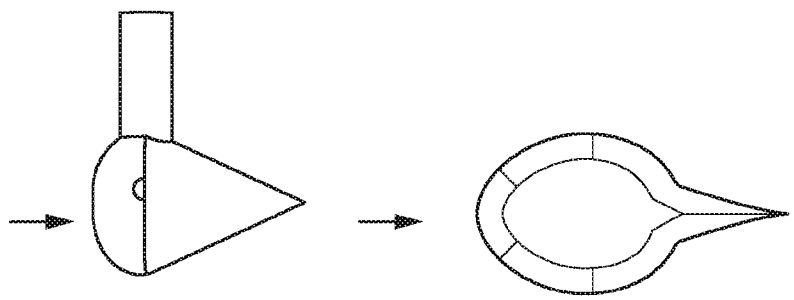
FIG. 7C    FIG. 7D    FIG. 7E
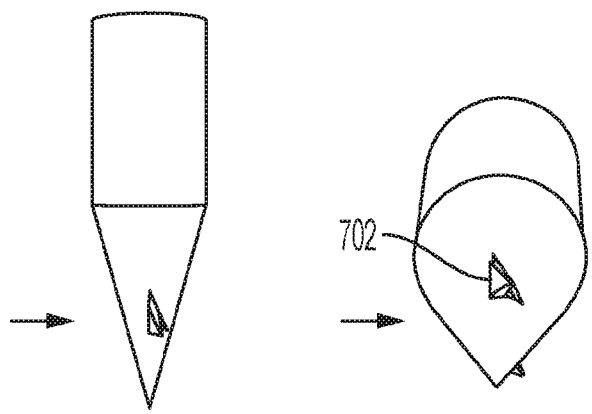
FIG. 7F

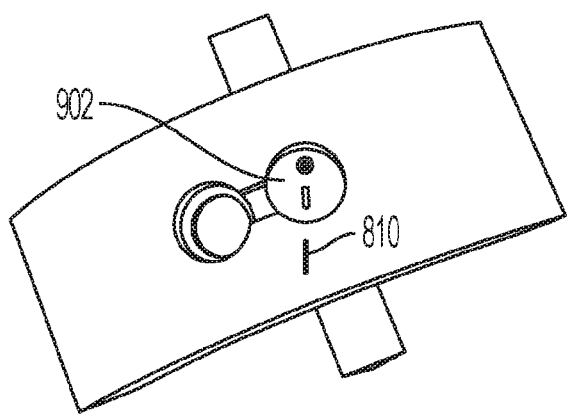
FIG. 9A
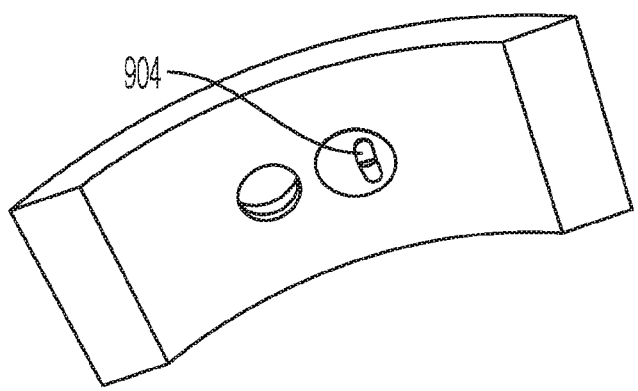
FIG. 9B
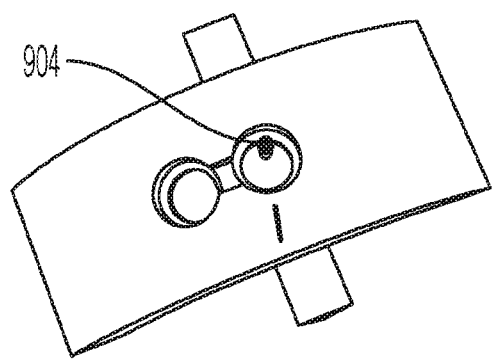 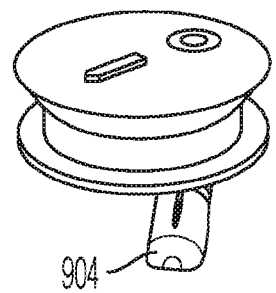
FIG. 9C    FIG. 9D

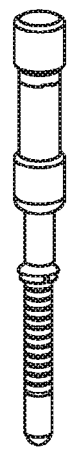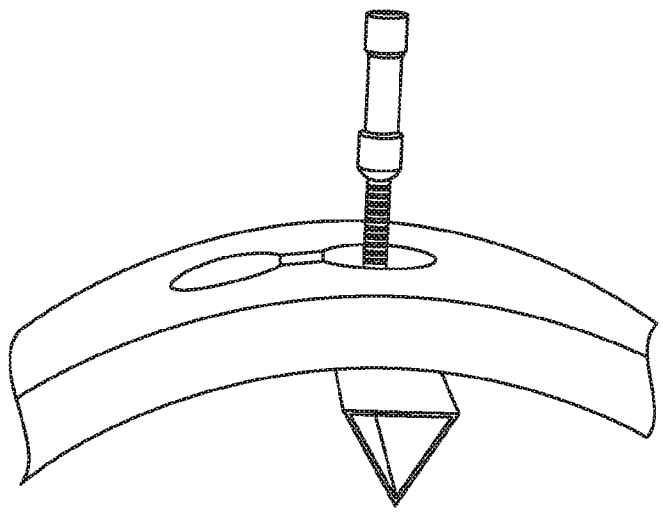
FIG. 17A  FIG. 17B
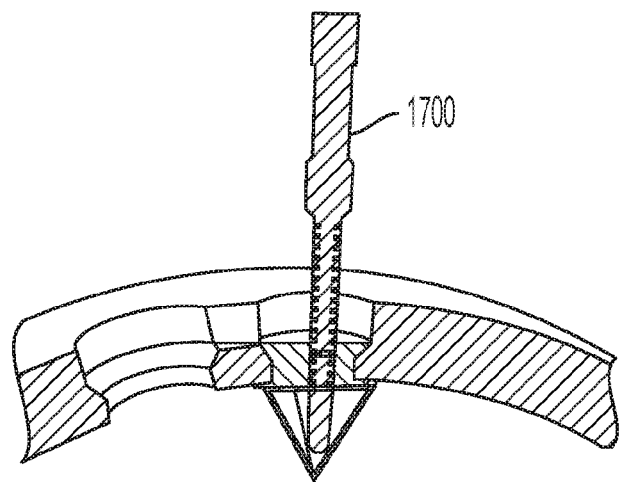
FIG. 17C

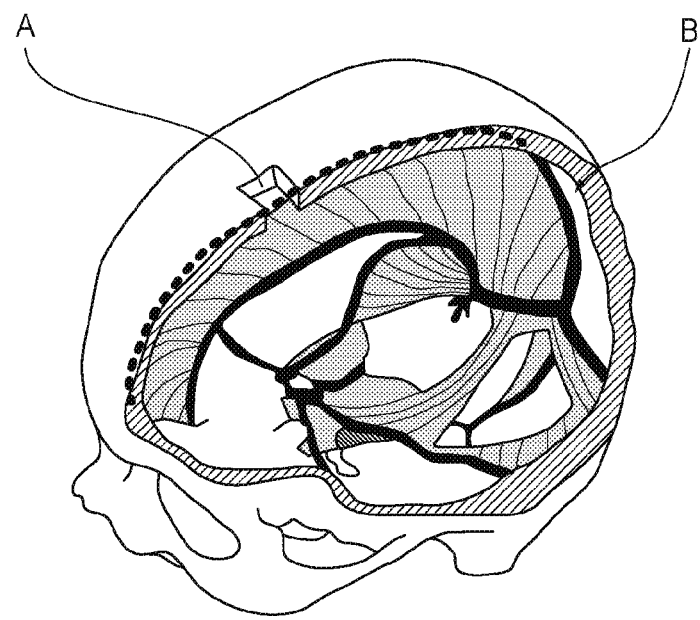
FIG. 32A
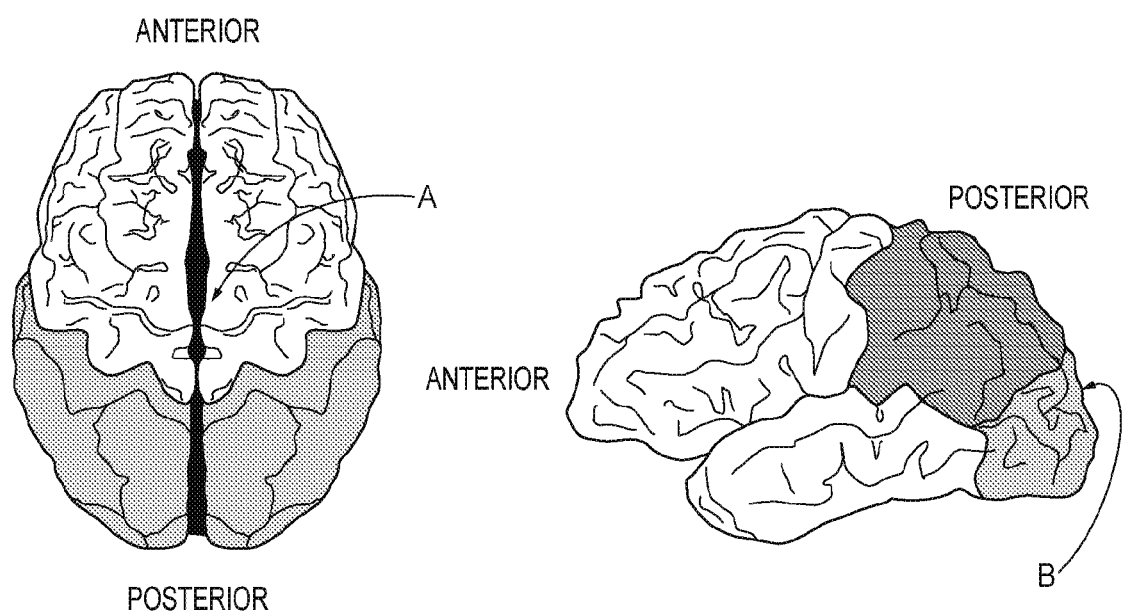
FIG. 32B
FIG. 32C

SURGICAL METHOD, DEVICE, SYSTEM AND KIT FOR THE TREATMENT OF HYDROCEPHALUS

CROSS-REFERENCE TO RELATED APPLICATIONS

This application is the U.S. National Stage of PCT/US2020/024585 filed Mar. 25, 2020, which claims priority to U.S. Provisional Patent Application Ser. No. 62/823,223, filed Mar. 25, 2019, the entire content of both are incorporated by reference herein in their entirety.

FIELD OF THE INVENTION

The present disclosure relates to devices, systems, and methods for accessing the subarachnoid space in a subject, and more particularly, to devices, systems, and methods to drain cerebrospinal fluid from the subarachnoid space into the cerebral venous sinuses without penetration of the gray matter of the brain.

BACKGROUND OF THE INVENTION

Existing configurations for devices that are used to treat accumulation of excess fluid in a cranial space of a subject have attempted to address improved shunt designs, improved one-way valves, reduced catheter blockages, incorporate material improvements to reduce the occurrence of infections, or other variations in catheter (e.g., tube) systems to improve upon associated performance issues. However, such designs continue to suffer high failure rates from issues such as challenging surgical procedures to implant the catheters, too much or too little cerebrospinal fluid (CSF) fluid flow, susceptibility to periodic blockages or clots, infections, inadequate removal of excess fluid from any of the subarachnoid space or ventricles of the brain and drainage rates impacted by a change of subject position. Furthermore, concerns associated with existing and other proposed methods include the risk of significant bleeding, the risk of introducing air into the dural venous sinuses (e.g., potential embolism), and the inability to properly place a catheter in the SAS or other CSF containing space.

SUMMARY OF THE INVENTION

Embodiments of the present disclosure include a combined implant device that is mounted to the cranium of the subject. The combined device consists of a first element that provides safe access to cerebrospinal fluid (CSF) found in the subarachnoid space, a separate second element that provides safe access to the venous system to provide drainage of the CSF coming from the first element, and a third connecting element located between, and connected to, the first and second elements that: 1) allows CSF fluid to flow between the first and second elements, 2) allows on-going maintenance access to the first and second elements, 3) allows in-situ testing of the functional performance of the first and second elements, and/or 4) has a low profile shape that does not cause erosion of the skull post-surgery.

In one embodiment, an implant system (e.g., CSF drain system) including a subarachnoid space (SAS) implant, a dural venous sinus (DVS) implant, and a connector implant, is disclosed. According to various aspects, at least one of the SAS implant, the DVS implant, or the connector implant may be affixed (e.g., via screw, adhesives, and/or the like) to a cranium of a subject. According to further aspects, the SAS implant may be fluidly coupled to the DVS implant via the connector implant.

In another embodiment, a guide device including a body, a first aperture, and a second aperture is disclosed. The first aperture and the second aperture may be defined though a height of the body. The first aperture and the second aperture may be sized to fit within a width and a depth of the body without an overlap between the first aperture and the second aperture. A distance between a center of the first aperture and a center of the second aperture may be a predetermined distance. The predetermined distance may be a distance between burr holes to be drilled in a subject's cranium.

These and additional features provided by the embodiments described herein will be more fully understood in view of the following detailed description, in conjunction with the drawings.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be understood when read in conjunction with the following drawings, where like structure is indicated with like reference numerals and in which:

FIG. 5A depicts a perspective view of an illustrative DVS implant plug including a plurality of DVS outlet drain implant locations, according to one or more embodiments shown and described herein;

FIG. 5B depicts a top view of an illustrative placement of the DVS implant plug of FIG. 5A within the outlet burr hole of the subject's skull, according to one or more embodiments shown and described herein;

FIG. 5C depicts a perspective view of an illustrative rotatable DVS implant plug including a single DVS outlet drain implant location, according to one or more embodiments shown and described herein;

FIG. 5D depicts a top view the illustrative rotatable DVS implant plug of FIG. 5C according to one or more embodiments shown and described herein;

FIG. 5E depicts a top view of an illustrative placement of the rotatable DVS implant plug of FIG. 5C within the outlet burr hole of the subject's skull according to one or more embodiments shown and described herein;

FIG. 5F depicts a cross-sectional view of an illustrative DVS implant plug including a DVS outlet drain implant inserted into the sinus, according to one or more embodiments shown and described herein;

FIG. 7A depicts a perspective view of an illustrative shape of an outlet tip of a DVS outlet drain implant, according to one or more embodiments shown and described herein;

FIG. 7B depicts a side view and a front view of an illustrative shape of an outlet tip of DVS outlet drain implant, according to one or more embodiments shown and described herein;

FIG. 7C depicts a side view of an illustrative shape of an outlet tip of a DVS outlet drain implant, according to one or more embodiments shown and described herein;

FIG. 7D depicts a side view of an illustrative shape of an outlet tip of a DVS outlet drain implant, according to one or more embodiments shown and described herein;

FIG. 7E depicts a bottom view of an illustrative shape of an outlet tip of a DVS outlet drain implant, according to one or more embodiments shown and described herein;

FIG. 7F depicts a side view and a bottom view of an illustrative shape of an outlet type of a DVS outlet drain implant, according to one or more embodiments shown and described herein;

FIG. 9A depicts a top view of an illustrative DVS outlet drain implant as positioned within a DVS implant plug via the DVS positioning system of FIG. 8A, according to one or more embodiments shown and described herein;

FIG. 9B depicts a bottom perspective view of the illustrative DVS outlet drain implant of FIG. 9A, according to one or more embodiments shown and described herein;

FIG. 9C depicts a top view of the illustrative DVS outlet drain implant of FIG. 9A relative to the sinus with the DVS implant plug removed, according to one or more embodiments shown and described herein;

FIG. 9D depicts a perspective view of the illustrative DVS outlet drain implant of FIG. 9A as oriented relative to the DVS implant plug, according to one or more embodiments shown and described herein;

FIG. 17A depicts a perspective view of an illustrative instrument to check for physical depth of the sinus to properly size and/or position a DVS outlet drain implant including an outlet tip for DVS implant plug prior to insertion, according to one or more embodiments shown and described herein;

FIG. 17B depicts a perspective view of the illustrative instrument of FIG. 17A relative to the sinus, according to one or more embodiments shown and described herein;

FIG. 17C depicts a cross-sectional view of the illustrative instrument of FIG. 17B checking sinus depth, according to one or more embodiments shown and described herein;

FIG. 32A depicts a perspective cross sectional view of a subject's head, indicating illustrative placements of an intracranial catheter, according to one or more embodiments herein;

FIG. 32B depicts an axial view of a subject's brain, indicating an illustrative placement of an intracranial catheter, according to one or more embodiments shown and described herein;

FIG. 32C depicts a sagittal view of a subject's brain, indicating an illustrative placement of an intracranial catheter, according to one or more embodiments shown and described herein;

DETAILED DESCRIPTION OF THE INVENTION

Figure 1:
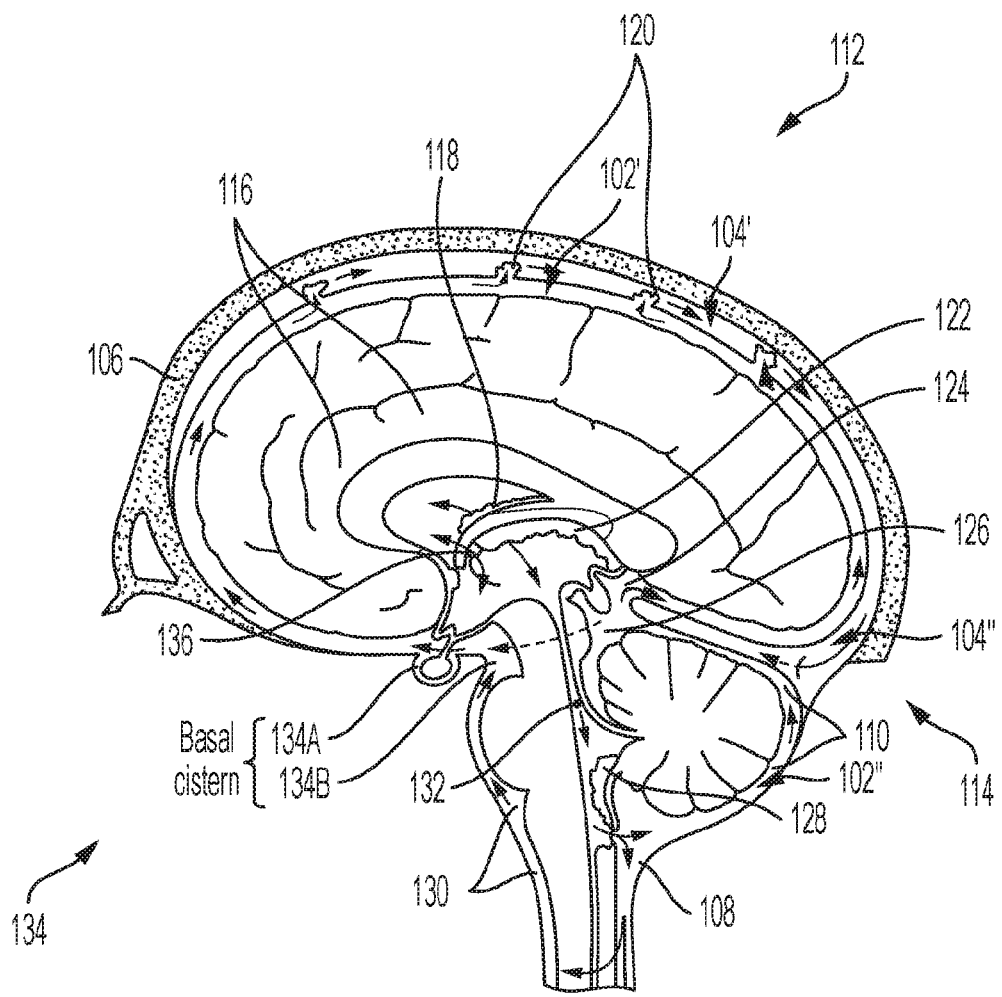
FIG. 1 depicts a sagittal view of an illustrative superior placement location on a subject's skull and an illustrative posterior placement location on the subject's skull for an implant system, according to one or more embodiments shown and described herein.

Embodiments described herein generally relate to systems, devices, and/or methods for recreating normal biological fluid flow patterns by generally reproducing one of the functions of arachnoid villi to drain excess cranial fluid into the dural venous sinuses and ultimately to the jugular veins.

The systems and/or devices described herein are particularly designed and constructed to span the ventricles and other cerebrospinal fluid (CSF) containing spaces, such as a subarachnoid or other subdural spaces, directly into the dural sinus(es) for drainage, which are distinctly different anatomic locations and compartments. The systems and/or devices described herein are further designed and positioned such that fluid (e.g., CSF) contained in a ventricle and other subarachnoid or subdural spaces is drained by the systems and/or devices described herein due to the relatively higher pressure differential found in CSF containing spaces and the relatively lower pressure of the dural sinuses. Moreover, the systems, devices, and/or methods described herein allow for minimal blood loss and/or no air embolus and air entry into the venous system, which could be potentially fatal. The systems, devices, and/or methods described herein also allow for ease of recurrent access into an implantable device without exsanguinating or killing the subject, particularly young subjects. More specifically, the systems, devices, and/or methods described herein allow for such recurrent access into an implantable device without penetration of the gray matter of the brain. The systems, devices, and/or methods described herein are particularly useful for relatively young subjects (e.g., children, due to relatively smaller surgical sites).

Cerebrospinal fluid (CSF) is a ubiquitous fluid similar in composition to water that bathes central nervous system structures in the cranial cavity and the spinal canal. CSF may be formed in a continuous fashion at a rate that ranges between 0.1 to 0.7 ml per minute to a total amount, in some subjects, up to or in excess of 600 ml per day. This fluid is absorbed across several routes. These include, but are not limited to, the arachnoid villi into the venous sinus circulation and into the lymphatic vessels around the cranial cavity and spinal canal. The arachnoid villi form a one-way valve between the subarachnoid space (SAS) and the dural venous sinuses (DVS). The arachnoid granulations are exposed to CSF that resides in the SAS on the basal side and to the venous blood of the dural sinuses on the apical side (see FIG. 1, described more fully herein). This pathway may be disrupted in individuals with hydrocephalus, which can lead to a buildup of fluid and a subsequent increase in intracranial pressure. The SAS is the region around the brain and is bounded by dura matter, which also contains CSF with a typical volume of 150 ml out of an approximate total of 500 ml in the central nervous system.

Hydrocephalus, which is an abnormal accumulation of CSF within the brain, is a frequently encountered problem, both in adult and child subjects. Excess CSF accumulation or production, in children and/or adults, may result in relatively high or abnormally high intracranial pressures (e.g., a condition known as Normal Pressure Hydrocephaly (NPH)). If left untreated, NPH may result in death. In relatively older subjects, where the volume of CSF is too high, the subject's symptoms may mimic Alzheimer's and/or other degenerative brain diseases. Hydrocephalus is one of the most frequently encountered problems in neurosurgery, both in adults and in the pediatric population. This condition is commonly treated using a surgical procedure in which a tube, referred to as a "shunt," is placed into the subject's body. This device was introduced as a medical treatment of hydrocephalus in the 1950s and has remained virtually unchanged for the past 50 years. More specifically, this procedure involves placing a silicone rubber catheter into the cerebral ventricular space and diverting accumulating CSF through an extensive intracranial tubing (e.g., a catheter) outside of the skull and to a distal reabsorption area (e.g., the peritoneal cavity, the pleural cavity, the right atrium of the heart, and/or the like).

In contrast, the present disclosure relates to the treatment of fluid accumulation within the cranial cavity by permitting the flow of fluid from the subarachnoid space into the venous system. The treatment described herein may be utilized for conditions that cause fluid accumulation (e.g., hydrocephalus and/or the like). As such, the present disclosure is not related solely to the treatment of hydrocephalus and/or the drainage of CSF. Other fluids and conditions for which the systems, devices, and/or methods described herein can be used for treatment should generally be understood.

It should also be understood that the present disclosure is not solely related to fluid removal and redirection. That is, in some embodiments, the systems, devices, and/or methods described herein may further be used for the purposes of targeted drug delivery and/or the removal of components found in CSF (e.g., amyloid proteins and/or the like). For example, chemotherapy medication, ALS medication, Alzheimer's medication (e.g., chelating or enzymatic methods), stroke treatment medication (e.g., TPA), genetic (e.g., chromosomal) manipulation therapy, treatments for bacterial or viral infections, treatment for brain hemorrhage control, and/or the like may be delivered to or from particular areas (e.g., the dural venous sinus, including the sagittal sinus, the transverse sinus, and the like, the subarachnoid space, and/or the like) that are accessed by the systems, devices, and/or methods described herein.

The present disclosure pertains to a surgical method, device, system and/or kit for the treatment of hydrocephalus. Accordingly, a further goal of the present disclosure is to relieve excess CSF pressure via a direct subarachnoid space (SAS) to dural venous sinus (DVS) drainage via an implant system (e.g., a HydroFix implant system, a CSF drain system, or the like) as described herein.

Existing endovascular systems/methods only provide indirect access to the SAS. For example, the indirect access may be provided via an inferior petrosal sinus vein to the dura and to the SAS. Components of such systems are difficult to change and there is generally no post-surgical access to an implant. Post-surgical access to an implant, if possible, is often very challenging and/or invasive.

In contrast, embodiments of the present disclosure provide direct access to the SAS, to the DVS, and to the implant. More specifically, the direct access may be provided to the SAS through the dura via channels to the DVS.

Further, various components of the present disclosure are easily changed (e.g., modular) and provide easy post-surgical access. Furthermore, embodiments of the present disclosure provide additional options such as a mechanical purge mechanism and the ability to add medications to the site and/or the implant.

More specifically, aspects of the present disclosure provide a specific surgical guide(s). Further aspects provide an improved shunt design. Yet further aspects provide surgical methods, including the option of adding surgical navigation to the procedure, which can minimize the risk of the surgery to the subject while facilitating the surgeon's ability to easily perform the operation.

More specifically, the present disclosure presents surgical tools and shunt designs that allow for accurate placement of an implant, affixing any or all of the implant components directly or indirectly to the cranium/skull, and positive control of the dura membrane during all aspects of the procedure, thus mitigating the potential risk of incidental dura venous sinus (DVS) membrane rupture and subsequent bleeding. For example, surgical tools and shunt designs of the present disclosure include positional cues that further reduce the risk of this procedure by allowing the surgeon to have absolute confirmation of implant orientation and final placement.

The implant system (e.g. HydroFix implant system, a CSF drain system, or the like), associated instruments, and surgical procedures described herein may dramatically reduce the cost and morbidity associated with existing standard of care while significantly increasing the number of subjects eligible for treatment.

According to various embodiments described herein, an implant system may be mounted to the cranium/skull of a subject. The implant system may include a combination of devices including a first element (e.g., FIG. 13A, reference 1002) that provides safe access to cerebrospinal fluid (CSF) found in the subarachnoid space (SAS), a separate second element (e.g., FIG. 13A, reference 508) that provides safe access to the venous system (e.g., the dural venous sinuses (DVS)) to provide drainage of the CSF flowing from the first element and a third connecting element (e.g., FIG. 13B, reference 1302) located between, and connected to, the first element and the second element that 1) allows/enables CSF fluid to flow from the first element to the second element, 2) allows/enables on-going maintenance access to the first element and/or the second element, 3) allows/enables in-situ testing of the functional performance of the first element and/or the second element, and 4) defines a low profile shape that does not cause erosion of the skull/cranium post-surgery. The first element may be referred to as an SAS element/implant, the second element may be referred to as the DVS element/implant, and the third element may be referred to as a connector element/implant.

According to other embodiments, systems, devices and/or methods of the present disclosure include mechanisms and/or instruments to ensure proper placement and/or performance of the various implant components as described herein. According to various aspects, the system described herein ensures that the implants' position is properly registered to the skull bone (e.g., using an external guide device that is used, in conjunction with computed tomography (CT) navigation methods (e.g., using a StealthStation® from Medtronic®, Minneapolis, MN), to pre-determine the correct anatomical location of the drilled holes in the skull bone). Once drilled using the guide device, the holes may be modified, if needed, for better access in the skull bone and then may intimately receive the first element (e.g., SAS element/implant), the second element (e.g., the DVS element/implant), and the third element (e.g., the connector element/implant). According to such aspects, the holes in the skull bone dictate registration of the first element, the second element, and the third element with respect to fixation to the subject's anatomy. Additionally, the drilled holes may also ensure proper orientation of the first element, the second element, and the third element relative to desired anatomy of the subject (e.g., the SAS, the DVS, and/or the like) during and at completion of the surgery and thereafter. The implant system of the present disclosure is unique in that it allows visibility of and/or separate access to each implant element (e.g., the first element, the second element, and/or the third element) at all times during and/or after surgery.

Aspects of the present disclosure further include a modular set of surgical elements as well as a surgical technique that allows for each element's surgical implantation to be completed independent of each other in a discreet, safe, controlled manner, while allowing for subject specific component sizing.

The SAS element/implant (e.g., first element) may be implanted to provide access to CSF found in the subarachnoid space (SAS). The design of the SAS element/implant may include an integral sealing element (e.g., FIG. 10D, reference 1016) that does not allow the CSF to escape without first being joined to the connecting element/implant (e.g., third element). The SAS element/implant may also include a CSF inlet that is designed to prevent collapse of surrounding tissue and to ensure a continuous access to the CSF.

In a similar manner, the DVS element/implant (e.g., second element) may provide access for controlled CSF drainage into the dural venous sinuses (DVS). The design of the DVS element/implant may include an integral sealing element (e.g., FIG. 5A, reference 512) that does not allow for the backflow of venous blood at any time, nor the unintended entry of any fluid or air into the sinus without deliberate connection to the connecting element/implant (e.g., third element). The DVS element/implant may also include an integrated, one way drain outlet design (e.g., an internal pressure activated slit or flap valve, and/or the like), the drain outlet design positionable within the venous sinus such that it does not allow for the backflow of venous blood at any time.

Further embodiments of the present disclosure include a method of implanting the DVS element/implant in a manner that provides safe, controlled access to a dural venous sinus (DVS) (e.g., the sagittal sinus, the transverse sinus, and/or the like) without the risk of causing inadvertent and/or significant bleeding. According to various aspects, an inferior portion of the DVS implant may be temporarily or permanently bonded (e.g., via an adhesive, a hemostatic agent, and/or the like) to the dural covering of the sinus, thus effectively increasing the local stiffness of the immediate dural covering and reducing the chance of a dural tear and/or bleeding. A CSF outlet drain may then be inserted through the dural covering and into the sinus through the DVS implant. The dural covering, locally stiffened via the DVS implant, may prevent unintentional tearing of the dural covering and avoid any uncontrolled or unnoticed bleeding between the dural covering and the bone and/or between the dura and the cortex of the brain.

According to various aspects described herein, the connecting element/implant may be a needle, a tube, a tube connected to a needle, and/or a multi-functional connecting element/implant that contains discreet regions of access to the SAS element/implant, and/or the DVS element/implant.

According to further aspects, the connecting element/implant may include further features including a general common area of fluid collection (e.g., a bladder to hold medication) and/or a compressible region (e.g., to temporarily facilitate a movement of CSF between the SAS element/implant and the DVS element/implant.

Yet further embodiments of the present disclosure include a surgical technique and implantation method that is Safe, Modular, Accessible (for maintenance), Reproducible, and easily Replaceable Technology (SMARRT). The various implants described herein do not require advanced surgical skills because the implants and the associated instruments are designed, as described herein, to substantially limit a chance of inadvertent damage to the brain and/or to instigate uncontrollable bleeding. The implantable elements of the invention utilize guided positioning on the skull, have controlled depth penetration into the skull, and have minimal penetration of the dura. At no time, do the implants of the present disclosure require penetration of the brain cortex and/or the ventricle for access to the CSF for drainage into the sinus system.

The SMARRT technique, as described herein, is significantly easier than other, more surgically complicated procedures (e.g., traditional CSF intracranial external ventricular drain (EVD), an endovascular cerebrospinal fluid (CSF) transdural deployment shunt device, through a transvenous transfemoral approach, into the cerebellopontine angle cistern for access to the CSF (e.g., the CeraVasc approach), Endoscopic Third Ventriculostomy (ETV), and/or Endoscopic Third Ventriculostomy/Choroid Plexus Cauterization (ETV/CPC)).

Referring generally to FIG. 1, aspects of the present disclosure pertain to a set of implants, instrumentation, a surgical method and a surgical kit utilized to relive excess CSF pressure (e.g., for cases of hydrocephalus) and/or excess fluid (e.g., for cases of Normal Pressure Hydrocephaly (NPH)) in/on a subject's brain by placing an inlet channel in the subarachnoid space (SAS) of the brain (e.g., reference 102', 102", shown as green in FIG. 1) and providing a direct outlet into the dural venous sinus (DVS) of the brain (e.g., reference 104', 104", shown as dark blue in FIG. 1).

In view of FIG. 1, one aspect of the present disclosure includes a superior placement location (e.g., depicted generally at location 112) on the skull 106. In such an aspect, a superior region of the SAS 102' may be accessed with drainage into the superior sagittal sinus 104'. More generally, drainage may be into a dural venous sinus (e.g., the sagittal sinus, the traverse sinus, and/or the like). Another aspect of the present disclosure includes a posterior placement location (e.g., depicted generally at location 114) on the skull 106. In such an aspect, the cerebellomedullary cistern 108 (e.g., with median aperture of the fourth ventricle), vermian cistern 110 or similar cistern surrounding the cerebellum is accessed with drainage into the straight sinus, or if lower, the transverse sinus but generally in the occipital region of the skull 106 (see e.g., location 114). More generally, drainage may be into the dural venous sinus. The subarachnoid space 232 (SAS) is a generally complex, convoluted space between the arachnoid matter 234 and the pia matter 236 (e.g. FIG. 2B) that extends from the skull 106 to the bottom of the spinal cord and that contains CSF. The sagittal sinus, along the top middle/central portion of the skull is generally triangular shaped, while at about ear level of a subject, the sagittal sinus is more circular shaped. According to such aspects, superior placement may permit an implant system including relatively shorter inlets and/or outlets and posterior placement may permit an implant system including relatively longer inlets and/or outlets. Further anatomical structures depicted in FIG. 1 include the interhemispheric cistern 116, the choroid plexus of the lateral ventricle 118, arachnoid granulations 120, the choroid plexus of the third ventricle 122, the transverse cistern 124, the ambient cistern 126, the choroid plexus of the fourth ventricle 128, the pontomedullary cistern 130, the cerebral aqueduct 132, the basal cistern 134 (e.g., including the chiasmatic cistern 134A and the interpeduncular cistern 134B), and the interventricular foramen 136.

Figure 2A:
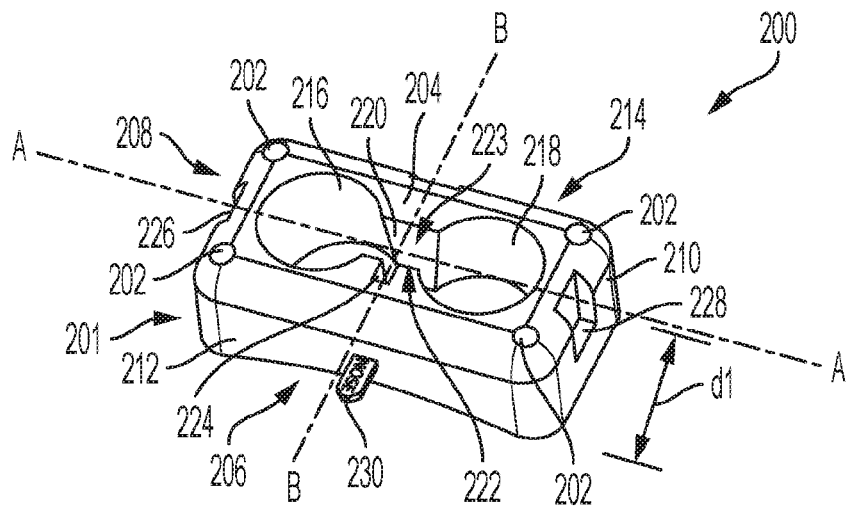
FIG. 2A depicts an illustrative guide device to install the implant system at the locations of FIG. 1, according to one or more embodiments shown and described herein.
Figure 2B:
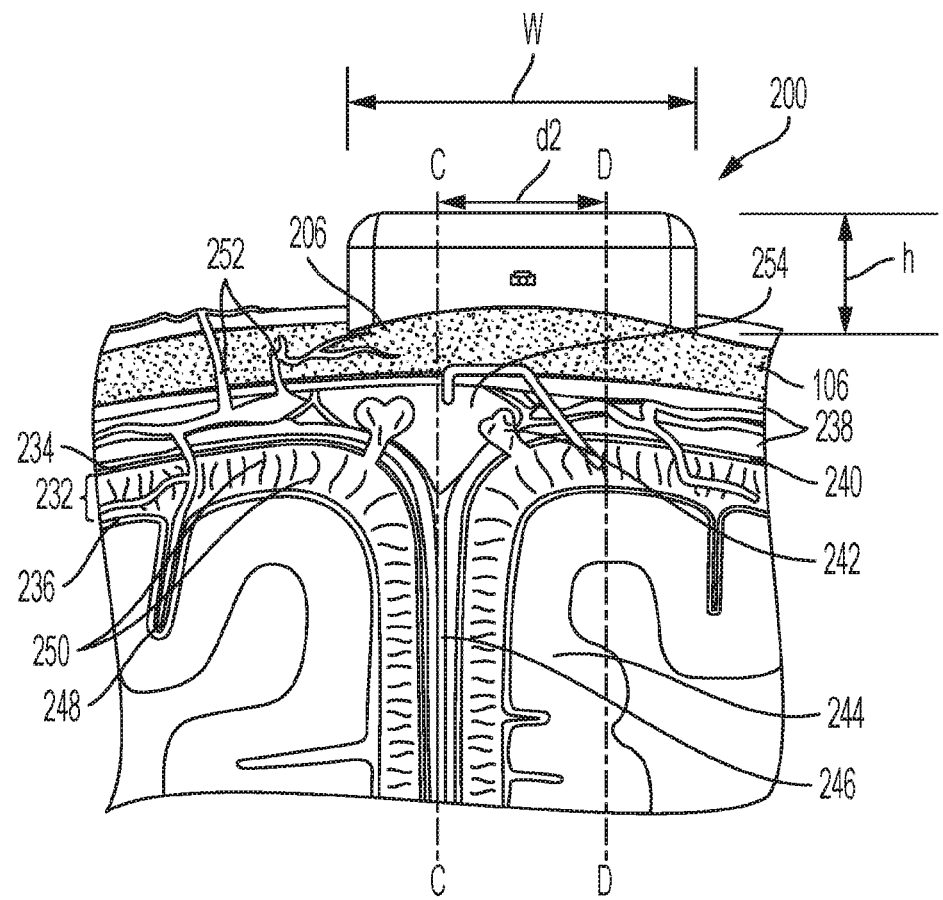
FIG. 2B depicts a coronal view of the illustrative guide device of FIG. 2A, at the superior placement location of FIG. 1, according to one or more embodiments shown and described herein.

FIG. 2A depicts an illustrative guide device 200 to assist installation of the implant system (e.g., HydroFix implant system) described herein according to one or more embodiments of the present disclosure. More specifically, the guide device 200 may be used to drill burr holes in a controlled fashion (e.g., a template so that the burr holes are spaced and oriented in a predefined manner). Referring to FIG. 2B, the guide device 200 is designed to temporarily attach directly to a skull 106 during surgery to implant the implant system. The guide device 200 may be removed and discarded after the implant system has been placed. According to various embodiments, the guide device 200 may attach to the skull 106 via an attachment component(s) (e.g., via a screw(s), and/or the like). For example, each attachment component may be positioned through one or more apertures 202 defined through a height "h" (see FIG. 2B) of the guide device 200. A step or a ledge may be defined within each aperture 202 to interferingly engage each attachment component (e.g., head of screw). A body 201 of the guide device 200 may be manufactured using a material (e.g., polymer, metal, and/or the like suitable to guide a drill while removing skull bone) to define a top surface 204, a bottom surface 206, a left surface 208, a right surface 210, a front surface 212 and a back surface 214 with dimensions including a depth "d1", a height "h" (FIG. 2B), and a width "w" (FIG. 2B). According to various aspects, the guide device 200 may be manufactured via various processes (e.g., a blow molding process, an injection molding process, a machining process, a 3D printing process, and/or the like).

Referring again to FIG. 2A, one or more access apertures (e.g., a first access aperture 216, a second access aperture 218, and/or the like) may be defined through a height "h" (FIG. 2B) of the guide device 200. According to various aspects, each access aperture 216, 218 may be defined normal/perpendicular to a surface of the skull 106 (e.g., along axis C-C, along axis D-D, as depicted in FIG. 2B). According to some aspects, the axis C-C and/or the axis D-D may be specific to and/or a function of local contours of the skull and/or surrounding anatomy. Accordingly, in some aspects, the burr holes and/or implant plugs, as described herein, may similarly be specific to and/or a function of the local contours of the skull and/or the surrounding anatomy. Although the one or more access aperture 216, 218 is depicted as circular in shape (see FIG. 2A) it should be understood that the one or more access aperture 216, 218 may be another shape (e.g., square, rectangular, polygonal, ovoid, irregular and/or the like). According to some aspects, each access aperture 216, 218 may be sized to fit within the depth "d1" and width "w" of the guide device 200 without overlapping another access aperture 216, 218, respectively. In such an aspect, a first connector bridge or wall 220 and a second connector bridge or wall 222 may be defined through the height "h" of the guide device 200 between at least two access apertures (e.g., first access aperture 216 and second access aperture 218). The first connector bridge or wall 220 and the second connector bridge or wall 222 may also be defined normal/perpendicular to a surface of the skull 106. According to various embodiments, the first connector bridge or wall 220 and the second connector bridge or wall 222 may be used to define a connector space 223 to guide the removal of skull bone to create a connecting channel (FIG. 3A, connecting channel 324) between the first access aperture 216 and the second access aperture 218. According to various aspects, a surface of the first connector bridge or wall 220 and a surface of the second connector bridge or wall 222 may be used to guide a tool (e.g., a router, a burr bit of a drill, a rongeur, and/or the like). According to further aspects, a removable guide element aperture 224 may be defined through the height "h" of the guide device 200 in at least one connector bridge or wall (e.g., the second connector bridge or wall 222 in FIG. 2A). According to various aspects, the removable guide element aperture 224 may also be used to guide the removal of skull bone to create the connecting channel 324 (e.g., in the skull) between the first access aperture 216 and the second access aperture 218. Similarly, surfaces defined by the removable guide element aperture 222 may be used to guide a tool (e.g., a router, a burr bit of a drill, a rongeur, and/or the like). According to yet further aspects, one or more tool locator feature (e.g., a first tool locator feature 226, a second tool locator feature 228, and/or the like) may be defined in a surface (e.g., the left surface 208, the right surface 210, and/or the like) through at least a portion of the height "h" of the guide device 200. According to various aspects, the one or more tool locator feature may 226, 228 may position a tool (e.g., a router, burr bit and/or the like) relative to the skull (e.g., perpendicular) during skull bone removal. It should be understood that one or more tool locator feature may be similarly defined in another surface (e.g., the front surface 212, the back surface 214, and/or the like). Such further apertures and features may similarly be defined normal/perpendicular to a surface of the skull 106. In addition, referring to FIG. 2A, an anatomic guide pointer 230 may be selectively extended from a surface (e.g., front surface 212) of the guide device 200. The anatomic guide pointer 230 may be configured to slide within the body 201 of the guide device 200 when not in use. According to various aspects, the anatomic guide pointer 230 may include text defined thereon indicating to what it is referencing (e.g., "NOSE"). According to one aspect, the anatomic guide pointer 230 may be used to align the guide device 200 in a general anatomic referenced direction (e.g., direction of the subject's "NOSE").

In light of FIG. 2A, according to various embodiments, the guide device 200, including features thereof, may be symmetrical (e.g., about axis A-A and/or axis B-B as depicted in FIG. 2A). According to other embodiments, the guide device 200 may be asymmetrical (e.g., about axis A-A and/or axis B-B).

FIG. 2B depicts an illustrative superior placement of the guide device 200 according to one or more aspects of the present disclosure (e.g., Example 1 of FIG. 1). In view of FIG. 2B, the bottom surface 206 of the device may be sized and/or configured (e.g. contoured, with a natural curvature, and/or the like) to couple to a skull 106 (e.g., bone) of a subject (e.g., a patient). According to various aspects, various skull adapters (not shown) may define a plurality of skull contours and each skull adapter may be configured to accept a bottom surface 206 (e.g., default contour, flat contour, and/or the like) of the guide device 200 as well as apertures (e.g., as described herein) defined in the guide device 200. Further anatomical structures depicted in FIG. 2B include dura matter 238, the subdural space 240, arachnoid granulation villi 242, the cerebral cortex 244, the longitudinal fissure 246, the cerebral vein 248, the arachnoid trabeculae 250, pia matter 236, the subarachnoid space 232, arachnoid mater 234, veins 252 and the sinus 254.

According to various aspects, the guide device 200 may be located at its final position (e.g., superior, posterior, and/or the like) on the skull 106 as directed by a navigation device (e.g., AxiEM™ Electromagnetic Technology from Medtronic®, Minneapolis, MN, StealthStation®, and/or the like). According to other aspects, the guide device 200 may not be located via navigation (e.g., manually). As described herein, the guide device 200 may provide a drill and/or a cutting guide.

In some aspects, one or more than one reference point may be registered from a computed tomography (CT) scan/prescan or a magnetic resonance imaging (MRI) scan/prescan of the skull 106 and/or the brain. For example, navigated CT may be used to locate the sinus (e.g., plus/minus a few millimeters) as well as vascular areas and/or peripheral veins (e.g., of the subject) to avoid. According to various aspects, the one or more than one reference point (e.g., from a CT and/or MRI image) may be utilized to place the guide device 200 on the skull 106 at a particular prescribed location. For example, a navigated probe may be adapted to couple to or lock into the guide device 200 and the navigated probe may be used to position the guide device with respect to the one or more than one reference point. According to numerous aspects, referring briefly to FIG. 3B, an aperture 218 the guide device 200 may be positioned directly over the sinus (e.g. depicted in red). According to further aspects, the guide device 200 itself may be customized to include or depict the one or more than one reference point for future reference (e.g., when drilling, when cutting, when placing implants, when placing instruments, and/or the like). Such aspects minimize and/or eliminate a need for manual preparation and reduces the possibility of inducing inadvertent bleeding. According to various aspects, each aperture defined in the device 216, 218 (e.g., for implant placement, for instrument placement, and/or the like) may be referenced off of the guide device 200 which in turn may be referenced to navigated CT or MRI information. Accordingly, the guide device of FIG. 2A may be customized for a particular subject. Namely the apertures and/or features described herein may be customized for the particular subject based on his/her CT or MM information (e.g., subject anatomy) and/or based on the particular location where the guide device 200 is to be positioned. For example, aperture sizes (e.g., first access hole 216, second access hole 218), spaces between access holes (e.g., distance "d2"), and/or the like. More specifically, distance "d2" (FIG. 2B) may be a prescribed distance specific to a particular size of implants to be used (SAS implant, DVS implant, connector implant, and/or the like) and/or a desired anatomic location of the implant (e.g., aperture spacing to accommodate superior or posterior placement).

According to various aspects, the guide device 200 (e.g., the first access aperture 216, the second access aperture 218, and/or the like) may be configured to accept a pre-existing clutched drill (e.g., an Acra-Cut stepped drill bone perforator, robotically guided burrs, drill/burr bit, and/or the like). According to various aspects, guide device 200 (e.g., drilling/cutting guide) is configured to be adjustable or is designed for proper DVS and SAS access to defined positions (e.g., clinically-determined ideal positions) along the skull (e.g., anterior to posterior, superior to inferior, relatively near a midline of the skull). According to various aspects, once the guide device 200 is positioned in a desired orientation (e.g., anterior to posterior), the first access aperture 216 may be appropriately positioned over the subarachnoid space to drill a first burr hole (e.g., FIG. 3, inlet burr hole 302) and the second access aperture 218 may be appropriately positioned over the dural venous sinus (e.g., the sagittal sinus, the transverse sinus, and/or the like) to drill a second burr hole (e.g., FIG. 3, outlet burr hole 312). As depicted in FIG. 2B, according to various aspects, the green arrow depicts a flow of excess CSF from the SAS toward the guide device 200 and the blue arrow depicts a flow of the excess CSF from the guide device 200 to the DVS. The guide device 200 will ultimately be removed and replaced with an implant system, as described herein, to control these flows of excess CSF.

Figure 2C:
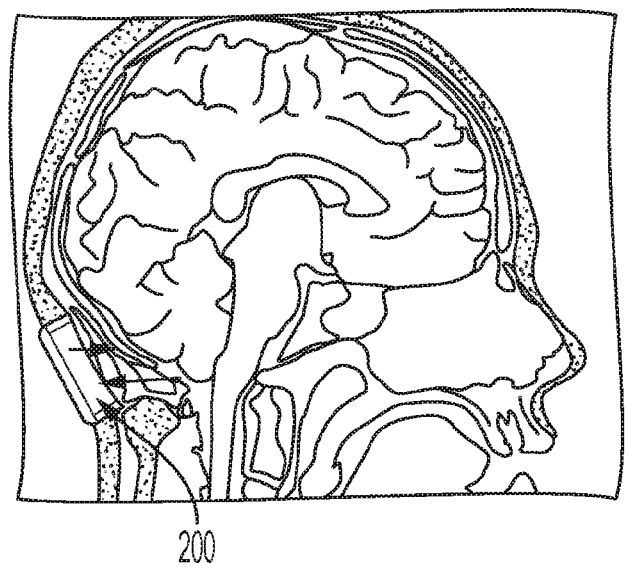
FIG. 2C depicts a sagittal view of the illustrative guide device of FIG. 2A, at the posterior placement location of FIG. 1, according to one or more embodiments shown and described herein.

FIG. 2C depicts an illustrative posterior placement of the guide device 200 according to one or more aspects of the present disclosure (e.g., Example 2 of FIG. 1). In light of FIG. 2C, the guide device 200 may be positioned in an anterior-posterior, a transverse, or an oblique orientation. According to various aspects the guide device 200 may be specifically configured for proper DVS and SAS access along the posterior skull. As depicted in FIG. 2C, according to various aspects, the green arrow depicts a flow of excess CSF from the SAS toward the guide device 200 and the blue arrow depicts a flow of the excess CSF from the guide device 200 to the DVS. Again, the guide device 200 will ultimately be removed and replaced with an implant system, as described herein, to control these flows of excess CSF.

Figure 3A:
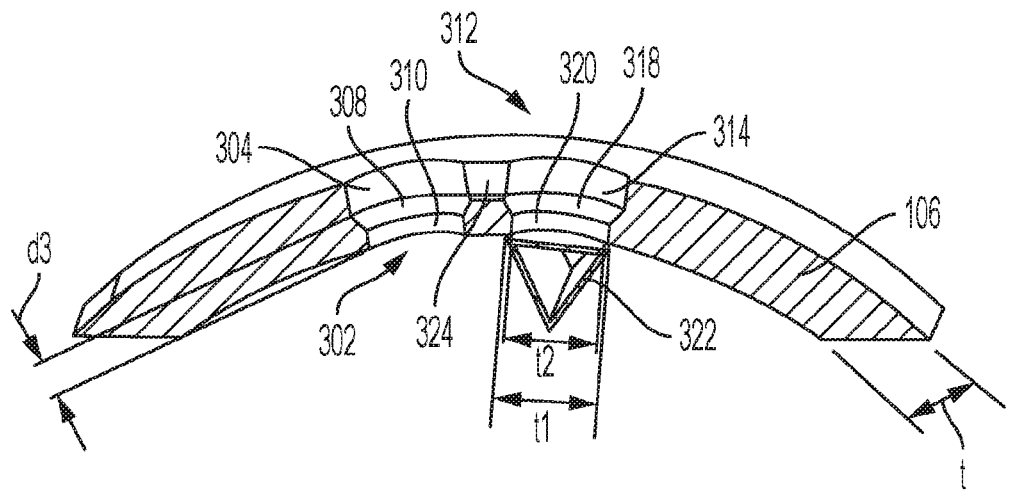
FIG. 3A depicts a cross-sectional view of an illustrative inlet burr hole and an illustrative outlet burr hole, as drilled in a subject's skull using the device of FIG. 2A, according to one or more embodiments shown and described herein.

FIG. 3A depicts an illustrative cross-section of burr holes 302, as drilled in a skull or cranium using the guide device 200 of FIG. 2A, according to one or more aspects of the present disclosure. In FIG. 3A, the guide device 200 has been removed for illustrative purposes. Referring to FIG. 3A, according to various aspects, an inlet burr hole 302 is defined by a first aperture portion 304, a second aperture portion 308, and a third aperture portion 310 through a thickness "t" of the skull 106. Similarly, according to various aspects, an outlet burr hole 312 is defined by a first aperture portion 314, a second aperture portion 318, and a third aperture portion 320 through the thickness "t" of the skull 106. According to various aspects, a diameter associated with the first aperture portions 304, 314 may be larger than a diameter associated with the third aperture portions 310, 320. In such an aspect, the second aperture portions 308, 318 gradually decrease in diameter from the diameter associated with the first aperture portions 304, 314 to the diameter associated with the third aperture portions 310, 320 thereby defining a taper or chamfer therebetween. Referring to FIG. 3A, such burr hole 302, 312 portions are defined within the thickness "t" a known distance from an interface between the skull bone and underlying dura. According to various aspects, a drill (e.g., a step drill designed to pop through the lower table/surface of the skull bone 106) may be used to drill the inlet burr hole 302 and the outlet burr hole 312 with such defined portions. In one example, third aperture portions 310, 320 may be a third diameter (e.g., about 11 mm) through a third part (e.g., about 2 mm) of the thickness "t" of the skull 106. Further in such an example, the first aperture portions 304, 314 may be a first diameter (e.g., about 14 mm) through a first variable part (e.g., about "X" mm) of the thickness "t" of the skull 106 (e.g., variable due to potential differences in thickness of a skull of the subject). Yet further in such an example, the second aperture portions 308, 318 may transition between the first diameter (e.g., about 14 mm) to the third diameter (e.g., about 11 mm) at a predefine angle (e.g., 45°) through a second part (e.g., about 2 mm-3 mm) of the thickness "t" of the skull 106. Overall, referring to FIG. 3A, a distance "d3" defined by the second part of the thickness "t" of the skull 106 and the third part of the thickness of the skull 106 is a controlled, predetermined distance. As described herein, various implant designs (e.g. SAS implants, DVS implants) take into account this controlled, predetermined distance "d3" (e.g., given the controlled, predetermined distance "d3", a DVS implant may be dimensioned to add a desired DVS surface depression distance). Furthermore, as described herein, various implant designs (e.g., SAS implants, DVS implants) mimic the second aperture portion 308, 318 to control advancement of the various implant design into the subject's skull 106 (e.g. avoids risk of advancing the various implant designs too far, avoids dura/brain/sinus damage, avoids bleeding, and/or the like).

Figure 3B:
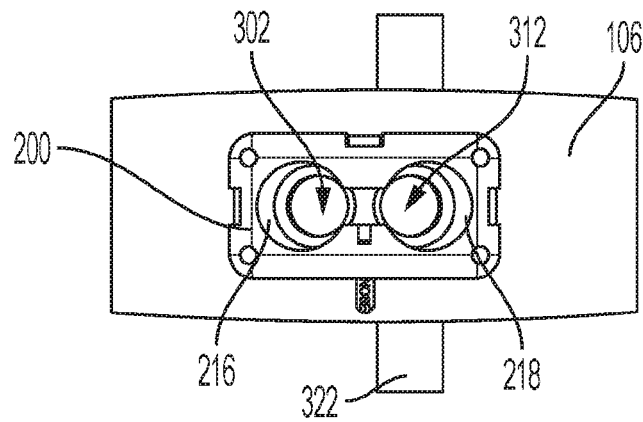
FIG. 3B depicts a top view of the illustrative guide device of FIG. 2A, as positioned on a subject's skull after drilling the outlet burr hole relative to the sinus and the inlet burr hole, according to one or more embodiments shown and described herein.
Figure 3C:
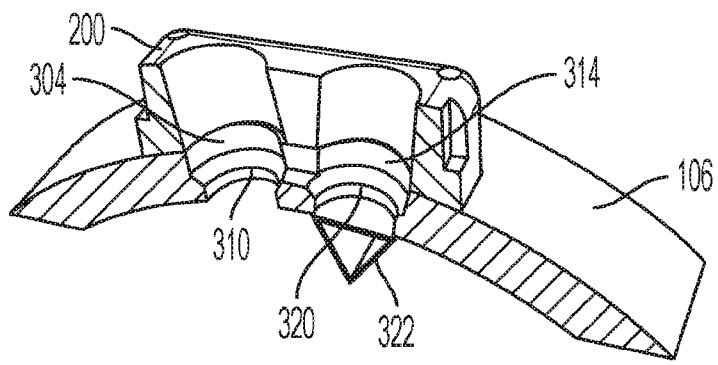
FIG. 3C depicts a cross-sectional view of the illustrative guide device of FIG. 2A, as positioned on the subject's skull after drilling the outlet burr hole relative to the sinus and the inlet burr hole, according to one or more embodiments shown and described herein.

FIG. 3B depicts an illustrative guide device 200 positioned on a skull 106 according to one or more embodiments of the present disclosure. As described herein, the guide device 200 may be placed/located on the skull 106 based on the identification of anatomic landmarks (e.g., the nasium, the DVS, a relative location of the SAS) and/or by navigated imaging. In light of FIG. 3B, after placement of the guide device 200 to guide the drill, the first aperture portions 304, 314 may be cut/drilled. According to one aspect, the first aperture portions 304, 314 may be cut/drilled via a series of cutting devices (e.g., drill bits) of progressively larger diameter (e.g., each using the previous hole as a pilot hole). According to various aspects a series of sleeves (not shown, e.g., with progressively larger inner diameters and the same outer diameter substantially equal to the first access aperture 216 and the second access aperture 218) may be placed in the first access aperture 216 and the second access aperture 218, respectively as holes are drilled progressively larger, to assist in keeping the first aperture portions 304, 314 of the burr holes 302, 312 centered. Notably, the second aperture portions 308, 318 may be defined by the tip of the last cutting device (e.g., drill/bur bit) used to define the first aperture portions 304, 314. Alternatively, the second aperture portions 308, 318 may be defined by a separate cutting device (e.g., a countersink drill bit and/or the like). According to various aspects it may be desired to drill the first aperture portions 304, 314 and the second aperture portions 308, 318 first to effectively remove skull bone drill shavings prior to exposing an internal portion of the subject's skull (e.g., underlying dura). According to various aspects, the third aperture portions 310, 320 may then be cut/drilled via a series of cutting devices of progressively larger diameter and/or a series of sleeves in a similar manner as described above to ultimately define the burr holes 302, 312. FIG. 3C depicts an illustrative cross-section of the guide device 200 placed on the skull 106 and drilled burr holes 302, 312 according to one or more embodiments of the present disclosure. In light of FIG. 3C, the sleeves, as described, may be further placed in the first aperture portions 304, 314 to assist in keeping the third aperture portions 310, 320 centered. According to other embodiments, the burr holes 302, 312 may be cut using a stepped drill (e.g., an Acra-Cut bone perforator w/clutch that stops upon break-through of the lower table of the skull) configured to drill the burr holes 302, 312 with the respective portions described herein.

Referring again to FIG. 3A-3C, the inlet burr hole 302 should be positioned over an available region of access to CSF in the SAS. According to various aspects, the available region is located a safe distance away from any peripheral veins. The outlet burr hole 312 should be positioned centrally over a portion of the DVS (e.g., the sagittal sinus (SS), the transverse sinus (TS), and/or the like). In view of FIG. 3A, the third aperture portion 320 of the outlet burr hole 312 may be marginally smaller (e.g., t1>t2) than the target portion of the DVS (e.g., represented by the triangular tube 322 in FIGS. 3A-3C). Referring briefly to FIG. 2B, the guide device 200 may be custom manufactured with a number widths "w" to accommodate a number of distances between the burr holes "d2", a number of angulations to the DVS and a number of different skull curvatures. According to further aspects, the guide device 200 may be further customized to accommodate a particular set of implants (e.g., SAS implants, DVS implants) configured to fit the burr holes 302, 312 and the portions thereof.

Figure 4:
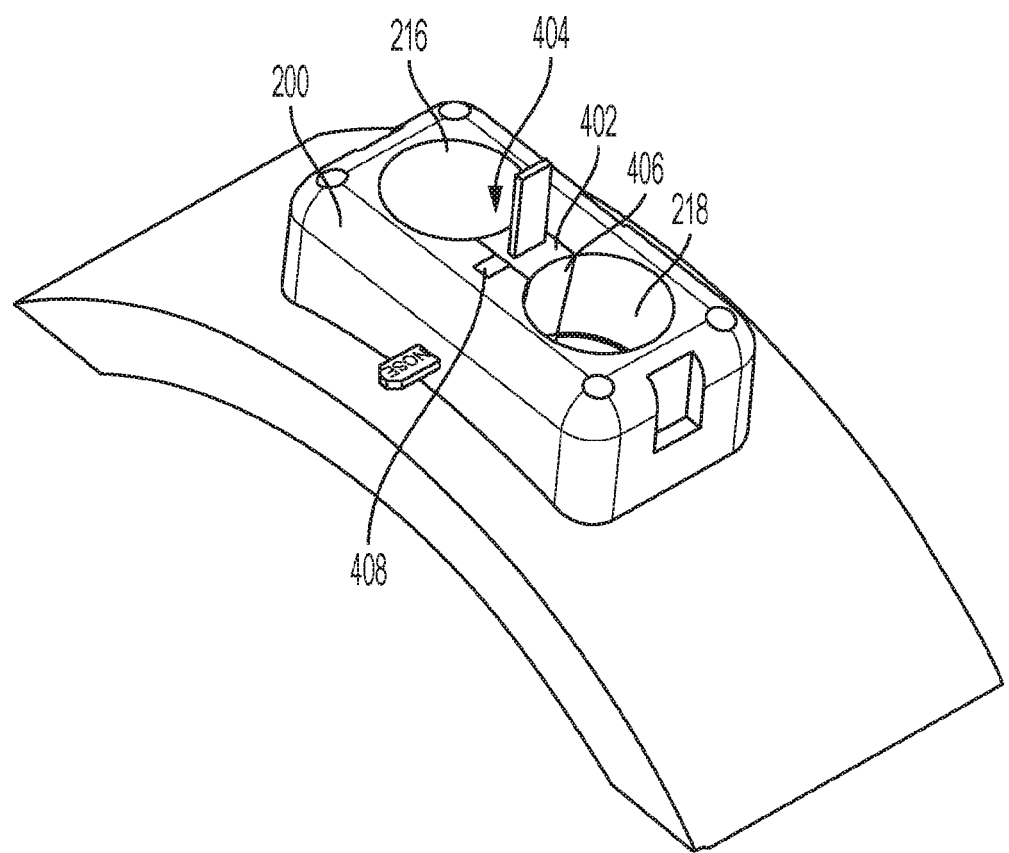
FIG. 4 depicts a perspective view of the illustrative guide device of FIG. 2A including an insertable/removable guide element to further guide the drilling of an inlet burr hole and an outlet burr hole, according to one or more embodiments shown and described herein.

FIG. 4 depicts an illustrative guide device 200 including an insertable/removable guide element 402 positioned between the first access aperture 216 and the second access aperture 218 within the connector space 223. The insertable/removable guide element may be sized to fit within the connector space 223. According to various aspects, opposing sides 404, 406 of the insertable/removable guide element 402 may be arcuate to complete the circumference of the first access aperture 216 and the second access aperture 218, respectively. Accordingly, the insertable/removable guide element 402 may form or define at least a portion of the first access aperture 216 and/or the second access aperture 218. In such aspects, the opposing sides 404, 406 of the insertable/removable guide element 402 may assist the first access aperture 216 and the second access aperture 218 in guiding the drill and/or the drill/burr bit when drilling the burr holes 302, 312 as described herein. The insertable/removable guide element 402 may be removed from the guide device 200 after the burr holes 302, 312 have been drilled. In addition, the insertable/removable guide element 402 may include a protrusion 408 shaped to slidably fit within the removable guide element aperture 224 (FIG. 2A) of the guide device 200. According to some aspects, the insertable/removable guide element 402 may facilitate burr bit control and/or the use of additional instruments when inserted. According to other aspects, the insertable/removable guide element 402 may facilitate the use of additional instruments when removed.

FIGS. 5A-5F depict illustrative DVS implant plug components of an implant system according to one or more aspects described herein. FIG. 5A depicts a DVS implant plug 502 according to various aspects of the present disclosure. The DVS implant plug 502 may include a plurality of selectable locations 516a, 516b, 516c in which a DVS outlet drain implant (e.g., FIG. 5F) may be inserted/positioned. Referring to FIG. 5B, if the outlet burr hole 312 is not centered over the sinus (e.g., depicted as the red triangular tube 322) such that location 516a is centered over the sinus, the outlet drain may be inserted/positioned at another location 516b, 516c that is centered over the sinus. According to various aspects, navigation may result in an outlet burr hole 312 plus or minus a first distance from an actual center of the sinus (e.g., plus or minus about 1 mm, plus or minus about 2 mm, and/or the like). In such an aspect, the DVS implant plug may be configured such that location 516b is a predetermined offset distance (e.g., about 1 mm, about 2 mm, and/or the like) in a first direction from location 516a and location 516c is a predetermined offset distance (e.g., about 1 mm, about 2 mm, and/or the like) in a second direction from location 516a. According to such aspects, the DVS implant plug 502 including the plurality of selectable locations 516a, 516b, 516c may prevent an outlet drain from being placed against a side wall of the sinus (e.g., due to the burr hole 312 not being centered) and/or rupturing the sinus wall (e.g., when testing sinus depth and/or inserting an outlet drain due to the burr hole 312 not being centered). In view of FIG. 5B, the DVS implant plug 502 may be sized and/or dimensioned to interferingly fit within the first aperture portion 314, the second aperture portion 318, and/or the third aperture portion 320 of the outlet burr hole 312 (FIG. 3A). Here, referring briefly to FIG. 5F, the shape and/or dimensions of the DVS implant plug 502 may mimic the outlet burr hole 312. According to some aspects the DVS implant plug 502 may be one piece. According to other aspects, the DVS implant plug may be more than one piece combined to define the size, shape and/or dimensions (e.g., to mimic the outlet burr hole 312). More specifically, the DVS implant plug 502 may include a first DVS implant portion 520 that corresponds to the first aperture portion 314, a second DVS implant portion 522 that corresponds to the second aperture portion 318, and a third DVS implant portion 524 that corresponds to the third aperture portion 320. According to various aspects, such a configuration (e.g., interface/interaction between the second DVS implant portion 522 and the second aperture portion 318 of the outlet burr hole 312) controls how deep the DVS implant plug 502 can be inserted. According to further aspects, such an interference fit may seal the DVS implant plug 502 to prevent bleeding and/or leaks. According to yet further aspects, referring again to FIG. 5A, a bottom surface 518 the DVS implant plug 502 may be coated with an adhesive or sealant and/or the adhesive or sealant may be placed within the outlet burr hole 312 prior to insertion of the DVS implant plug 502 (FIG. 5B). According to various aspects, the adhesive or sealant may include a fiber glue, a biocompatible adhesive, and/or the like. In such aspects, the adhesive or sealant may adhere the DVS implant plug 502 (e.g., temporarily or permanently) to the exposed dura (e.g., top layer of the sinus). Here, although the sinus is generally a tough membrane, it may be easily torn. A tear in the dura of the sinus is not desired because it may be difficult to stop the bleeding. Accordingly, adhering the DVS implant plug 505 to the dura effectively supports the dura to prevent and/or reduce the chances of a tear when piercing the dura to insert a drain outlet into the DVS implant plug. As such, the adhesive or sealant may further prevent bleeding, leaks, and/or tears. According to some aspects, the DVS implant plug 502 may include a flexible bottom lip seal 528. In view of FIG. 5F, the flexible bottom lip seal 528, upon insertion of the DVS implant plug 502, may push through the third aperture portion 320 to interface with the internal surface of the skull 106. According to other aspects, the flexible bottom lip seal 528 may be omitted (e.g., to minimize any interaction with and/or aggravation of the dura). The DVS implant plug 502 may further include a directional arrow 504 to orient during insertion. The directional arrow 504 may be pointed toward the nose of the subject. According to various aspects, the directional arrow 504 may be used to guide an inserted drain outlet in the proper orientation, as described herein.

FIG. 5C depicts another DVS implant plug 508 according to various aspects of the present disclosure. The DVS implant plug 508 may be configured and/or implanted similar to the DVS implant plug 502, as described herein, however the DVS implant plug 508 may include only one location 526 in which a DVS outlet drain implant (FIG. 5F) may be inserted/positioned. According to various embodiments, the DVS implant plug 508 may be rotatable prior to and/or after insertion within the outlet burr hole 312. In such aspects, if the outlet burr hole 312 is not centered over the sinus (e.g., depicted as the red triangular tube 322) the DVS implant plug 508 may be rotated to effectively offset location 526 any variable distance along an arcuate path to center the location 526 over a center of the sinus. The DVS implant plug 508 may further include a directional arrow 510 to orient during insertion (FIG. 5E, e.g., with a mark on the skull 506). In one example, the mark 506 on the skull 106 may be the initial orientation of the DVS implant plug 508 toward the subject's nose. If the DVS implant plug 508 is rotated (e.g., to center the location 526 over a center of the sinus), the directional arrow 510 may point "X" degrees off in a direction with respect to the mark 506. In such an aspect, when subsequently inserting the outlet drain at location 526, the outlet drain may be oriented "X" degrees in the opposite direction to properly orient the outlet drain parallel to the sinus at the center of the sinus.

Referring again to FIGS. 5A and 5C, each DVS implant plug 502, 508 may include a slit seal 512 to prevent unintentional drainage of venous blood and to provide a positive interlock with a connecting top implant component, as described herein. Referring to FIG. 5F, each DVS implant plug 502, 508 may utilize the tapered shelf design, as discussed herein, to fit securely into the outlet burr hole 312. Further, according to various aspects, each DVS implant plug 502, 508 may be secured with an adhesive or mechanically to the sinus membrane during implantation. As discussed herein, the DVS implant plug may be glued (e.g., via an adhesive or sealant) to the upper most portion of the DVS (e.g., dura) to stiffen the exposed sinus to reduce the chances of a tear during insertion of an outlet drain and/or to avoid bleeding or leaking during and/or after surgery. In addition, FIG. 5F depicts a side view of an example DVS outlet drain implant 514 (e.g., catheter) positioned generally against, upstream, and/or parallel to venous blood flow direction (e.g., arrow indicating venous blood flow as depicted in FIG. 5F). According to other aspects, the DVS outlet drain implant 514 may be positioned generally downstream, with, and/or parallel to the venous blood flow direction (not shown). The DVS outlet drain implant 514 may further include a slit/membrane seal 530 (e.g. silicone seal, and/or the like) to selectively permit blood flow and/or to allow instrument access.

Figure 6A:
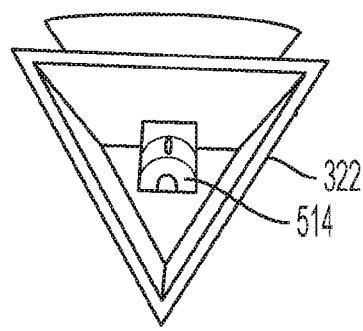
FIG. 6A depicts a front view of an illustrative DVS outlet drain implant centrally positioned within a sinus, according to one or more embodiments shown and described herein.
Figure 6B:
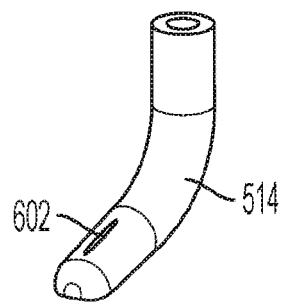
FIG. 6B depicts a perspective view of the illustrative DVS outlet drain implant of FIG. 6A including a slit valve, according to one or more embodiments shown and described herein.
Figure 6C:
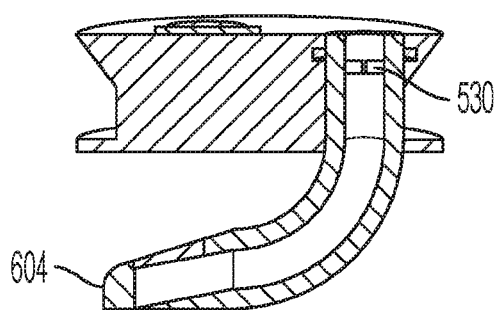
FIG. 6C depicts a cross-sectional view of the illustrative DVS outlet drain implant of FIG. 6A, including a membrane seal, according to one or more embodiments shown and described herein.

Referring now to FIG. 6A, according to various aspects, the DVS outlet drain implant 514 may be centrally located in the sinus (e.g., represented by the triangular tube 322) in all planes (e.g. each side of the triangular tube may be about 10 mm). Referring to FIG. 6B, the DVS outlet drain implant 514 may include an over-pressure slit valve 602 (e.g. pressure regulated) integral to the outlet drain to open to allow CSF flow at a specified pressure (e.g., 14 mm on a monometer). The over-pressure slit valve 602 would remain closed under the specified pressure. Referring to FIG. 6B, the over-pressure slit valve 602 may be located centrally relative to a longitudinal axis of the DVS outlet drain implant 514. Referring to FIG. 6C, the DVS outlet drain implant 514 may include a slit/membrane seal 530 designed to allow for a safe connection to other implant elements during surgery without blood loss. According to various aspects, the slit/membrane seal 530 may further allow instrument access to unclog an over-pressure slit valve 602 without having to remove the DVS outlet drain implant 514. According to other aspects, the slit/membrane seal 530 may further allow instrument access to test the over-pressure slit valve 602. For example, the DVS outlet drain implant 514 may be filled with a fluid (e.g., saline) to see if it is properly functioning. More specifically, the fluid may be pressurized to 30 mm on a manometer. In such an aspect, the fluid should continue to flow until the fluid is pressurized to 14 mm on the manometer (e.g. point at which the over-pressure slit valve 602 should close). If the flow continues past 14 mm on the manometer the over-pressure slit valve may be at least partially open and may need replaced. If the flow stops before 14 mm on the manometer (e.g., at 25 mm on the manometer), the over-pressure slit valve may be clogged and may need replaced. According to various aspects, given the modular nature of the various implants of the present implant system, a defective DVS outlet drain implant 514 may be replaced. Referring to the cross-section depicted in FIG. 6C, the outlet tip 604 may be shaped to minimize any coagulation of venous blood on the outlet tip 604. According to various aspects, the outlet tip 604 may be made of a material (e.g., anti-coagulation materials, nano-topographical features) to minimize any coagulation of venous blood on the outlet tip. According to further aspects, the outlet tip 604 may be shaped to minimize any dead area or pooling of blood flow. According to various aspects the outlet tip 604 may include an airfoil type tip shaped to minimize drag over the surface of the outlet tip 604. According to various aspects the outlet tip 604 may be shaped to maximize a velocity of blood flow over the surface of the outlet tip 604. According to various aspects, the outlet tip 604 may be shaped to enable uniform or laminar blood flow rather than turbulent blood flow over the surface of the outlet tip 604. According to various aspects, bioburden is minimized via a shape and overall size of the outlet tip 604. According to various aspects, the outlet tip includes a specifically designed pressure (e.g., low and high) regions. According to various aspects the outlet tip facilitates not only CSF outflow but also a lower dwell time of venous blood on the surface surrounding the over-pressure slit valve 602. According to such aspects, the outlet tip 604 may also prevent a backflow of blood from the dural venous sinuses to the other components of the implant system.

Referring to FIGS. 7A-7F, various outlet tips may be shaped to minimize any coagulation of venous blood on the outlet tip. According to various embodiments, the various outlet tips may be made of a material (e.g., anti-coagulation materials, nano-topographical features) to minimize any coagulation of venous blood on the outlet tip. According to various aspects, the outlet tip may include an airfoil type tip shaped to minimize drag and turbulence over the surface of the outlet in order to minimize coagulation of the blood on the surface of the outlet. According to various aspects, bioburden is minimized via a minimal shape and surface area. According to various aspects, the outlet tip may include a specifically designed high and low pressure regions on the surface. According to various aspects, the outlet tip facilitates not only CSF outflow but also a lower dwell time of venous blood on the surface surrounding an over-pressure slit valve (drain) portion. According to such aspects, the outlet tip prevents backflow of blood from the DVS to the other components of the implant system. Referring to FIG. 7F, an outlet tip may incorporate a slit valve system 702 to release CSF into the DVS at a predetermined pressure differential, as discussed herein.

Figure 8A:
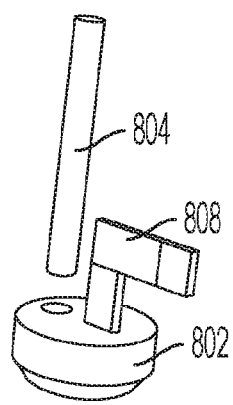
FIG. 8A depicts a perspective view of an illustrative DVS positioning system to center a DVS outlet drain implant over a deepest portion of the sinus, according to one or more embodiments shown and described herein.
Figure 8B:
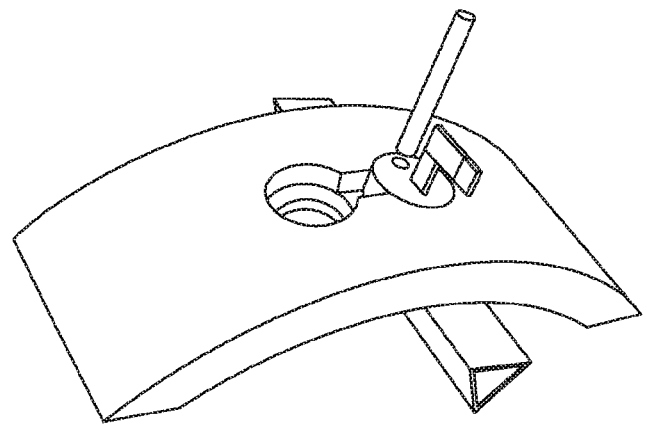
FIG. 8B depicts a perspective view of the illustrative DVS positioning system of FIG. 8A in a non-rotated position, according to one or more embodiments shown and described herein.
Figure 8C:
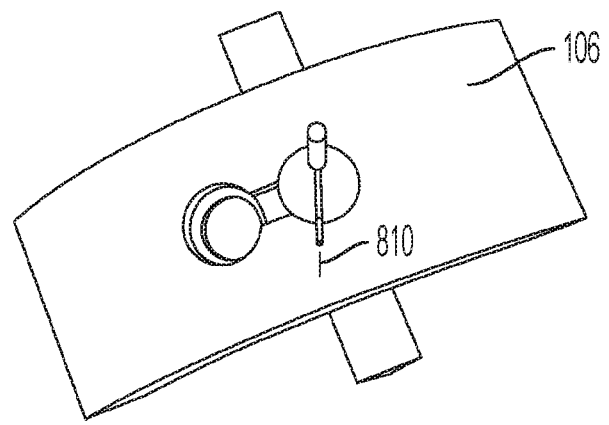
FIG. 8C depicts a top view of the illustrative DVS positioning system of FIG. 8A in a rotated position, according to one or more embodiments shown and described herein.

FIGS. 8A-8C depict a dural venous sinus-navigated DVS outlet drain implant positioning system. According to various aspects, the DVS outlet drain implant may be adjustable in rotation (eccentric) (e.g., FIG. 8C) to place the DVS outlet drain implant location on dural venous sinus (e.g., sagittal sinus, transverse sinus, and/or the like) based on navigation adjustment or surgeon preference in determination of sinus centerline/midline (e.g., to the direction of sinus flow) at maximum/deepest sinus depth (e.g. to fine-tune placement such that the DVS outlet drain implant is centered over the deepest portion of the sinus). FIG. 8A depicts a DVS positioning system including a temporary DVS implant plug 802, a navigation marker 804, and a flag 808. According to various aspects, the temporary DVS implant plug 802 may be used to determine any side-to-side offset (e.g., plus or minus 2 mm from an initial centerline/midline position) required to center the DVS outlet drain implant in a center of the DVS. According to various aspects, the flag 808 may removably couple to a directional arrow (e.g., FIG. 5C, directional arrow 510) of the temporary DVS implant plug 802. FIG. 8B depicts the DVS positioning system before adjustment. FIG. 8C depicts the DVS positioning system after a medial-lateral adjustment. Referring to FIG. 8C, a position 810 of the flag 808 may be marked on skull bone 106 after navigated positioning of an ideal DVS outlet drain direction (e.g., pointed downstream or with venous blood flow, pointed upstream or against venous blood flow, across the venous blood flow, at a tapered angle with respect to the venous blood flow, and/or the like).

FIGS. 9A-9D depict DVS outlet drain implant positioning with the temporary DVS implant plug 802, the navigation marker 804 and the flag 808 (e.g., of FIGS. 8A-8C) removed. In line with FIG. 8C, FIGS. 9A and 9C illustrate the flag position on navigated component as marked on the skull bone 106. Referring to FIG. 9A, the red directional arrow of the DVS implant plug 902 may be aligned with the mark 810 on the skull bone 106. Such an alignment ensures that the DVS outlet drain implant 904 will be located at a center of the DVS. FIG. 9C depicts the DVS outlet drain implant 904 (catheter) in position with the DVS implant plug 902 removed. Referring to FIGS. 9A and 9C, the inlet hole may be in the same position on the DVS implant plug 902 as the hole position on the navigation piece (e.g. temporary DVS implant plug 802). Referring to FIGS. 9B and 9D, the DVS outlet drain implant 904 may be inserted towards the nasium, or other visible or imaged anatomic landmark (e.g., against blood flow). More specifically, referring to FIG. 9D, the DVS outlet drain implant 904 may be rotated by a same degree as the flag 808 in the opposite direction to ensure that the DVS outlet drain implant 904 is positioned parallel to the DVS at the center of the DVS.

Figure 10A:
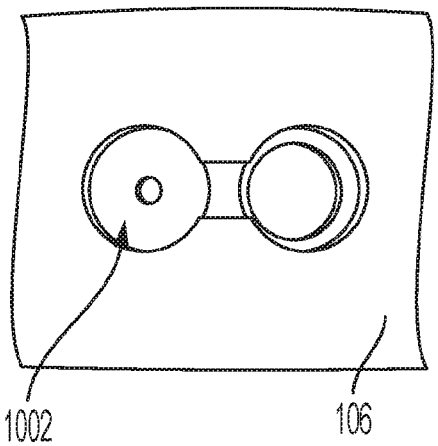
FIG. 10A depicts a top view of an illustrative SAS implant plug within the inlet burr hole of the subject's skull, according to one or more embodiments shown and described herein.
Figure 10B:
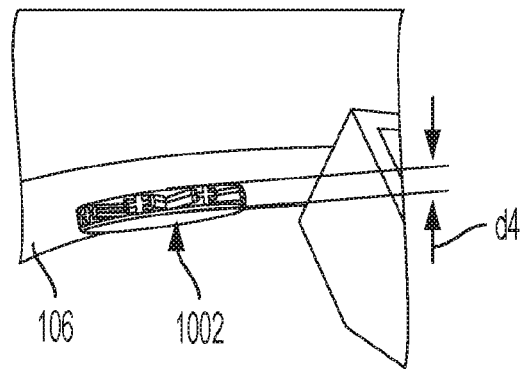
FIG. 10B depicts a bottom perspective view of the illustrative SAS implant plug of FIG. 10A within the inlet burr hole of the subject's skull, according to one or more embodiments shown and described herein.

FIGS. 10A-10H depict illustrative subarachnoid space (SAS) implant plugs (e.g., CSF inlet components) according to various aspects of the present disclosure. FIGS. 10A and 10B depict an SAS implant plug 1002 as positioned (e.g., superior positioned SAS CSF drain) in the inlet burr hole 302 (FIG. 3A). The SAS implant plug 1002 may be sized and/or dimensioned to interferingly fit within the first aperture portion 304, the second aperture portion 308, and/or the third aperture portion 310 of the inlet burr hole 302 (FIG. 3A). Here, referring to FIG. 10C, the shape and/or dimensions of the SAS implant plug 1002 may mimic the inlet burr hole 302. According to some aspects the SAS implant plug 1002 may be one piece. According to other aspects, the SAS implant plug may be more than one piece combined to define the size, shape and/or dimensions (e.g., to mimic the inlet burr hole 302). More specifically, the SAS implant plug 1002 may include a first SAS implant portion 1004 that corresponds to the first aperture portion 304, a second SAS implant portion 1006 that corresponds to the second aperture portion 308, and a third SAS implant portion 1008 that corresponds to the third aperture portion 310. According to various aspects, such an interference fit may seal the SAS implant portion 1002 to prevent bleeding and/or leaks. According to a further aspect, an adhesive or sealant (temporary or permanent) may be used. According to various aspects, such a configuration (e.g., interface/interaction between the second SAS implant portion 1002 and the second aperture portion 308 of the inlet burr hole 302) controls how deep the SAS implant plug 1002 can be inserted. In this vein, referring to FIG. 10B in view of FIG. 10C, a fourth SAS implant portion 1010 may protrude below a bottom surface of the skull 106 a predetermined depth "d4". According to various aspects, the fourth SAS implant portion 1010 may controllably depress a surface of the brain to a controlled or fixed depth (e.g. "d4") if depression of the surface of the brain would occur at the location of the inlet burr hole 302. For example, "d4" may be less than 5 mm. As another example, "d4" may be less than 2 mm. As another example, "d4" may be customized for a subject (e.g., 0.5 mm for a pediatric subject). Such a feature may avoid ad hoc depression of the brain with a tool (e.g., spatula and/or the like) and avoid potential brain and/or dura injury or bleeding. Such a feature may be instrumental if the brain is under high pressure and is exuding or herniating up into the inlet burr hole 302. In such an aspect, the SAS implant plug 1002, including the fourth SAS portion 1010 to control depression, may be used to efficiently depress the brain while minimizing trauma and/or inflammation of the brain.

Figure 10C:
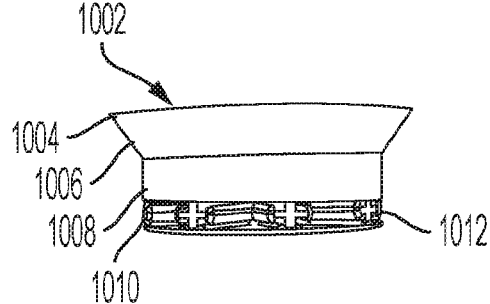
FIG. 10C depicts a side view of the illustrative SAS implant plug of FIG. 10A before insertion within the inlet burr hole of the subject's skull, according to one or more embodiments shown and described herein.
Figure 10D:
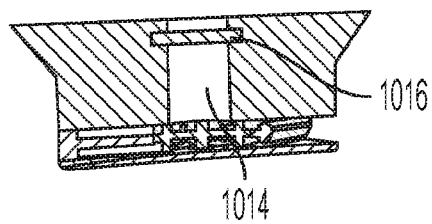
FIG. 10D depicts a cross-sectional view of the illustrative SAS implant plug of FIG. 10C, according to one or more embodiments shown and described herein.

Further in view of FIGS. 10C and 10D, excess CSF may be channeled via cruciform shaped SAS inlet drains 1012 around the SAS implant plug 1002 (e.g., similar to a blake drain, less than 5 mm OD) to a central portion 1014 for passage via a connector implant (e.g., FIGS. 14A-14C) and ultimately to a DVS outlet drain implant According to various aspects, numerous SAS inlet drains 1012 around the SAS implant plug 1002 permit CSF fluid access despite one or more SAS inlet drains 1012 being clogged/blocked. In view of FIG. 10D, a top portion of the SAS implant plug 1002 may include a slit seal 1016 to prevent unintentional drainage of CSF and to provide a positive interlock with the connector implant. According to various aspects, after drilling the inlet burr hole 302, an incision may be made in the dura to creates a dura tissue flap (e.g., about 11 mm in diameter to correspond with the fourth SAS implant portion 1010), and the SAS implant plug 1002 may be placed through that incision into the subarachnoid space (SAS) to be in fluid communication with the CSF. According to various aspects, the dura tissue flap may be partially or fully retracted or removed during and/or after insertion to allow the SAS implant plug 1002 full access to the subarachnoid space (SAS).

Figure 10E:
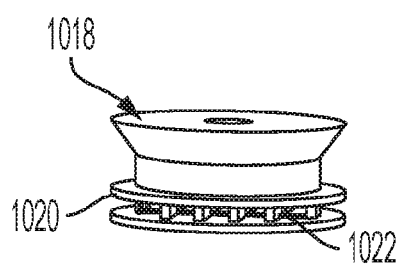
FIG. 10E depicts a perspective view of an illustrative SAS implant plug including a lip seal, according to one or more embodiments shown and described herein.
Figure 10F:
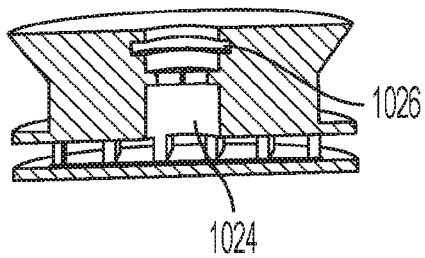
FIG. 10F depicts a cross-sectional view of the illustrative SAS implant plug of FIG. 10E, according to one or more embodiments shown and described herein.

Referring to FIGS. 10E and 10F, according to some aspects, another SAS implant plug 1018 may include a flexible bottom lip seal 1020. Similar to as discussed herein (e.g., FIG. 5F), the flexible bottom lip seal 1020, upon insertion of the SAS implant plug 1018, may push through the third aperture portion 310 of the inlet burr hole 302 to interface with the internal surface of the skull 106 (e.g., to further secure and/or seal the SAS implant plug 1018). According to other aspects, the flexible bottom lip seal 1020 may be omitted (e.g., to minimize any interaction with and/or aggravation of the dura). In view of FIGS. 10E and 10F, excess CSF may be channeled via grate SAS inlet drains 1022 around the SAS implant plug 1018 to a central portion 1024 for passage via a connector implant (e.g., FIGS. 14A-14C) and ultimately to a DVS outlet drain implant. According to various aspects, numerous SAS inlet drains 1022 around the SAS implant plug 1018 permit CSF fluid access despite one or more SAS inlet drains 1022 being clogged/blocked. In view of FIG. 10F, a top portion of the SAS implant plug 1018 may include slit/membrane seal 1026 to prevent unintentional drainage of CSF and to provide a positive interlock with the connector implant.

Figure 10G:
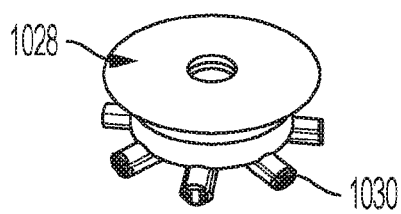
FIG. 10G depicts a perspective view of an illustrative SAS implant plug including a plurality of axially protruding drains, according to one or more embodiments shown and described herein.
Figure 10H:
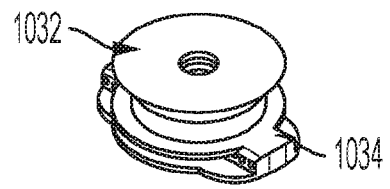
FIG. 10H depicts a perspective view of an illustrative SAS implant plug including a combined lip seal and a plurality of axially protruding drains, according to one or more embodiments shown and described herein.

FIGS. 10G and 10H depict further SAS implant plugs 1028, 1032 similar to those described herein. FIG. 10G depicts an SAS implant plug 1028 including axially protruding channels/drains 1030 (e.g., similar to a blake drain) and FIG. 10F depicts an SAS implant plug 1032 including a protruding drain channel 1034 (e.g., including a plurality of side holes that drain into a central channel to drain into a central portion of the SAS implant plug 1032). According to various aspects, the channels 1030, 1034 may protrude past a third SAS implant portion (that corresponds to the third aperture portion 310 of the inlet burr hole 302) to function similar to a flexible lip seal (e.g., FIG. 10E, flexible lip seal 1020) to secure and/or seal the SAS implant plug 1028, 1032 (e.g. below the skull, under the dura to be in fluid communication with the CSF). According to various aspects, the channels 1030, 1034 may not protrude past the third SAS implant portion to minimize any interaction with and/or aggravation of the dura. Overall, FIGS. 10A-10H depict various aspects where a SAS inlet drain(s) is integral to the SAS implant plug (e.g. for CSF drainage local to the SAS implant plug). According to an alternative aspect, the various SAS inlet drain portions (as described herein) may be a separate SAS inlet drain implant that it coupled to the SAS implant plug portions of FIGS. 10A-10H.

Figure 11A:
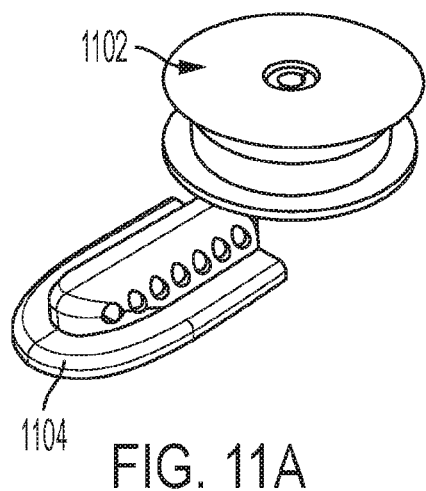
FIG. 11A depicts a perspective view of an illustrative SAS inlet drain implant coupled to an SAS implant plug, according to one or more embodiments shown and described herein.
Figure 11B:
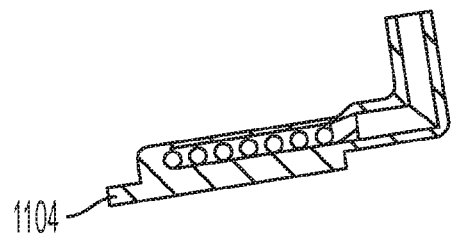
FIG. 11B depicts a cross-sectional view of the illustrative SAS inlet drain implant of FIG. 11A, according to one or more embodiments shown and described herein.
Figure 11C:
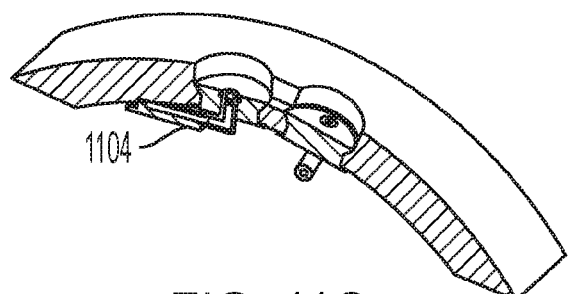
FIG. 11C depicts a perspective cross-sectional view of the illustrative SAS inlet drain implant and SAS implant plug of FIG. 11A within the inlet burr hole of a subject's skull, according to one or more embodiments shown and described herein.
Figure 11D:
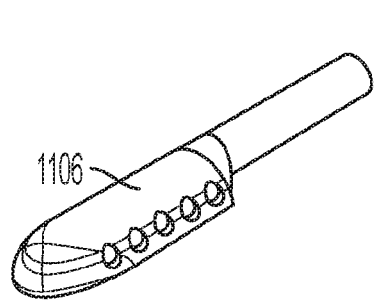
FIG. 11D depicts a perspective view of an illustrative SAS inlet drain implant coupleable to an SAS implant plug, according to one or more embodiments shown and described herein.
Figure 11E:
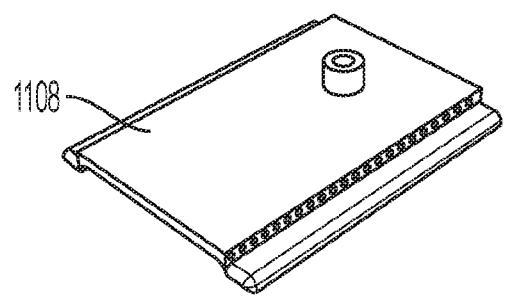
FIG. 11E depicts a perspective view of an illustrative SAS inlet drain implant coupleable to an SAS implant plug, according to one or more embodiments shown and described herein.
Figure 11F:
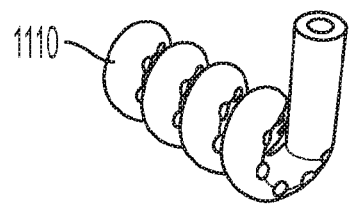
FIG. 11F depicts a perspective view of an illustrative SAS inlet drain implant coupleable to an SAS implant plug, according to one or more embodiments shown and described herein.

FIGS. 11A-11F depict illustrative SAS inlet drain implants (e.g., CSF inlet components). In view of FIGS. 11A-11F, CSF inlet holes of the various SAS inlet drain implants may be positioned a predetermined distance from the SAS implant plugs (e.g., SAS implant plug 1102). According to various aspects, the predetermined distance may be a distance to place the CSF inlet holes in fluid communication with the CSF of the subarachnoid space. FIGS. 11A-11C depict an SAS inlet drain implant 1104, FIG. 11D depicts another SAS inlet drain implant 1106, FIG. 11E depicts yet another SAS inlet drain implant 1108, and FIG. 11F depicts a further SAS inlet drain implant 1110. While FIGS. 11A-11E depict a generally planar SAS inlet drain implant, FIG. 11F illustrates a generally elongate SAS inlet drain implant without being planar. According to various aspects, such SAS inlet drain implants 1104, 1106, 1108, 1110 may be placed through the incision in dura (e.g., dura tissue flap) and tunneled under the dura to a cistern (e.g., a cerebellomedullary cistern, or the like) or some other area of the subarachnoid space some distance away from the inlet burr hole (FIG. 3A, inlet burr hole 302). According to various aspects, inflammation may be present post-procedure near the inlet burr hole 302 due to healing bone and/or dura. Placing the CSF inlet holes a distance away from such inflammation (e.g., via the SAS inlet drain implants 1104, 1106, 1108, 1110) may avoid a blockage of the CSF inlet holes due to such inflammation. Overall, FIGS. 11A-11F depict various SAS inlet drain implants configured as a separate component that may be coupled to a SAS implant plug as described herein.

Figure 12A:
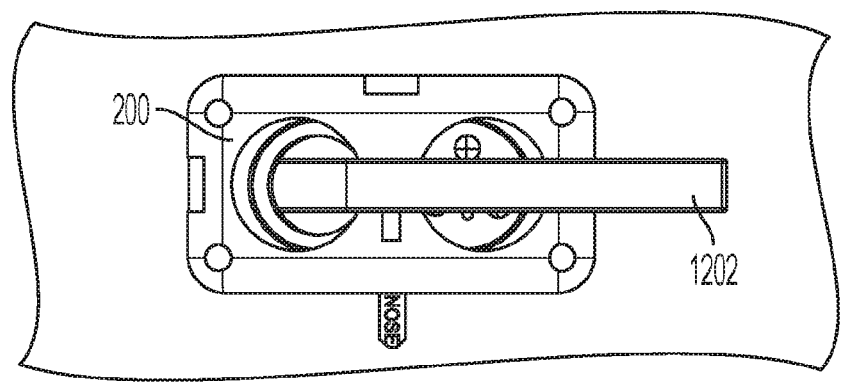
FIG. 12A depicts a top view of an illustrative SAS implant instrument relative to the guide device of FIG. 2A to deploy or install a SAS inlet drain implant, according to one or more embodiments shown and described herein.
Figure 12B:
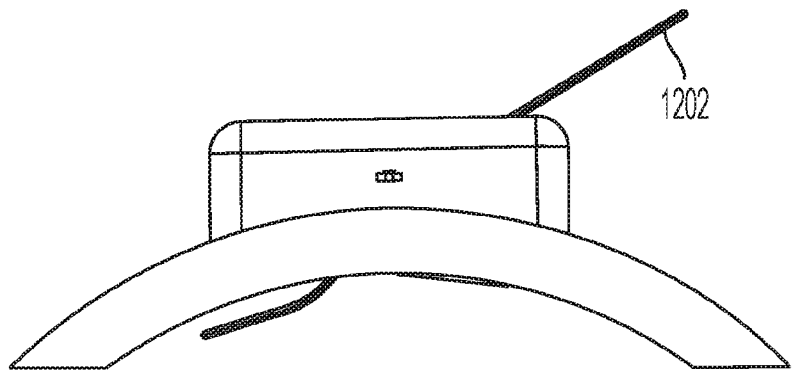
FIG. 12B depicts a side view of the illustrative SAS implant instrument and guide device of FIG. 12A, according to one or more embodiments shown and described herein.
Figure 12C:
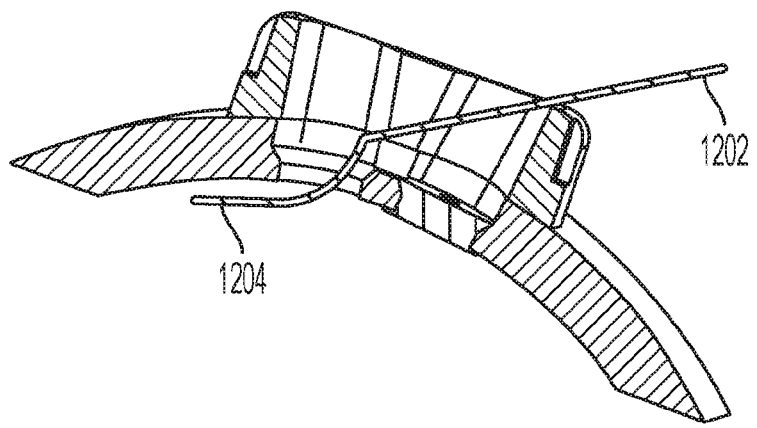
FIG. 12C depicts a cross-sectional view of the illustrative SAS implant instrument and guide device of FIG. 12B, according to one or more embodiments shown and described herein.

FIGS. 12A-12C depict an illustrative SAS implant instrument usable to deploy, deliver or install a SAS inlet drain implant (e.g., FIGS. 11A-11F) according to various aspects of the present disclosure. Referring to FIG. 12C, a bottom portion 1204 of an SAS implant instrument 1202 may be used to depress a brain surface away from the dura at a predetermined location. In view of FIGS. 12A-12C, according to various aspects, the device 200 may be configured and the SAS implant instrument 1202 may be sized and/or shaped to guide the SAS implant instrument 1202 while depressing the brain surface to a controlled depth. According to such aspects, the SAS implant instrument and/or the SAS inlet drain implants may be placed (e.g., via a navigation-guided needle, removable after placement) through an incision in the dura (e.g., dura tissue flap). A SAS implant plug 1102 (FIG. 11A) may then be coupled to the inserted SAS inlet drain implant after proper placement and/or orientation of the SAS inlet drain implant via the SAS implant instrument 1202. According to various aspects, the dura tissue flap may be partially or fully displaced or retracted during and/or after insertion to allow portions of the SAS inlet drain implant full access to the subarachnoid space (SAS). Overall, the SAS implant instrument 1202 is configured to accurately position a direction of the remotely positioned CSF inlet holes of the various SAS inlet drain implants described herein as well as ensure that a space between the dura and the brain is safely and controllably made, to a correct depth and length, to fully and appropriately accommodate the SAS inlet drain implant being inserted.

Figure 13A:
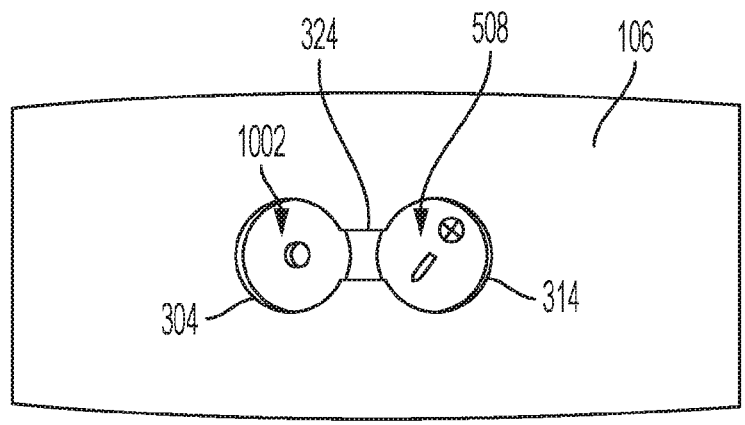
FIG. 13A depicts a top view of a SAS implant plug positioned within an inlet burr hole and a DVS implant plug positioned within an outlet burr hole of a subject's skull, according to one or more embodiments shown and described herein.
Figure 13B:
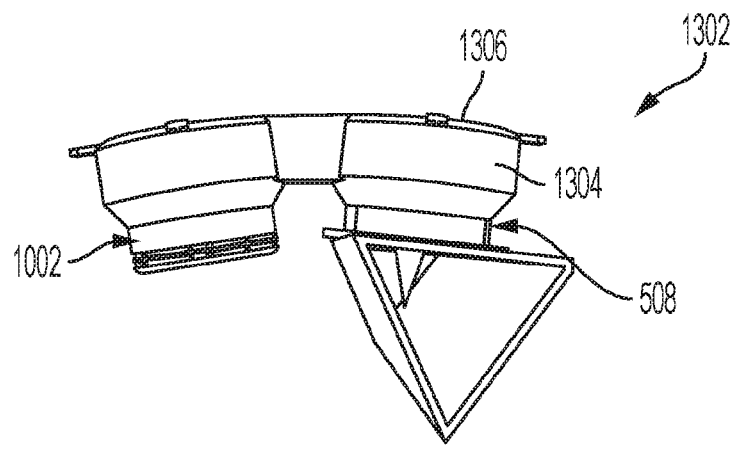
FIG. 13B depicts a side view of an illustrative CSF drain system relative to the sinus, according to one or more embodiments shown and described herein.
Figure 13C:
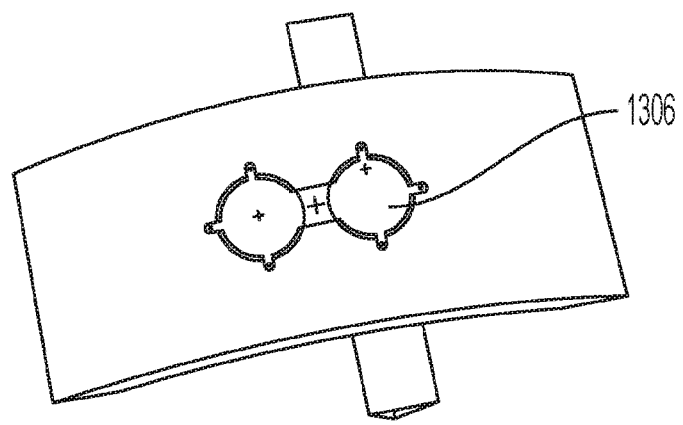
FIG. 13C depicts a top perspective view of the illustrative CSF drain system positioned within the subject's skull, according to one or more embodiments shown and described herein.

FIGS. 13A-13C depict a connector implant 1302 of the modular implant system (e.g., CSF drain system) according to various aspects of the present disclosure. In view of FIG. 13A, the guide device 200 has been removed from the subject's skull. FIG. 13B depicts a side view of the connector implant 1302 which may include a connector plug element 1304 and a connector cap 1306. According to various aspects, the connector plug element 1304 may couple (e.g., mechanically snap and/or the like) to the SAS implant plug 1002 and/or the DVS implant plug 508. More specifically, referring briefly to FIG. 14C a bottom surface of the connector plug element 1304 may include a SAS protrusion 1314 and/or a DVS protrusion 1316 configured to interlock (e.g., a positive locking, sealed connection, a Luer taper, and/or the like) with the SAS implant plug and the DVS implant plug, respectively. According to various aspects, the connector implant 1302 may be configured (e.g., as described herein) to fluidly couple a SAS implant plug 1002 and its corresponding SAS inlet drain implant to a DVS implant plug 508 and its corresponding DVS outlet drain implant. According to other aspects, the connector plug element 1304 may be omitted. In such an aspect, the negative space cut and/or drilled in the patient's skull (e.g., via the guide device 200 described herein) may function in a manner similar to the connector plug element 1304 to fluidly couple (e.g., as described herein) the SAS implant plug 1002 and its corresponding SAS inlet drain implant to a DVS implant plug 508 and its corresponding DVS outlet drain implant. Further in such an aspect, the connector cap 2604 may couple (e.g. screws and/or the like) directly to the subject's skull 106 (FIG. 13C).

Still referring to FIGS. 13A-13C, FIG. 13A depicts a DVS implant plug 508 (FIG. 5C) implanted within the outlet burr hole 312 (FIG. 3A) and a SAS implant plug 1002 (FIG. 10C) implanted within the inlet burr hole 302 (FIG. 3A) of a subject's skull 106. FIG. 13B depicts a connector plug element 1304 configured to couple the SAS implant plug 1002 to the DVS implant plug 508. Referring to FIG. 13B in view of FIG. 13A, the connector plug element 1304 of the connector implant 1302 may be shaped and/or sized to interferingly fit within the first aperture portion 304 of the inlet burr hole 302, the first aperture portion 314 of the outlet burr hole 312, and the connecting channel 324 (FIG. 3A, e.g., defined in the skull 106 between the first aperture portion 304 of the inlet burr hole 302 and the first aperture portion 314 of the outlet burr hole 312). According to some aspects, an adhesive may be used to secure the connector plug element 1304 to the subject's skull.

Figure 14A:
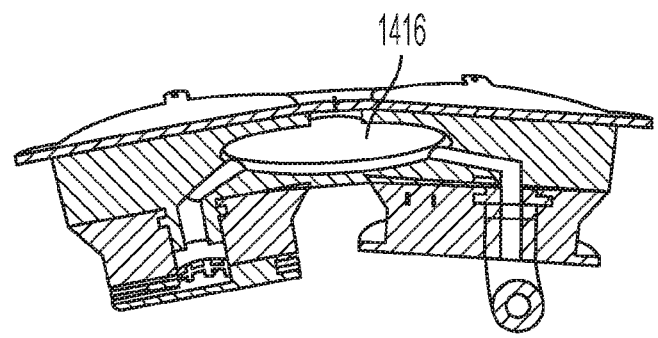
FIG. 14A depicts a cross-sectional view of a CSF drain system, according to one or more embodiments shown and described herein.
Figure 14B:
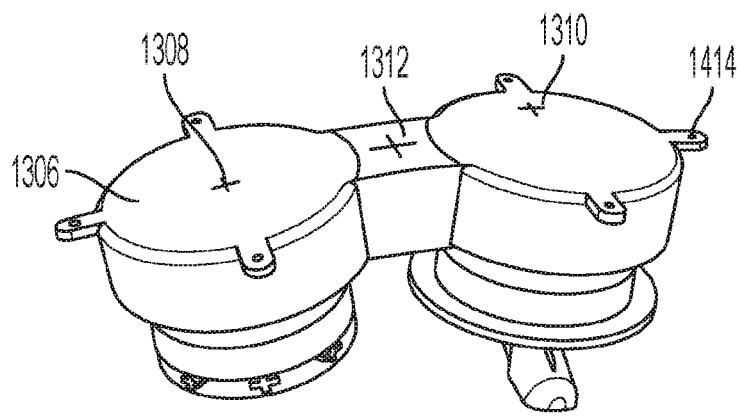
FIG. 14B depicts a perspective view of the CSF drain system of FIG. 14A, according to one or more embodiments shown and described herein.
Figure 14C:
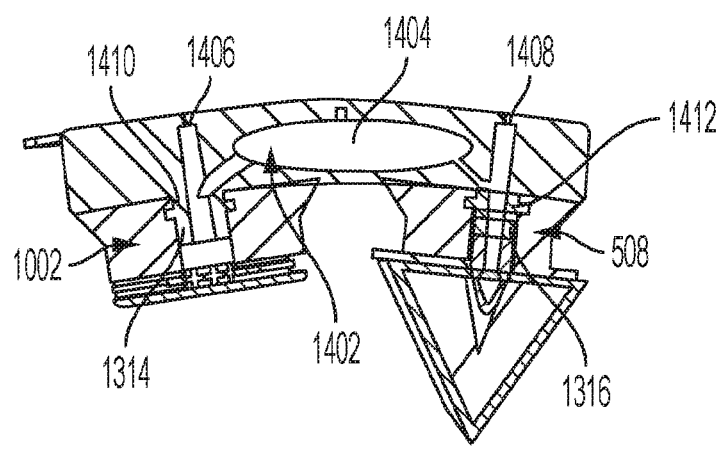
FIG. 14C depicts a cross-sectional view of a CSF drain system, according to one or more embodiments shown and described herein.

According to various aspects, the connector implant 1302 may fluidly couple the SAS implant plug 1002 and its corresponding SAS inlet drain implant to a DVS implant plug 508 and its corresponding DVS outlet drain implant via a reservoir and access port implant. FIGS. 14A-14C depict illustrative various reservoir and access port implants according to aspects of the present disclosure.

Figure 24A:
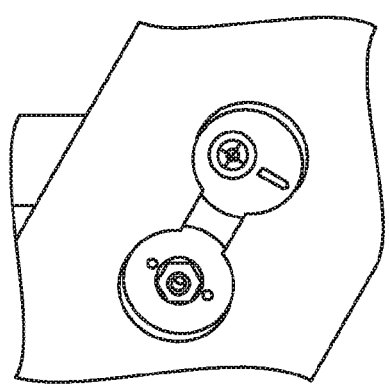
FIG. 24A depicts a top view of an illustrative SAS implant plug and DVS implant plug in position on a subject's skull, according to one or more embodiments shown and described herein.
Figure 24B:
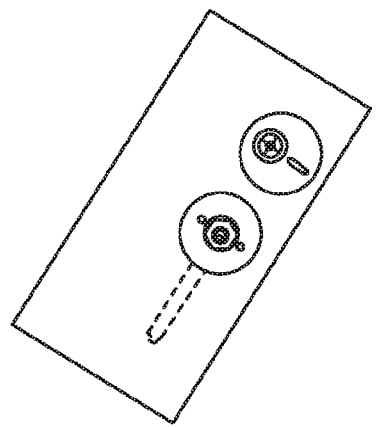
FIG. 24B depicts a top view of an illustrative SAS implant plug including an SAS inlet drain and DVS implant plug in position on a subject's skull, according to one or more embodiments shown and described herein.
Figure 24C:
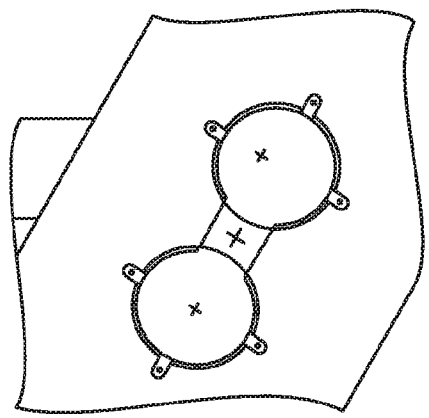
FIG. 24C depicts a top view of a connector cap of an implant system, according to one or more embodiments shown and described herein.
Figure 24E:
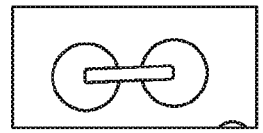
FIG. 24E depicts a top view of an illustrative SAS implant plug fluidly coupled to a DVS implant plug via a catheter, according to one or more embodiments shown and described herein.
Figure 24D:
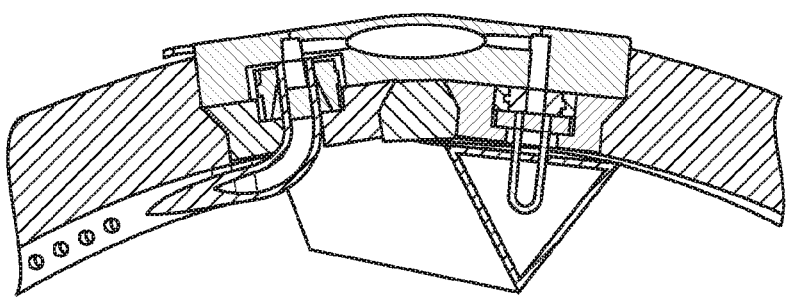
FIG. 24D depicts a cross-sectional view of an illustrative implant system positioned within a subject's skull, according to one or more embodiments shown and described herein.

Referring to FIG. 14C, a reservoir and access port implant 1402 may fluidly couple the SAS implant plug 1002 to the DVS implant plug 508 (See also FIG. 24D). More specifically, the reservoir and access port implant 1402 may include a reservoir 1404, a SAS implant access port 1406 (e.g., inserted through slit/membrane seal 1026), and a DVS implant access port 1408 (e.g., inserted through slit/membrane seal 530). In this vein, referring to FIG. 14B, the connector cap 1306 of the connector implant 1302 may include at least two direct access points 1308, 1310 and one general access point 1312. In this vein, referring again to FIG. 14C, the SAS implant access port 1406 may be accessed, via direct access point 1308, to directly access the inlet components (e.g., SAS implant components) and the DVS implant access port 1408 may be accessed, via direct access point 1310, to directly access the outlet components (DVS implant components). According to various aspects, direct access may permit pressure testing, flow testing, and blockage testing (e.g., via manometer as described herein), and the addition of medications without having to remove the connector cap 1306 and/or other implant system components. Similarly, in view of FIG. 14C, the reservoir 1404 may be accessed, via general access point 1312, to generally access the inlet components and/or the outlet components. According to various aspects, general access may permit pressure testing, flow testing, blockage testing, and the addition of medications without having to remove the connector cap 1306 and/or other implant system components. According to other aspects, general access to the reservoir 1404 may permit the removal of CSF for analysis as well as the purging of air from the implant system before completing the CSF fluid circuit. According to another aspect, the reservoir and access port implant 1402 may similarly fluidly couple the SAS implant plug 1002 to the DVS implant plug 508 and provide similar access when the connector plug element 1304 is omitted.

Still referring to FIG. 14C, reservoir and access port implant 1402 may connect securely to both the SAS implant plug 1002 and the DVS implant plug 508. More specifically, the SAS implant access port 1406 may connect securely to the SAS implant plug 1002 via a mechanical interlock 1410 and the DVS implant access port may connect securely to the DVS implant plug 508 via a mechanical interlock 1412 (e.g., a Luer taper, and/or the like). Viewing FIG. 14B in light of FIG. 13C, the connector cap 1306 may be secured to the subject's skull via attachment components (e.g., screws and/or the like) at apertures 1414 defined in the connector cap 1306. FIG. 14A depicts a reservoir and access port implant 1416 according to another aspect of the present disclosure. In such an aspect, the reservoir and access port implant 1416 may lack an SAS implant access port and/or a DVS implant access port but may otherwise functions in a manner similar to the reservoir and access port implant 1402 described herein. According to another aspect, the reservoir and access port implant 1402, 1416 may be replaced by a catheter (e.g., FIG. 24E) if access is not desired.

Figure 15:
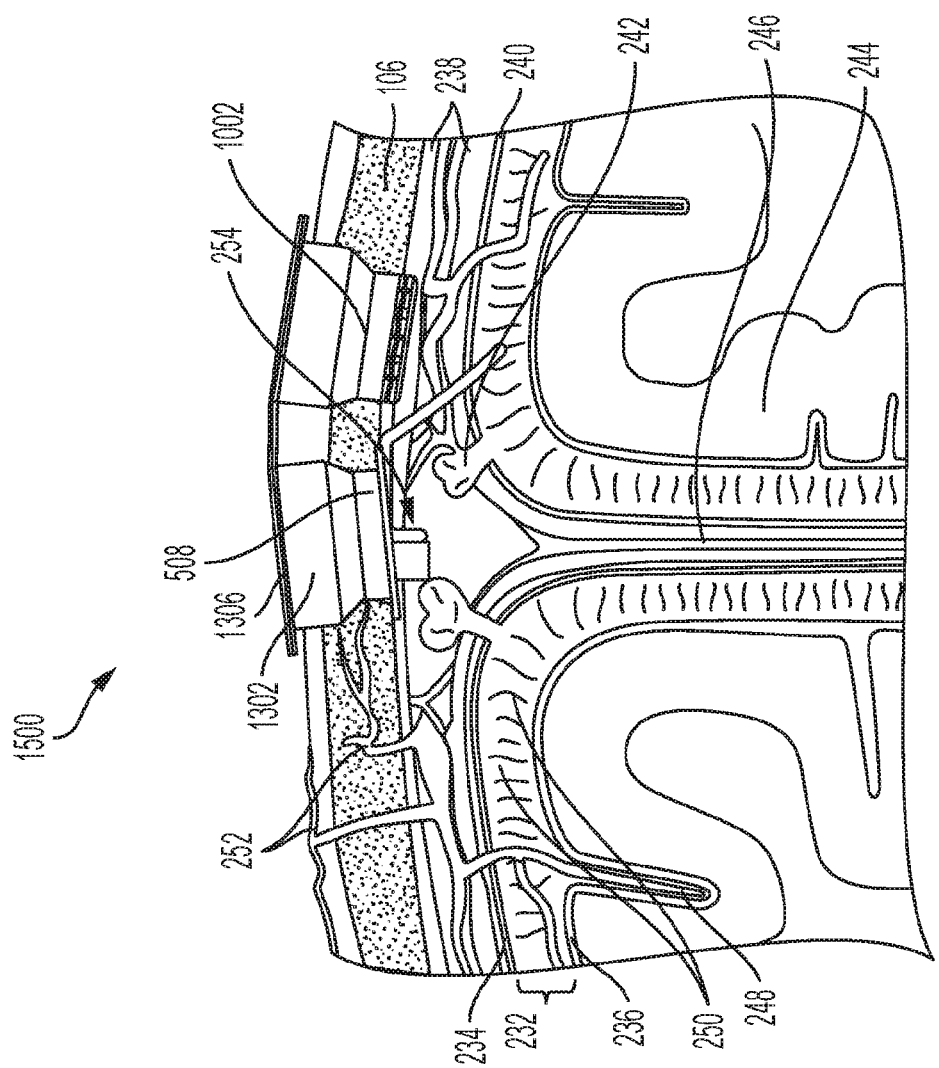
FIG. 15 depicts a coronal view of an illustrative implant system, in its final position on a subject's skull, according to one or more embodiments shown and described herein.

FIG. 15 depicts an illustrative implant system 1500 including a SAS implant plug 1002 (e.g. including a SAS inlet drain implant), a DVS implant 508 (e.g., including a DVS outlet drain implant), and a connector implant 1302 (e.g., including a connector plug element 1304, a reservoir and access port implant 1402, and a connector cap 1306), in its final position on a subject's skull 106. According to various aspects, a kit may include a guide device 200, as described herein, and the implant system 1500, as described herein. According to other aspects, given the modular nature of the implant system components, any defective or failing component can be individually tested and/or replaced as desired. Similar to FIG. 2B, further anatomical structures depicted in FIG. 15 include dura matter 238, the subdural space 240, arachnoid granulation villi 242, the longitudinal fissure 246, the cerebral cortex 244, the cerebral vein 248, the arachnoid trabeculae 250, pia matter 236, the subarachnoid space 232, arachnoid mater 234, veins 252 and the sinus 254.

According to various aspects, the implant system components (e.g., SAS inlet drain implant, SAS implant plug, connector implant, DVS implant plug, DVS outlet drain implant, and/or the like) may be formed using a polymer (e.g., silicon rubber and/or the like) or a polyester. According to other aspects, such implant system components may be formed using a metal (e.g., stainless steel, titanium, and/or the like).

Figure 16A:
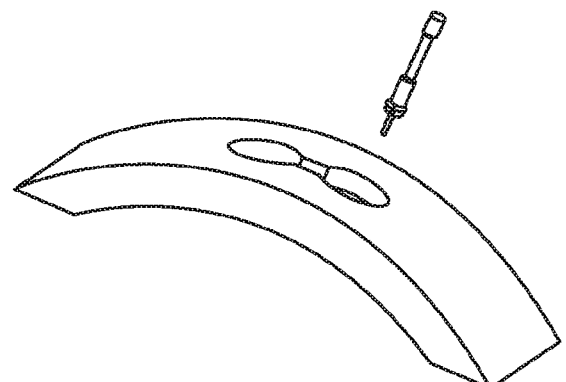
FIG. 16A depicts a perspective view of an illustrative instrument to check for venous blood flow before insertion of a DVS outlet drain implant including an outlet tip, according to one or more embodiments shown and described herein.
Figure 16B:
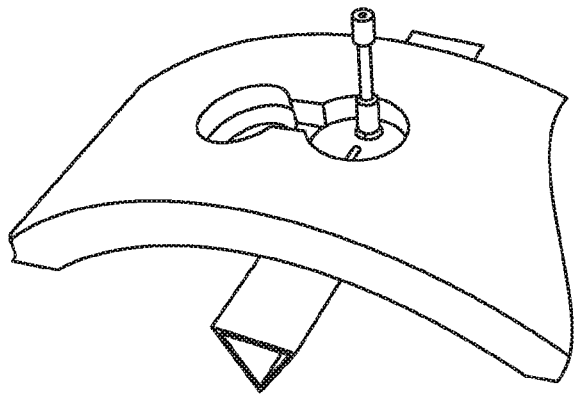
FIG. 16B depicts a perspective view of the illustrative instrument of FIG. 16A relative to a DVS implant plug and the sinus, according to one or more embodiments shown and described herein.
Figure 16C:
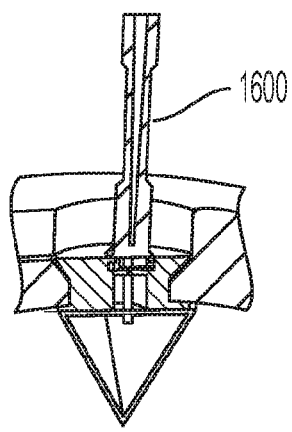
FIG. 16C depicts a cross-sectional view of the illustrative instrument of FIG. 16B, according to one or more embodiments shown and described herein.

FIGS. 16A-16C depict an illustrative instrument to check for venous blood flow before insertion of a DVS outlet tip according to various aspects of the present disclosure. In view of FIG. 16A-16C, once the outlet burr hole 312 over the dural venous sinus (e.g., the sagittal sinus, the transverse sinus, and/or the like) has been made, a hollow needle tool 1600 may be safely inserted through the access port (e.g., selectable location 516a of FIG. 5A) in the DVS implant plug to test for blood flow. According to various aspects, insertion of the hollow needle tool 1600 will not cause inadvertent bleeding as the access port has a slit/membrane seal at the entry port, as described herein (e.g., Similar to the method of FIG. 36).

FIGS. 17A-17C depict an illustrative instrument to check for physical depth of the dural venous sinus (e.g., the sagittal sinus, the transverse sinus, and/or the like) to properly size and/or position the DVS outlet tip implant prior to insertion. In view of FIG. 17A-17C, once the outlet burr hole 312 over the sinus has been made, a spring-loaded depth gauge tool 1700 may be safely inserted through the access port (e.g., selectable locations 516a of FIG. 5A) in the DVS implant plug to check for physical depth of the sinus to properly size and/or position the DVS outlet tip implant prior to insertion. According to various aspects, the positive blood flow test of FIGS. 16A-16C may be followed up with a mechanical or other method (e.g., ultrasound) determination of an actual depth of the sinus at the planned insertion point of the DVS outlet tip implant.

Figure 18:
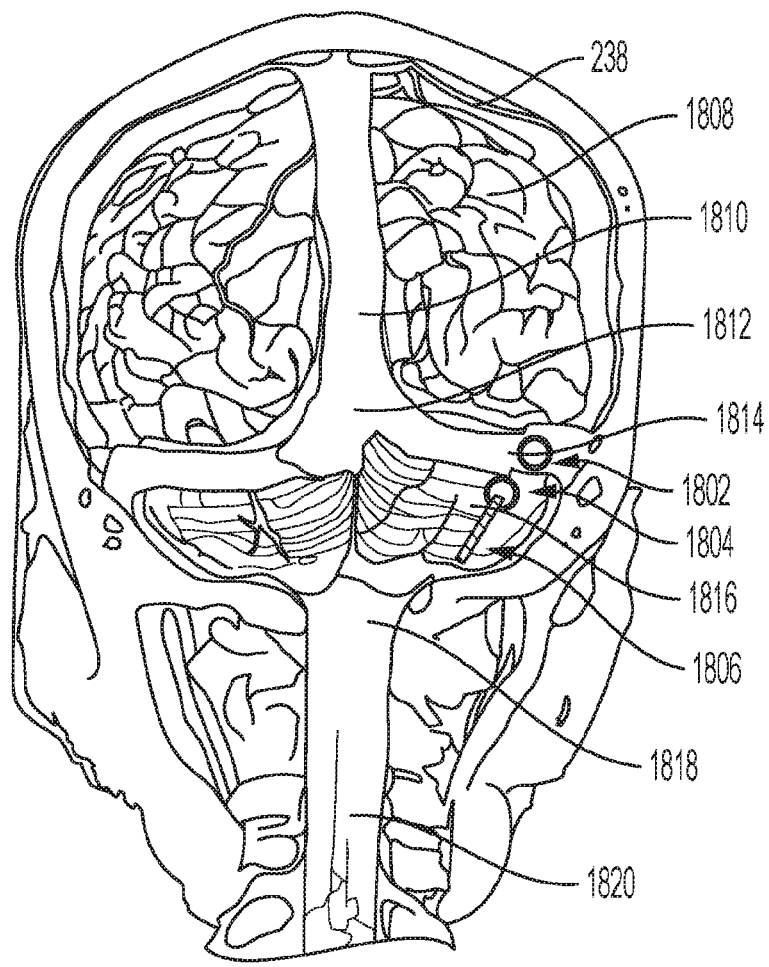
FIG. 18 depicts a posterior view of an illustrative posterior placement site of an implant system, according to one or more embodiments shown and described herein.

FIG. 18 depicts an illustrative posterior placement site according to various aspects of the present disclosure. In view of FIG. 18, the transverse sinus 1814 may be utilized as the outlet (drain) via a first burr hole 1802 and the cistern magna may be utilized as the inlet via a second burr hole 1804. Further in view of FIG. 18, an SAS inlet drain implant (catheter) 1806 (e.g., FIGS. 11A-11F) may be used to access the cistern magna region. Further anatomical structures depicted in FIG. 18 include dura mater 238, the occipital lobe 1808, the superior sagittal sinus 1810, the confluence of sinuses 1812, the cerebellum 1816, the arachnoid forming cisterna magna 1818, and the spinal cord 1820.

Figure 19:
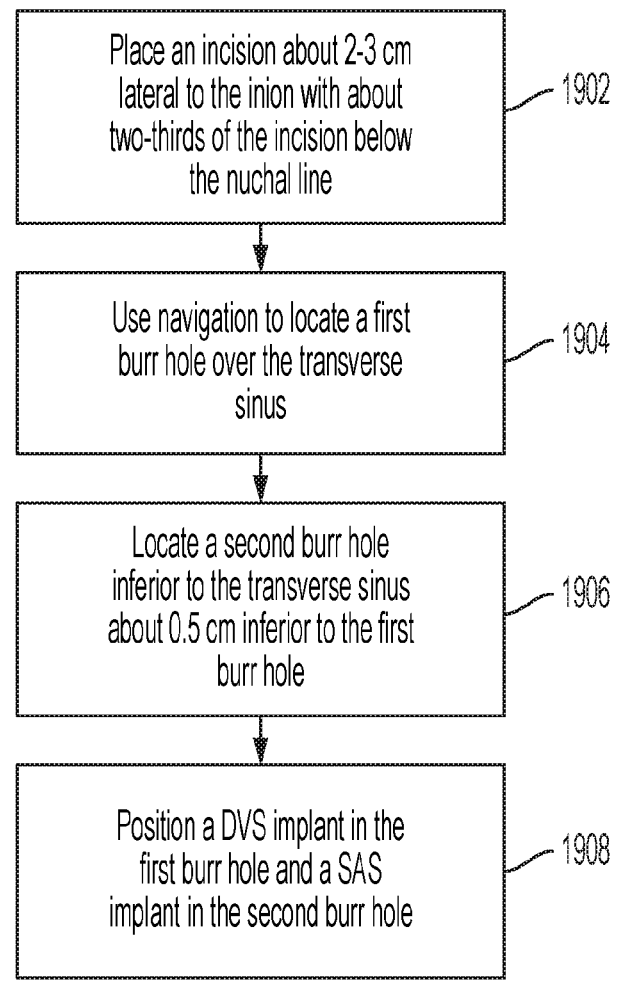
FIG. 19 depicts a flow diagram of an illustrative method for placing the posterior implant system of FIG. 18, according to one or more embodiments shown and described herein.

FIG. 19 depicts an illustrative method for placing the posterior implant system of FIG. 18 according to various aspects of the present disclosure. At block 1902, an incision about 2 cm to about 3 cm in length may be placed about 2 cm to about 3 cm lateral to the inion (e.g., the projecting part of the occipital bone at the base of the skull) with about two-thirds of the incision below the nuchal line (e.g., the upper external surface of the occipital bone). At block 1904, navigation may be used to localize/locate a first burr hole (outlet burr hole) over the transverse sinus. Notably, at this location, the transverse sinus is more uniformly shaped and closer in internal size to the jugular vein than the sagittal sinus. At block 1906, a second burr hole (inlet burr hole) may be localized/located inferior to the transverse sinus about 0.5 cm inferior to the first burr hole. Notably, in such an aspect, a density of gyri in the cerebellum makes manipulation of the SAS inlet drain easier and less injurious to the brain. At block 1908, a DVS implant and a SAS implant, as described herein, are positioned in the first burr hole and the second burr hole respectively (FIG. 20).

Figure 20:
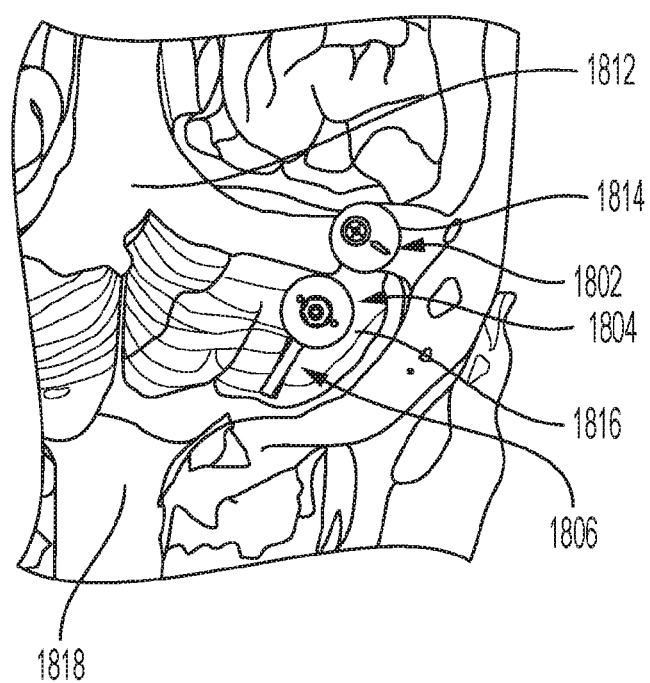
FIG. 20 depicts a posterior view of the illustrative posterior placement of a DVS implant and an SAS implant of the implant system of FIG. 18, according to one or more embodiments shown and described herein.

FIG. 20 depicts an illustrative posterior placement of a DVS implant and a SAS implant of the posterior implant system of FIG. 18 according to various aspects of the present disclosure. In view of FIG. 20, the DVS implant may be positioned in the first burr hole 1802 and the SAS implant may be positioned in the second burr hole 1804. According to various aspects, an SAS inlet drain 1806 associated with the SAS implant may extend about 1 cm to about 4 cm from the insertion point (e.g., at the SAS implant plug) down toward and into the cistern magna. According to various aspects, the SAS inlet drain may extend about 2 cm to about 3 cm from the insertion point (e.g., at the SAS implant plug) down toward and into the cistern magna. Notably, according to various aspects, locating the SAS inlet drain a minimum distance from the second burr hole may limit the inflammatory interaction of the post-procedure healing bone and dura. Such inflammation, if present, could cause a blockage of the inlet holes if they are positioned too close to the surgical site. Similar to FIG. 18, further anatomical structures depicted in FIG. 20 include the confluence of sinuses 1812, the transverse sinus 1814, the cerebellum 1816, and the arachnoid forming cisterna magna 1818.

Figure 21A:
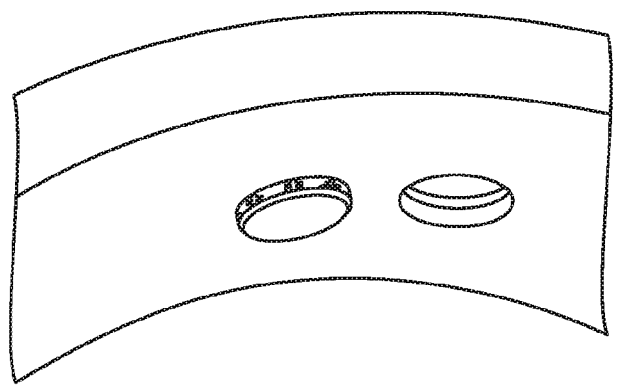
FIG. 21A depicts a bottom perspective view of an illustrative SAS implant plug including an integrated SAS inlet drain to locally drain CSF, according to one or more embodiments shown and described herein.
Figure 21B:
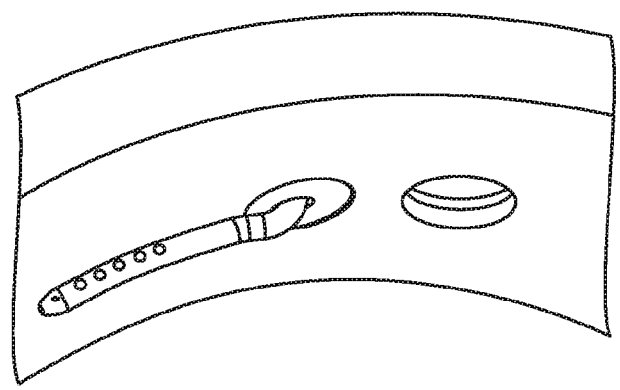
FIG. 21B depicts a bottom perspective view of an illustrative SAS implant plug including an SAS inlet drain implant coupled to the SAS implant plug to remotely drain CSF, according to one or more embodiments shown and described herein.
Figure 21C:
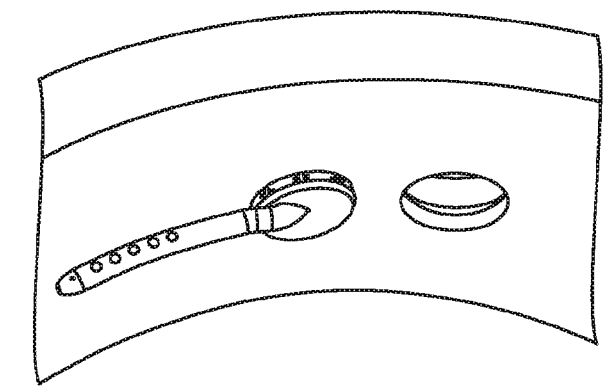
FIG. 21C depicts a bottom perspective view of an illustrative SAS implant plug including an integrated SAS inlet drain configured to locally and remotely drain CSF, according to one or more embodiments shown and described herein.

FIGS. 21A-21C depict illustrative SAS implants according to various aspects of the present disclosure. FIG. 21A illustrates an SAS implant including a landscape drain only. FIG. 21B illustrates an SAS implant including a catheter drain only. FIG. 21C illustrates an SAS implant including both a landscape drain and a catheter drain.

Figure 22A:
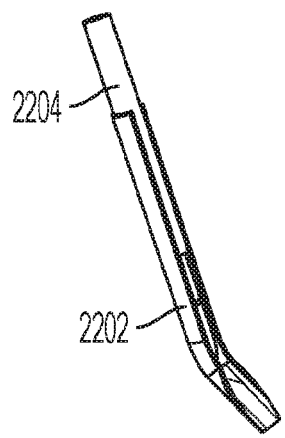
FIG. 22A depicts a perspective view of an illustrative SAS implant instrument usable to deploy or install a SAS inlet drain implant, according to one or more embodiments shown and described herein.
Figure 22B:
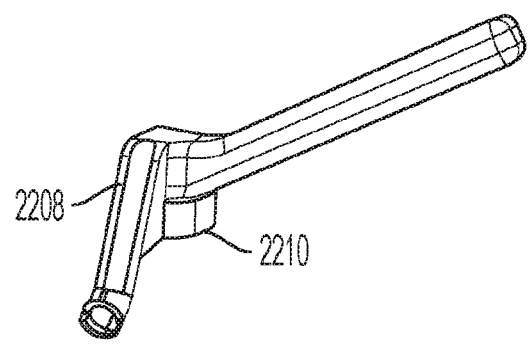
FIG. 22B depicts a perspective view of an illustrative SAS implant instrument usable to deploy or install a SAS inlet drain implant, according to one or more embodiments shown and described herein.
Figure 22C:
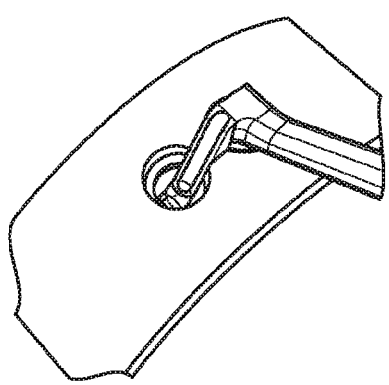
FIG. 22C depicts a perspective view of the illustrative SAS implant instrument of FIG. 22B locked into the inlet burr hole of the subject's skull, according to one or more embodiments shown and described herein.
Figure 22D:
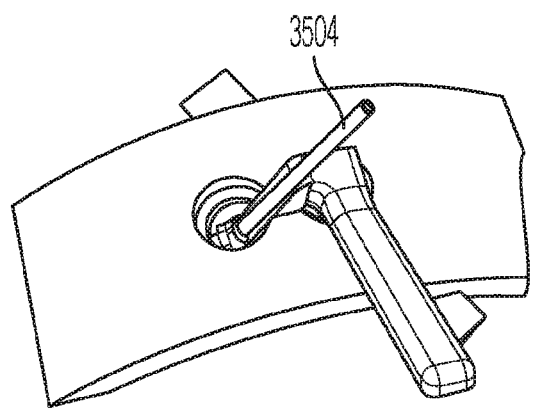
FIG. 22D depicts a perspective view of the illustrative SAS implant instrument of FIG. 22B deploying or installing a SAS inlet drain implant, according to one or more embodiments shown and described herein.
Figure 22E:
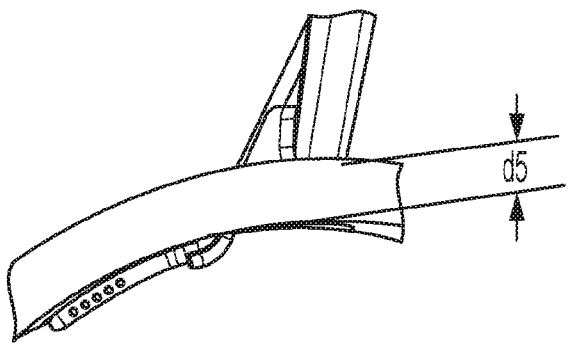
FIG. 22E depicts a side view of the illustrative SAS implant instrument of FIG. 22B deploying the SAS inlet drain implant of FIG. 22B, according to one or more embodiments shown and described herein.

FIGS. 22A-22E depict illustrative SAS implant instruments usable to deploy or install a SAS implant according to various aspects of the present disclosure. FIG. 22A depicts a SAS implant instrument 2202 including a slotted tube or channel appropriately sized for an SAS inlet drain implant 2204 to slide therethrough. In view of FIG. 22A, the SAS implant instrument 2202 may include a curved portion to assist in placing the SAS inlet drain implant 2204. According to various aspects, the SAS implant instrument 2202 may be positioned through a guide device 200 in a manner similar to the SAS implant instrument 1202 in FIG. 12C above. FIG. 22B depicts another SAS implant instrument 2208. Similar to FIG. 22A, the SAS implant instrument 2208 may include a slotted tube or channel appropriately sized for an SAS inlet drain implant 2204 to slide therethrough. Also, similar to FIG. 22A, the SAS implant instrument 2208 may include a curved portion to assist in placing the SAS inlet drain implant 2204. Unlike FIG. 22A, however, the SAS implant instrument 2208 may include a handle oriented at an angle (e.g., perpendicular) to the slotted tube or channel portion. Such an aspect may be more ergonomic for the surgeon as they insert the SAS inlet drain implant 2204. Further in such an aspect, a distance "d5" between a seat 2210 of the SAS implant instrument 2208 and a top of the curved portion may control a depth at which the SAS inlet tube 2204 is inserted. More specifically the SAS implant instrument 2208 may be a calibrated guide to facilitate insertion of a SAS inlet drain implant (e.g., catheter) into a specific anatomic region, at a specific distance, without causing inadvertent damage to the brain or other tissue (e.g. dura). For example, referring to FIGS. 22C-22D, the SAS implant instrument may lock into the burr holes to exactly place a remote portion of the SAS inlet drain implant. According to various aspects, the location for insertion may be based on burr hole placement as determined by the guide device 200 (e.g., drill guide). According to further aspects, a relative angle of insertion may be determined by desired anatomical location (e.g. in line with hole direction as shown in FIGS. 22B-22E).

Figure 23A:
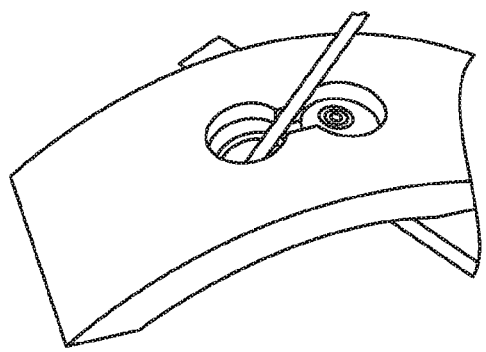
FIG. 23A depicts a perspective view of an illustrative SAS inlet drain implant being inserted between the dura and the brain, according to one or more embodiments shown and described herein.
Figure 23B:
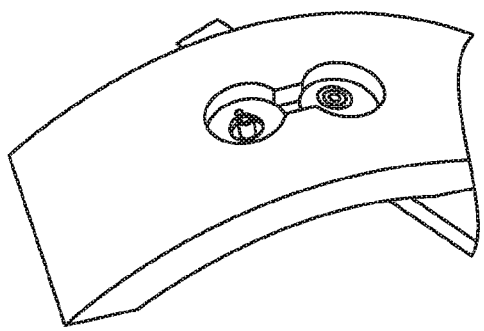
FIG. 23B depicts a perspective view of an illustrative portion of the SAS inlet drain implant of FIG. 23A protruding from a SAS implant plug, according to one or more embodiments shown and described herein.
Figure 23C:
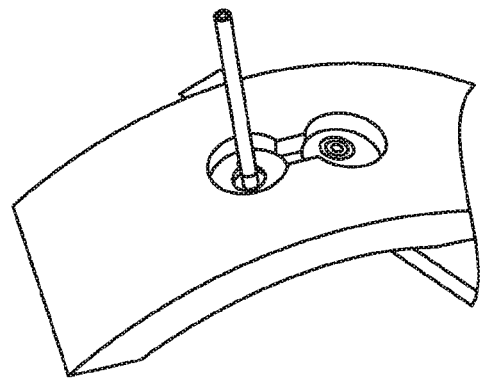
FIG. 23C depicts a perspective view of an illustrative tube coupleable with the protruding portion of FIG. 23B, according to one or more embodiments shown and described herein.
Figure 23D:
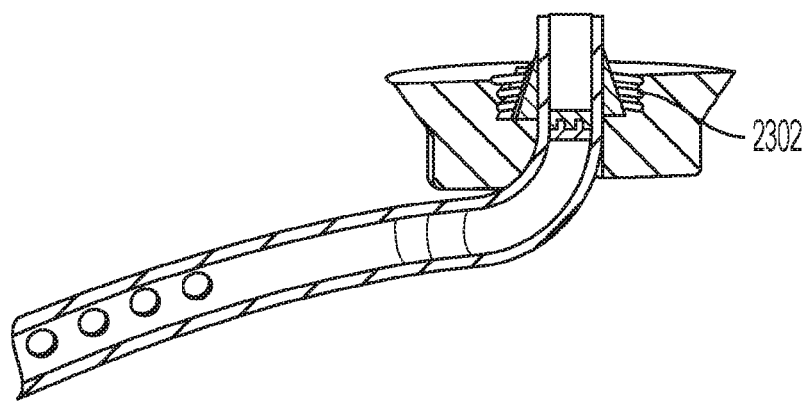
FIG. 23D depicts a cross-sectional view of an illustrative locking component to couple the SAS inlet drain implant to the SAS implant plug, according to one or more embodiments shown and described herein.

FIGS. 23A-23D depict illustrative features associated with an inserted SAS inlet drain implant (e.g., catheter) according to one or more aspects of the present disclosure. FIG. 23A depicts a flexible SAS inlet drain implant being inserted between the dura and the brain. FIG. 23B depicts a portion of the SAS inlet drain implant that protrudes from the SAS implant plug. FIG. 23C depicts a tube couplable with the protruding portion of FIG. 23B. According to various aspects, an inlet (SAS) catheter may include soft/flexible segments and stiff segments. Referring to FIG. 23D, according to such aspects, soft segments may be placed in contact with dura and/or the brain and relatively stiffer segments may be used to interface with the SAS implant plug to maintain leak-resistant/leak-proof integrity. Again referring to FIG. 23D, a stiffer portion may use locking components (e.g., compression fittings, locking ferrule arrangement, and/or the like) for leak-resistant/leak-proof attachments to the SAS implant plug and/or DVS implant plug. The stiffer portion may effectively lock the soft/flexible portion in place (e.g., relative to the skull bone). According to further aspects, the SAS implant plug and/or DVS implant plug may include a threaded locking collar 2302. According to other aspects, a compression ring and/or a collet-based design may be used. According to some aspects, an anti-rotation tool may be used to hold the SAS implant plug and/or the DVS implant plug in place when securing the catheter portions to the SAS implant plug and/or the DVS implant plug, respectively (e.g., FIG. 23C).

FIGS. 24A, 24B, and 24E depict illustrative SAS implants and DVS implants in position according to various aspects of the present disclosure. FIGS. 24C and 24D depict an illustrative implant system including an SAS implant, an DVS implant, and a connector implant, as described herein. More specifically, FIG. 24D illustrates a SAS inlet drain implant (e.g., FIG. 21B, including remotely located inlet holes) coupled to a SAS implant plug (e.g., via a locking SAS implant portion), where the SAS implant plug is fluidly coupled to a DVS implant plug via a connector element (e.g., FIG. 14C), where the DVS implant plug is coupled to a DVS outlet drain implant including an shaped outlet tip (e.g., FIG. 7C).

According to various aspects of the present disclosure SAS inlet drain implants and/or DVS outlet drain implants may be short relative to conventional ventricular shunts. According to such aspects, a shorter length(s) may result in less overall flow resistance and may minimize potential clogging issues.

Further, according to various aspects of the present disclosure, the SAS implant plug and the DVS implant plug may be independent units that secure their respective tubular elements (e.g., SAS inlet drain implant, DVS outlet drain implant, catheter, and/or the like) in place, distinctly and separately from each other. Each of the SAS implant plug and the DVS implant plug may be inserted either before or after catheter insertion, depending on the design. Notably, once its associated catheter is in place, the SAS implant plug or the DVS implant plug may secure the catheter (e.g., SAS inlet drain implant, DVS outlet drain implant, respectively) in place. According to various aspects, the SAS implant plug and/or the DVS implant plug may include an integral joining component to secure and/or isolate the catheters.

According to various aspects of the present disclosure, SAS implant plugs and/or DVS implant plugs (and their respective catheters) can now be joined with a joining cap and/or with additional tubing material (e.g., directly and/or indirectly) with appropriate length and joining ends. According to an alternative aspect, a form-in-place connecting cap may be utilized, utilizing an attachment element (e.g., an undercut, other interference, adhesive, and/or the like) to secure it in place on the skull after cure. Such a form-in-place connecting cap may be used to address an imperfect burr hole or another deformity (e.g., subject's skull). Such a form-in-place connecting cap could be made from a formable gasket material (e.g., polymer, plastic, and/or the like), use of a warm mold to allow softening, and subsequent shaping and placement of a gasket material.

According to yet further aspects of the present disclosure, the SAS implant plug and/or the DVS implant plug may include a variety of plugs with distinct durometer measures or for use within a plug of another durometer. According to some aspects, a SAS implant plug and/or DVS implant plug may include a hard inner portion for fixing the catheter surrounded by a softer material for interface with the skull bone.

Figure 25A:
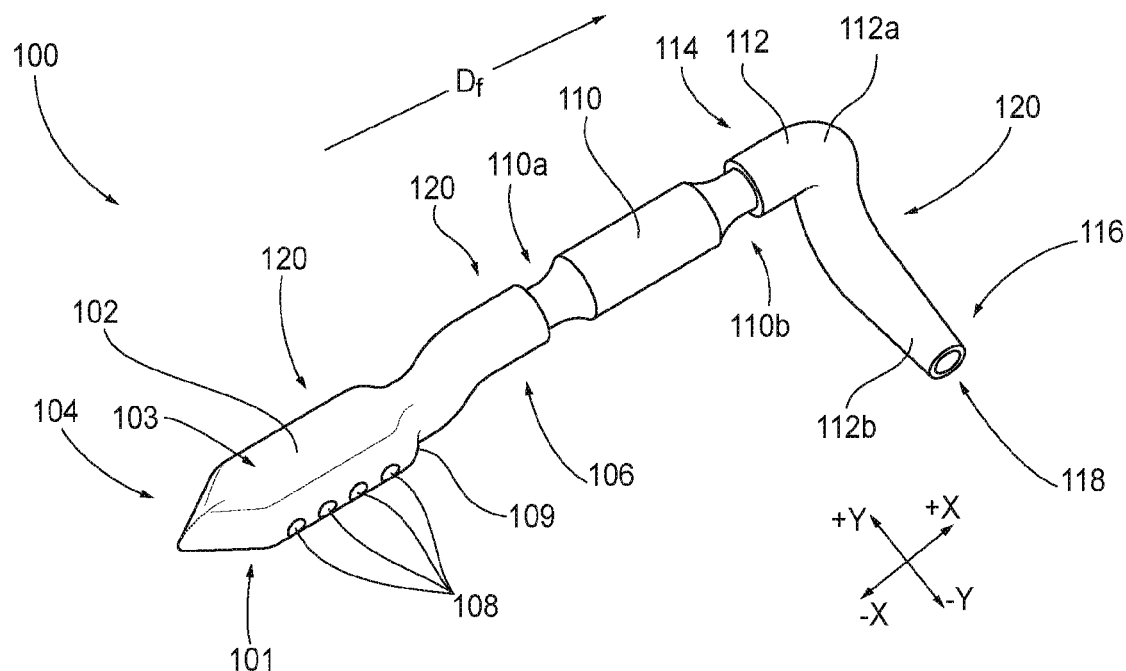
FIG. 25A depicts a perspective view of an illustrative intracranial, non-brain penetrating catheter device, according to one or more embodiments shown and described herein.

A further embodiment FIG. 25A depicts an implantable device, generally designated 2500, for drainage of fluid. In some embodiments, the implantable device 2500 may be a catheter. The implantable device 2500 may include a proximal portion 2502, a distal portion 2512, and a central portion 2510 disposed between the proximal portion 2502 and the distal portion 2512.

In embodiments where the implantable device 2500 is a catheter, it may be referred to as an intracranial catheter or a dural-sinus catheter. As such, the terms "system", "implantable device", "device", "drain", "drainage system", "drainage device", "catheter", "intracranial catheter" "SAS inlet drain implant" or "dural-sinus catheter" are interchangeable throughout the present disclosure.

The proximal portion 2502 may generally be located in a proximal area 2504 of the implantable device 2500. In various embodiments, the proximal portion 2502 is substantially flat. For example, the proximal portion 2502 has a first major surface 2501 and a second major surface 2503 that are substantially planar with respect to one another and spaced a distance from one another, where the distance is less than a length and/or a width of the proximal portion 2502, as described in greater detail herein. In another example, a cross section of the proximal portion 2502 may have a flattened oval shape where the first major surface 2501 and the second major surface 2503 are substantially curved toward one another. Other designs that result in a substantially flat shape of the proximal portion 2502 are contemplated and included within the scope of the present application. The substantially flat feature of the proximal portion 2502 is advantageous because it provides a larger surface area relative to a non-flat proximal portion when the proximal portion 2502 is inserted into the subarachnoid space of a subject. As such, a larger amount of tissue is compressed (e.g., brain, dura, and/or the like) by the proximal portion

2502 when the proximal portion 2502 is inserted, leaving additional space for free flow of fluid, as described in greater detail herein.

In some embodiments, the proximal portion 2502 may also include one or more openings 2508 on one or more sidewalls 2509 of the proximal portion 2502. As will be described in greater detail herein, the one or more openings 2508 may function as fluid inlets to allow drainage of fluid (e.g., CSF) into the implantable device 2500 and away from a cranial space, such as the subarachnoid space. In addition, the location of the one or more openings 2508 on the one or more sidewalls 2509 may be such so as to prevent obstruction or blockage from the adjacent dura or brain structure. That is, the substantially flat features of the proximal portion 2502 may compress an area of tissue in which it is inserted, creating a space for free fluid flow into the one or more openings 2508, thereby avoiding an instance where tissue is pressed up against the one or more openings 2508, which would block fluid flow. An area of the flat surface of the proximal portion 2502 may vary, as described in greater detail herein. It should be understood that a larger area of the flat surface of the proximal portion 2502 may provide increased fluid flow. More specifically, the flat profile of the proximal portion 2502 allows for a greater area for the one or more openings 2508 relative to a longitudinal design, such as a design employed by a typical tube catheter.

The distal portion 2512 may be located in a distal area 2516 of the implantable device 2500. The distal portion 2512 may be insertable into a venous sinus of a brain to allow drainage of fluid through the implantable device 2500 and into the blood system via the venous system. According to other aspects, the distal portion 2512 may be insertable into an SAS implant plug of the implant system as described herein. A tip opening 2518 at the end of the distal portion 2512 may act as an outlet for fluid.

The central portion 2510 of the implantable device 2500 is generally disposed between the proximal portion 2502 and the distal portion 2512. The central portion 2510 fluidly couples the proximal portion 2502 to the distal portion 2512. The central portion 2510 includes a proximal end 2510a and a distal end 2510b. The proximal end 2510a includes a connecting region where a distal end 2506 of the proximal portion 2502 is coupled to the central portion 2510. The distal end 2510b includes a connecting region where a proximal end 2514 of the distal portion 2512 is coupled to the central portion 2510. The proximal end 2510a and the distal end 2510b may include one or more features for connecting to the proximal portion 2502 and the distal portion 2512 respectively, as described in greater detail herein. In some embodiments, the central portion 2510 may be constructed of silicone such that the central portion 2510 functions as a silicone flanged union of the proximal portion 2502 and the distal portion 2512.

The proximal portion 2502, the central portion 2510, and the distal portion 2512 may generally be positioned relative to one another such that the proximal portion 2503, the central portion 2510, and a first section 2512a of the distal portion 2512 are generally in-line with one another. That is, the proximal portion 2502, the central portion 2510, and the first section 2512a of the distal portion 2512 are each generally extending in the same direction (e.g., along the +X/−X axis of the coordinate axes in FIG. 25A). The distal portion 2512 may be bent or otherwise curved such that a second section 2512b thereof extends in a direction that is not the same direction as the first section 2512a thereof. For example, the second section 2512b of the distal portion 2512 may extend in a direction that is substantially perpendicular to the direction in which the first section 2512a of the distal portion 2512 extends (e.g., along the +Y/−Y axis of the coordinate axes in FIG. 25A). Other directions are also contemplated and are included within the scope of the present disclosure. Such a curvature or angled trajectory of the distal portion 2512 may be formed by a user by bending the distal portion as necessary to fit a particular subject's anatomy and/or a particular SAS implant plug of an implant system as described herein. As such, the material used for the distal portion may be a deformable material. Deformable materials that are suitable for the various uses described herein should generally be understood. In some embodiments, the distal portion 2512 may further include a shape memory component such that a particular shape and positioning is "remembered" by the distal portion 2512 so that it can return to that shape and positioning after being deformed. This may allow the implantable device 2500 to bend when a straightening stylet is removed from within the implantable device to allow for a better cannulation of the venous channel at the time of insertion, as described in greater detail herein.

In some embodiments, the various portions of the implantable device 2500, including (but not limited to) the proximal portion 2502, the central portion 2510, and the distal portion 2512 may be coupled to one another via one or more mechanical interlock devices. For example, one or more of the proximal portion 2502, the central portion 2510, and the distal portion 2512 may include a fluid fitting such as Luer taper or the like that allows the various portions of the implantable device 2500 to be coupled or decoupled without fluid leakage. Such embodiments may be particularly used when the implantable device 2500 is placed within a subject as described herein so as to avoid fluid from crossing the blood brain barrier. Such mechanical interlock devices may also be used, for example, to allow insertion of a needle or the like into one or more portions of the implantable device 2500 without allowing fluid to escape (e.g., insert a needle into a reservoir to deliver medication or other fluid to the reservoir, as described in greater detail herein).

The implantable device 2500 may include one or more other deformable regions 2520. That is, the proximal portion 2502 may include one or more deformable regions 2520, the central portion 2510 may include one or more deformable regions 2520, and/or the distal portion 2512 may include one or more deformable regions 2520. The various deformable regions 2520 may generally allow the implantable device 2500 (or portions thereof) be deformable during insertion to facilitate entry into the dural sinus spaces, returning to their approximate original shape after insertion. For example, a deformable region 2520 in the proximal portion 2502 may facilitate introduction of the proximal portion under the dura, as described in greater detail herein.

Fluid may generally flow in a fluid direction $D_f$ such that the fluid is received in the one or more openings 2508 of the proximal portion 2502, flows through the proximal portion 2502, the central portion 2510, and the distal portion 2512, and out of the tip opening 2518 of the distal portion 2512, as described in greater detail herein.

Figure 25B:
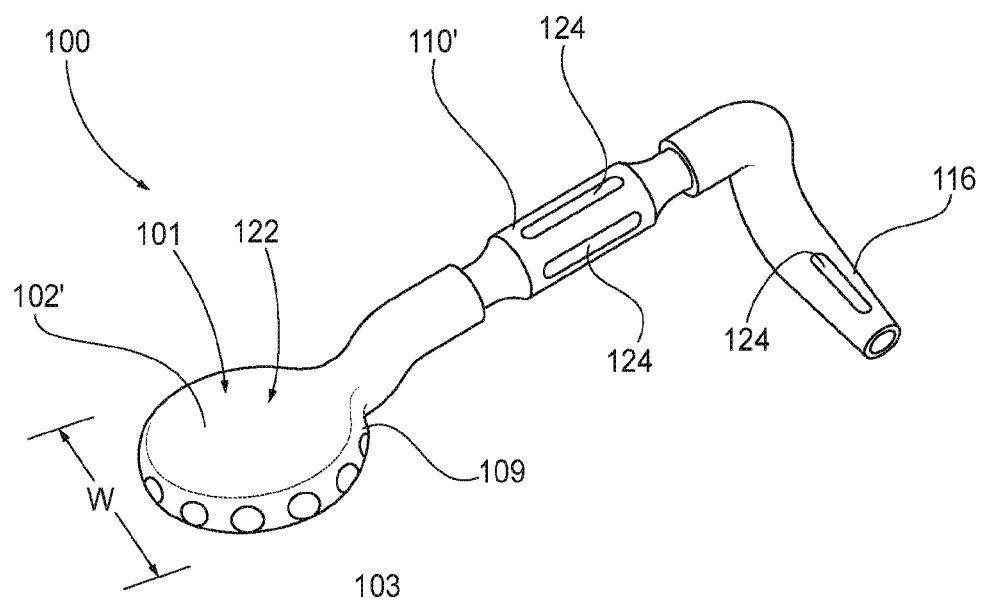
FIG. 25B depicts a perspective view of another illustrative intracranial catheter, according to one or more embodiments shown and described herein.

FIG. 25B depicts the implantable device 2500 having an alternative proximal portion 2502'. As shown in FIG. 25B, the alternative proximal portion 2502' may be shaped and/or sized in such a manner so as to maximize the surface area of the alternative proximal portion 2502'. For example, the first major surface 2501 of the alternative proximal portion 2502' and/or the second major surface 2503 of the alternative proximal portion 2502' may be substantially round. However, it should be understood that such a shape is merely illustrative, and the alternative proximal portion 2502' may exhibit any other shape without departing from the scope of the present disclosure. In addition, the alternative proximal portion 2502' may be made to any size. For example, a width W of the alternative proximal portion 2502' may be, but is not limited to, about 8 millimeters (mm) to about 10 mm, including about 8 mm, about 8.5 mm, about 9 mm, about 9.5 mm, about 10 mm, or any value or range between any two of these values (including endpoints). As will be described in greater detail herein, the various shapes and/or sizes of the alternative proximal portion 2502' may allow for greater fluid flow into the implantable device 2500.

Also depicted in FIG. 25B are one or more resonant strips 2524 located on various portions of the implantable device 2500. The one or more resonant strips 2524 may each be wires or other components that are attached to an outer surface of the implantable device. The one or more resonant strips 2524 may resonate the device when coupled to an external energy device, such as an ultrasound device, a radio frequency (RF) emitting device, and/or a laser energy emitting device. Such devices may be configured to improve the flow of fluid within the implantable device 2500 by generating waves that are used to cause the fluid to flow. While the resonant strips 2524 are only depicted in FIG. 25B, it should be understood that the resonant strips 2524 may be included in any of the embodiments described herein.

Figure 26:
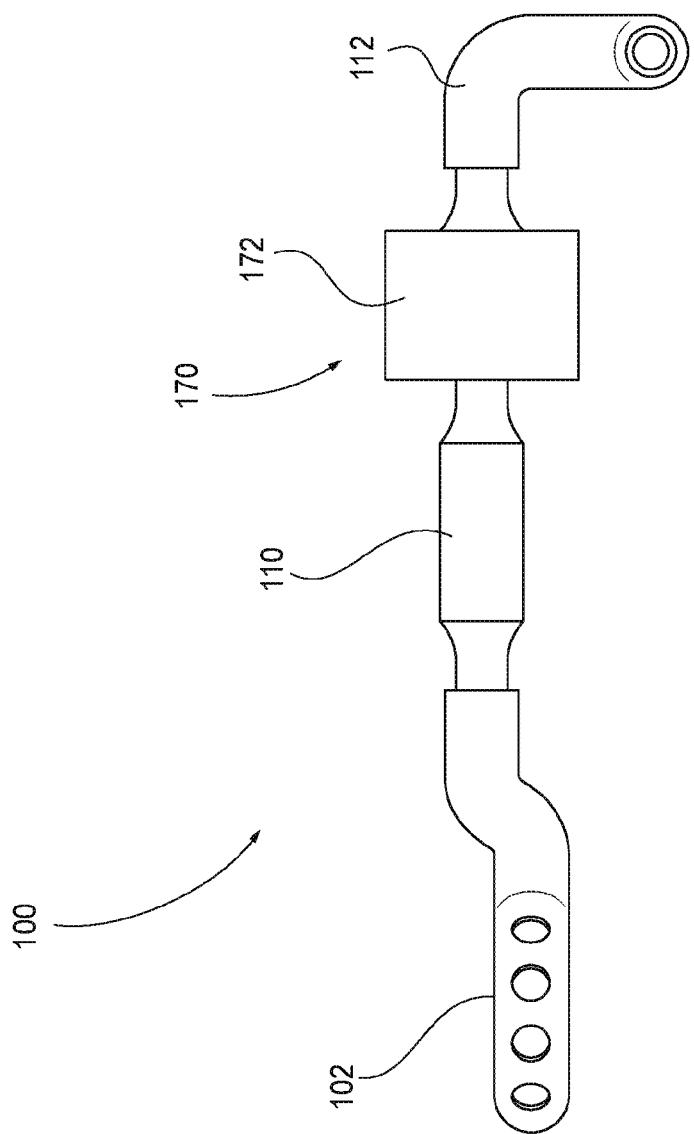
FIG. 26 depicts a side view of another illustrative intracranial catheter, according to one or more embodiments shown and described herein.

FIG. 26 depicts another embodiment of the implantable device 2500 that contains a second central portion 2670 disposed between the proximal portion 2502 and the distal portion 2512 and fluidly coupled to the proximal portion 2502 and the distal portion 2512. In some embodiments, the second central portion 2670 may be disposed between the distal portion 2512 and the central portion 2510, as shown in FIG. 26. However, it should be understood that the second central portion 2670 may also be disposed between the proximal portion 2502 and the central portion 2510. In some embodiments, the second central portion 2570 may replace the central portion 2510. In still other embodiments, the second central portion 2670 may be integrated with the central portion 2510.

The second central portion 2670 may include one or more components that are particularly configured to provide targeted drugs to particular areas of a subject, such as (but not limited to) the dural venous sinus (e.g., the sagittal sinus, the transverse sinus, and the like), the subarachnoid space, and/or the like. For example, chemotherapy medication, ALS medication, Alzheimer's medication (e.g., chelating or enzymatic methods), stroke treatment medication (e.g., TPA), genetic (e.g., chromosomal) manipulation therapy, treatments for bacterial or viral infections, treatment for brain hemorrhage control, and/or the like may be delivered to the particular areas via the second central portion 2670 of the implantable device 2500. Illustrative examples of various components that are particularly configured to provide targeted drugs include, but are not limited to, a reservoir 2672.

The reservoir 2672 may be particularly shaped and/or sized to contain a particular amount of material (e.g., fluid) therein. The particular amount of material may correspond to a particular amount of medication to be delivered by the implantable device 2500, for example. The reservoir 2672 may be fluidly coupled to the various portions of the implantable device 2500 such that the materials within the reservoir 2672 are transported from the reservoir 2672 to the subarachnoid/subdural space, and/or the like via the various portions, including the proximal portion 2502 and/or the distal portion 2512. The reservoir 2672 may include a seal or the like in a portion thereof such that an internal portion of the reservoir 2672 can be accessed for dispensing medication or the like into the reservoir. That is, a user may access the internal portion of the reservoir 2672 and dispense the medication into the reservoir 2672 such that the medication can be distributed to the various other portions of the implantable device 2500, as described herein.

In some embodiments, the reservoir 2672 may be constructed and configured such that the reservoir 2672 can hold a pressurized fluid therein. That is, the reservoir 2672 may be constructed of a particular material that is able to withstand an increased fluid pressure. In addition, the reservoir 2672 may include one or more various components, such as valves or the like such that a particular fluid pressure is maintained in the reservoir 2672. A pressurized fluid may be necessary in the reservoir to ensure that the medication contained within the fluid can be dispensed to particular locations, as described herein. That is, the pressure of the fluid within the reservoir 2672 may cause a force that directs fluid in a particular direction when the fluid exits the reservoir 2672 to the various other portions of the implantable device 2500.

In some embodiments, the reservoir 2672 may be positioned adjacent to a burr hole (e.g., inlet burr hole, outlet burr hole) in a subject's skull such that the reservoir 2672 is accessible without disturbing the inlet and outlet portions. That is, medication or the like may be distributed to the reservoir (and subsequently the various other portions of the implantable device 2500) via the burr hole. For example, a user may remove a chamber plug (e.g., SAS implant plug) or the like (as described in greater detail herein) from the burr hole to reveal at least a portion of the reservoir 2672, which can receive the medication and/or the like.

It should be understood that the introduction of medication to targeted areas via use of the second central portion 2670 and/or the various components thereof may allow for use of certain medications that would otherwise not be suited for targeted therapy. More specifically, medications that are not designed to cross the blood-brain barrier may be delivered using the implantable device 2500 with the second central portion 2670, as the implantable device 2500 crosses the blood-brain barrier.

Figure 27:
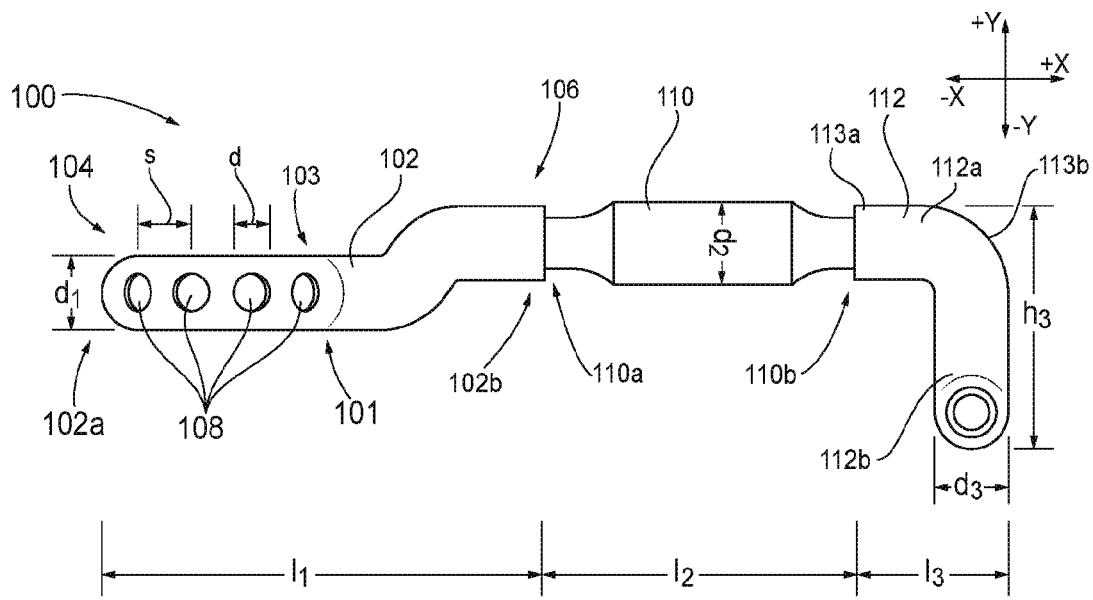
FIG. 27 depicts a side view of an illustrative intracranial catheter, according to one or more embodiments shown and described herein.

FIG. 27 depicts additional details regarding the size of various portions of the implantable device 2500 according to various embodiments. For example, the proximal portion 2502 may have a first length $l_1$, the central portion 2510 may have a second length $l_2$, and the distal portion 2512 may have a third length $l_3$. According to various aspects, the second length $l_2$ must sit at a level of the lower table, above the upper table or totally within the cancellous region of the cranial bone. The first length $l_1$ of the proximal portion 2502 may be an overall length of the proximal portion 2502, such as, for example, an average distance between a first end 2502a and a second end 2502b of the proximal portion 2502 and/or a distance between the proximal area 2504 of the implantable device 2500 and the distal end 2506 of the proximal portion 2502. In some embodiments, the first length $l_1$ of the proximal portion 2502 may be a straight-line length of the proximal portion 2502 that does not take into account various curved portions, bent portions, or the like of the proximal portion 2502 (e.g., when traversing the proximal portion 2502 along the +X/−X axis of the coordinate axes of FIG. 27). Illustrative examples of the first length $l_1$ may include, but are not limited to, about 10 mm to about 12 mm, including about 10 mm, about 10.25 mm, about 10.5 mm, about 10.75 mm, about 11 mm, about 11.25 mm, about 11.5 mm, about 11.75 mm, about 12 mm, or any value or range between any two of these values (including endpoints).

The second length $l_2$ of the central portion 2510 may be an overall length of the central portion 2510, such as, for example, an average distance between the proximal end 2510a and the distal end 2510b thereof. In some embodiments, the second length $l_2$ of the central portion 2510 may be a straight-line length of the central portion 2510 that does not take into account various curved portions, bent portions, or the like of the central portion 2510. Illustrative examples of the second length $l_2$ may include, but are not limited to, about 8 mm to about 12 mm, including about 8 mm, about 8.5 mm, about 9 mm, about 9.5 mm, about 10 mm, about 10.5 mm, about 11 mm, about 11.5 mm, about 12 mm, or any value or range between any two of these values (including endpoints).

The third length $l_3$ of the distal portion 2512 may generally correspond to the length of the first section 2512a of the distal portion 2512. That is, the third length $l_3$ may be a distance between a first end 2713a of the distal portion 2512 and an angled end 2713b of the distal portion 2512. It should be understood that the angled end 2713b of the distal portion 2512 refers to a surface of the distal portion 2512 that is the furthest distance from the first end 2502a of the proximal portion 2502 when the implantable device is traversed along the +X/−X axis of the coordinate axes of FIG. 27. Illustrative examples of the third length $l_3$ may include, but are not limited to, about 4 mm to about 6 mm, including, about 4 mm, about 4.5 mm, about 5 mm, about 5.5 mm, about 6 mm, or any value or range between any two of these values (including endpoints).

Accordingly, the total length $l_T$ may generally be the combined lengths of the first length $l_1$, the second length $l_2$, and the third length $l_3$. In some embodiments, the total length $l_T$ may be less than the combined lengths of the first length $l_1$, the second length $l_2$, and the third length $l_3$ because the various portions may fit inside one another when coupled (e.g., the central portion 2510 may be partially inserted within the proximal portion 2502 and/or the distal portion 2512). Illustrative examples of the total length $l_T$ include, but are not limited to, about 22 mm to about 30 mm, including about 22 mm, about 22.5 mm, about 23 mm, about 23.5 mm, about 24 mm, about 24.5 mm, about 25 mm, about 25.5 mm, about 26 mm, about 26.5 mm, about 27 mm, about 27.5 mm, about 28 mm, about 28.5 mm, about 29 mm, about 29.5 mm, about 30 mm, or any value or range between any two of these values (including endpoints). In some embodiments, the total length $l_T$ may be about 25 mm to about 27 mm. It should be understood that the total length $l_T$ may correspond to a length that allows the implantable device 2500 to extend between the subarachnoid space to the venous system of a subject when the implantable device 2500 is implanted in the subject, as described herein. According to other aspects, the total length $l_T$ may correspond to a length that allows the implantable device 2500 to extend between the subarachnoid space and a SAS implant plug of the implant system as described herein.

In various embodiments, the central portion 2510 may have a diameter $d_2$. The diameter $d_2$ of the central portion 2510 may be an average diameter across the entire second length 12 or may be a diameter of a particular section of the central portion 2510, such as, for example, the section being the largest in size. Illustrative examples of the diameter $d_2$ of the central portion 2510 may include, but are not limited to, about 2 mm to about 3 mm, including about 2 mm, about 2.1 mm, about 2.2 mm, about 2.3 mm, about 2.4 mm, about 2.5 mm, about 2.6 mm, about 2.7 mm, about 2.8 mm, about 2.9 mm, about 3 mm, or any value or range between any two of these values (including endpoints).

In various embodiments, the second section 2512b of the distal portion 2512 may have a height $h_3$. That is, the height $h_3$ may correspond to a distance between the first section 2512a of the distal portion 2512 and the tip opening 2518 of the distal portion 2512. In some embodiments, the height $h_3$ of the second section 2512b of the distal portion 2512 may be about 7 mm to about 9 mm, including about 7 mm, about 7.5 mm, about 8 mm, about 8.5 mm, about 9 mm, or any value or range between any two of these values (including endpoints).

Other various portions of the implantable device 2500 may also have particular dimensional aspects. For example, the proximal portion 2502 may have a distance $d_1$ between the first major surface 2501 and the second major surface 2503 thereof. The distance $d_1$ may be, for example, about 2 mm to about 3 mm, including about 2 mm, about 2.1 mm, about 2.2 mm, about 2.3 mm, about 2.4 mm, about 2.5 mm, about 2.6 mm, about 2.7 mm, about 2.8 mm, about 2.9 mm, about 3 mm, or any value or range between any two of these values (including endpoints). The distance $d_1$ may be such that the proximal portion 2502 is thin enough to fit within the subarachnoid space of a subject when the implantable device 2500 is implanted in a subject, as described herein.

In some embodiments, the one or more openings 2508 in the proximal portion 2502 may be spaced at a particular distance from one another and/or may be sized/shaped in a particular manner so as to allow a particular amount of fluid to flow into the implantable device 2500. For example, in embodiments having a plurality of openings 2508 in the proximal portion 2502, each of the plurality of openings 2508 may have a particular spacing S between one another. The spacing S generally refers to a distance between two of the plurality of openings 2508, which may be measured between facing edges of the plurality of openings 2508, between corresponding edges of each of the plurality of openings 2508, from a center of each of the plurality of openings 2508, or the like. The spacing S may be, for example, about 1 mm to about 3 mm, including about 1 mm, about 1.25 mm, about 1.5 mm, about 1.75 mm, about 2 mm, about 2.25 mm, about 2.5 mm, about 2.75 mm, about 3 mm, or any value or range between any two of these values (including endpoints). In addition to the spacing S, each of the one or more openings 2508 may have a particular diameter d. The diameter d may be, for example, an average diameter from one edge to an opposite edge, an exact diameter in instances where the opening 2508 has a circular shape, or the like. The diameter d may be, for example, about 0.5 mm to about 1.5 mm, including about 0.5 mm, about 0.75 mm, about 1 mm, about 1.25 mm, about 1.5 mm, or any value or range between any two of these values (including endpoints).

In some embodiments, the tip opening 2518 of the distal portion 2512 may have a particular shape and/or size, such as, for example, a tip opening diameter $d_3$. The tip opening diameter $d_3$ may be an average diameter, an actual diameter, and/or the like. In some embodiments, the tip opening diameter $d_3$ may be about 1 mm to about 2 mm, including about 1 mm, about 1.1 mm, about 1.2 mm, about 1.3 mm, about 1.4 mm, about 1.5 mm, about 1.6 mm, about 1.7 mm, about 1.8 mm, about 1.9 mm, about 2 mm, or any value or range between any two of these values (including endpoints). It should be understood that the tip opening diameter $d_3$ may be particularly shaped and/or sized to allow a particular amount of fluid to flow therethrough. In addition, the tip opening 2518 may be particularly sized to accommodate different dural-sinus sizes of different subjects (e.g., subjects of a particular age group or the like). According to other aspects, the tip opening 2518 may be particularly sized to accommodate a diameter of the central portion (e.g., 1014, 1024 of an SAS implant plug.

Figure 28A:
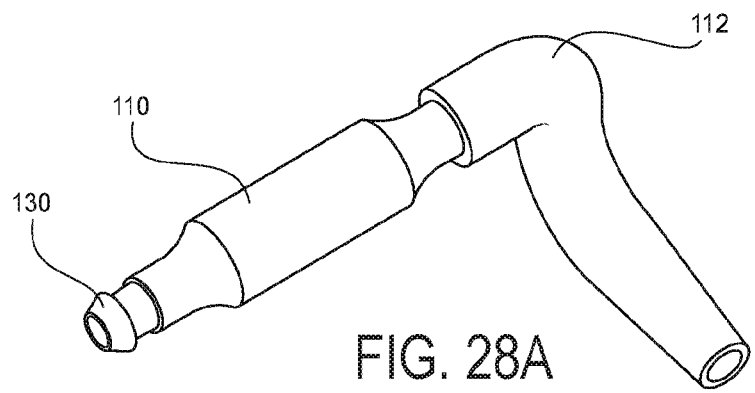
FIG. 28A depicts a perspective view of a portion of an illustrative intracranial catheter showing an angled trajectory at a portion to be placed in a dural venous sinus of a subject, according to one or more embodiments shown and described herein.

As previously described herein, the central portion 2510 may be particularly shaped such that it can be fluidly coupled to the proximal portion 2502 and/or the distal portion 2512. That is, proximal and distal ends of the central portion 2510 may have specialized features for connecting, respectively, with the proximal portion 2502 and the distal portion 2512 of the implantable device. As such, the proximal portion 2502 may include an end portion which is configured to fit the proximal end of the central portion 2510. The proximal end and distal end of the central portion 2510 may be configured to snugly fit the proximal portion 2502 and the distal portion 2512, respectively. For example, as shown in FIG. 28A, the central portion 2510 may include one or more mating features 2830 that allow the central portion 2510 to mate with the various other portions of the implantable device 2500 (FIG. 25A). Such mating features 2830 are not limited by the present disclosure and may be any mating feature now known or later developed. For example, the mating feature 2830 may be a flange, one or more ribs, and/or the like that allow for the various other portions (e.g., the proximal portion 2502 (FIG. 25A) and/or the distal portion 2512) to be placed thereover and held in place by the flange, one or more ribs, and/or the like. In some embodiments, the mating feature may be a Luer taper or the like, as described herein.

Figure 28B:
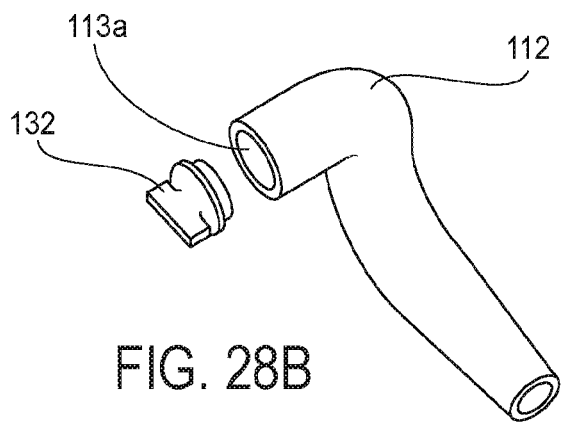
FIG. 28B depicts a perspective view of a portion of an illustrative intracranial catheter and a corresponding plug, according to one or more embodiments shown and described herein.

The various portions of the implantable device 2500 (FIG. 25A), including the proximal portion 2502, the central portion 2510, and the distal portion 2512 may be separable from one another. For example, it may be desirable to separate one or more portions of the implantable device 2500 (FIG. 25A) after a procedure has been completed and abandon certain portions (e.g., allow certain portions to remain within the subject's body). As such, it may be necessary to plug one or more portions remaining within the subject body upon abandonment to avoid unnecessary fluid flow or the like. For example, as shown in FIG. 28B, the distal portion 2512 may be detachable from the various other portions of the implantable device 2500 (FIG. 25A) and an opening in the first end 2713a of the distal portion 2512 may be plugged with a plug 2832. The plug 2832 may be shaped and/or sized to correspond to the opening in the first end 2713a of the distal portion 2512 such that it can be inserted to prevent fluid flow. In some embodiments, the distal portion 2512 may be detachable from the various other portions of the implantable device 2500 (FIG. 25A) when it is not needed to drain fluid (e.g., when the implantable device 2500 is used for the purposes of delivering medication).

Figure 29:
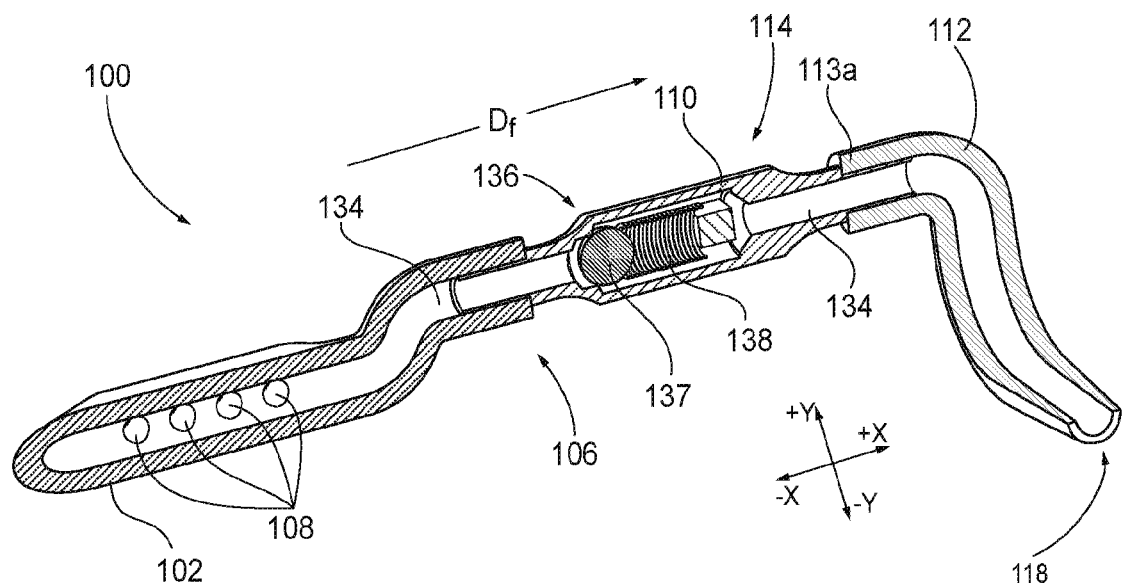
FIG. 29 depicts a perspective cross-sectional view of an illustrative intracranial catheter having a unidirectional valve therein, according to one or more embodiments shown and described herein.

FIG. 29 depicts a view of various components inside the implantable device 2500 according to various embodiments. Each of the various portions of the implantable device 2500, including the proximal portion 2502, the central portion 2510, and the distal portion 2512 is hollow such that a bore 2934 runs through each portion. In addition, as previously described herein, the various portions of the implantable device 2500 are fluidly coupled to one another such that fluid may move between the hollow bores 2934 of the respective portions.

In some embodiments, the central portion 2510 may include a valve 2936 that is particularly configured to restrict fluid flow in a particular direction. For example, the valve 2936 may be a check valve that prevents a backflow of blood into the subarachnoid space when the implantable device 2500 is implanted in a subject as described herein. That is, the valve 2936 may ensure unidirectional flow of fluid inside the implantable device 2500. More specifically, the fluid may only flow in the fluid direction $D_f$, such as, for example, CSF flow from the subarachnoid space to the venous sinus (e.g., directly or indirectly via the implant system as described herein). One illustrative example of a check valve may be a ball-in-cone valve, which includes a valve ball 2937 and a biasing assembly 2938 (e.g., a spring), such as, for example, the miniNav™ valve (Aesculap, Inc., Center Valley, PA). The biasing assembly 2938 may bias the valve ball 2937 in the proximal direction (e.g., along the −X direction of the coordinate axes of FIG. 29) such that the valve ball blocks fluid flow into the hollow bore 2934 of the central portion 2510 from the hollow bore 2934 of the proximal portion 2502. The biasing force of the biasing assembly 2938 on the valve ball 2937 may provide a particular valve opening pressure. As soon as a fluid pressure (e.g., the intraventricular pressure) exceeds the valve opening pressure, the biasing assembly 2938 is compressed, the valve ball 2937 moves out of its biased position (e.g., out of a cone), thereby providing an opening in the hollow bore 2934 to allow fluid to flow therethrough. As such, the CSF is drained out through the gap that opens as a result of the valve ball 2937 movement when the implantable device 2500 is implanted in a subject as described herein. The valve opening pressure may be adjustable such that a particular pressure can be selected according to a particular subject's symptoms. For example, the miniNav™ may be available with four pressure levels. Postoperatively, the pressure level of each valve can be recognized by the shape of the valve shell. For instance, a valve with concave (inward-curving) outlines at the proximal end and convex (outward-curving) contours at the distal end has an opening pressure of about 5 cm $H_2O$.

It should be understood that the valve 2936 is not limited to a check valve. Other valves or similar devices may also be used without departing from the scope of the present disclosure. For example, in some embodiments, the valve 2936 may include integral flow limiting portions of the design thereof, such as flap valves or the like that are integrated into a structure of the central portion 2510 utilizing an appropriate material change of durometer in that region of the device.

Figure 30:
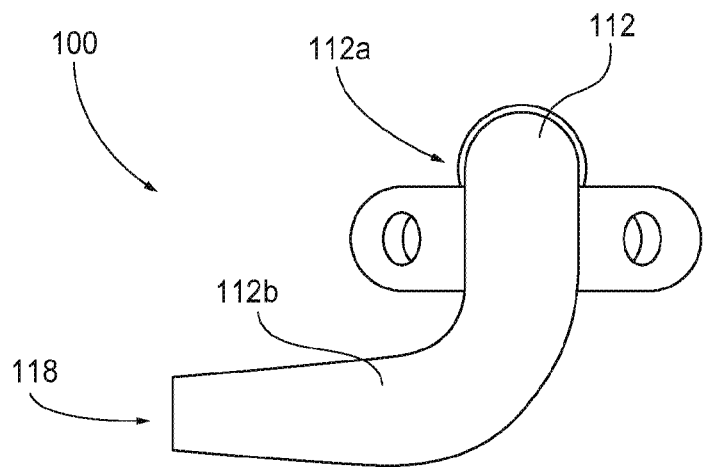
FIG. 30 depicts an end view of an illustrative intracranial catheter, according to one or more embodiments shown and described herein.

FIG. 30 depicts an end view of the implantable device 2500 according to various embodiments. As previously described herein, the distal portion 2512 may include an angled trajectory. That is, the distal portion 2512 may be bent or otherwise angled/curved such that the second section 2512b thereof extends in a direction that is not the same direction as the first section 2512a thereof. The distal portion 2512 may be angled, for example, such that the distal portion 2512 can be placed against blood flow to prevent the formation of blood clots over the tip opening 2518 (e.g., when the implantable device 2500 is being used separate from the implant system described herein). However, it should be understood that this is merely illustrative. In some embodiments, the distal portion 2512 may be placed with the blood flow, particularly in embodiments where the implantable device 2500 is used to provide medication or the like to a subject. As previously described herein, the tip opening 2518 may be particularly sized and/or shaped to accommodate the sizes of different dural venous sinuses (e.g., the sagittal sinus, the transverse sinus, the sigmoid sinus, and/or the like) of different subjects. As such, it should be understood that the distal portion 2512 may include various interchangeable sizes of tips such that the tip opening 2518 can be adjusted as needed and might also include a one-way flow control portion in the tip of 2518, such as a slit valve or flap valve (e.g., similar to the DVS outlet drain implant including the various outlet tips as described herein).

Figure 31A:
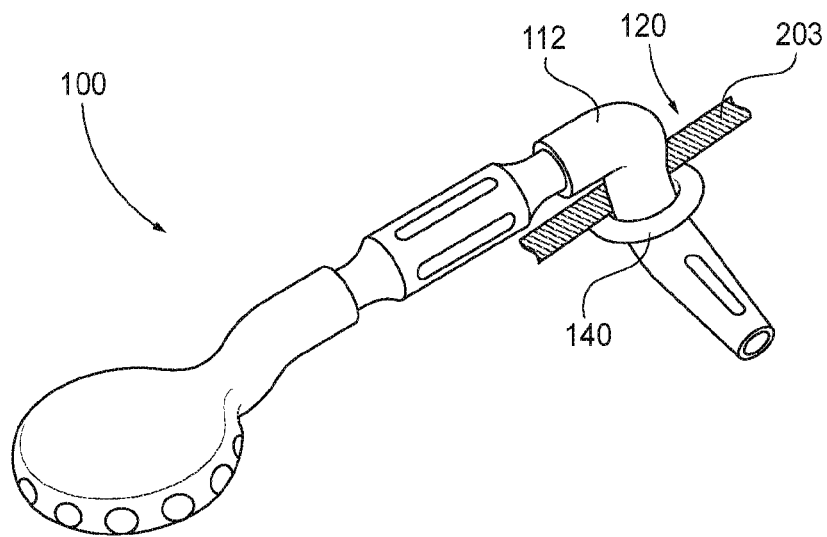
FIG. 31A depicts a perspective view of an illustrative intracranial catheter having a balloon assist mechanism, according to one or more embodiments shown and described herein.
Figure 31B:
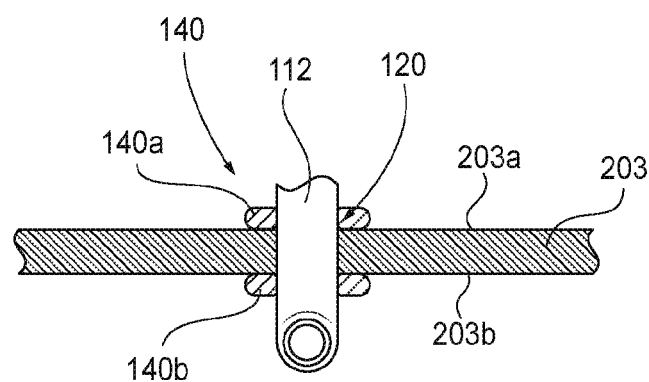
FIG. 31B depicts a side view of the intracranial catheter having the balloon assist mechanism of FIG. 31A when inserted in a subject, according to one or more embodiments shown and described herein.
Figure 33:
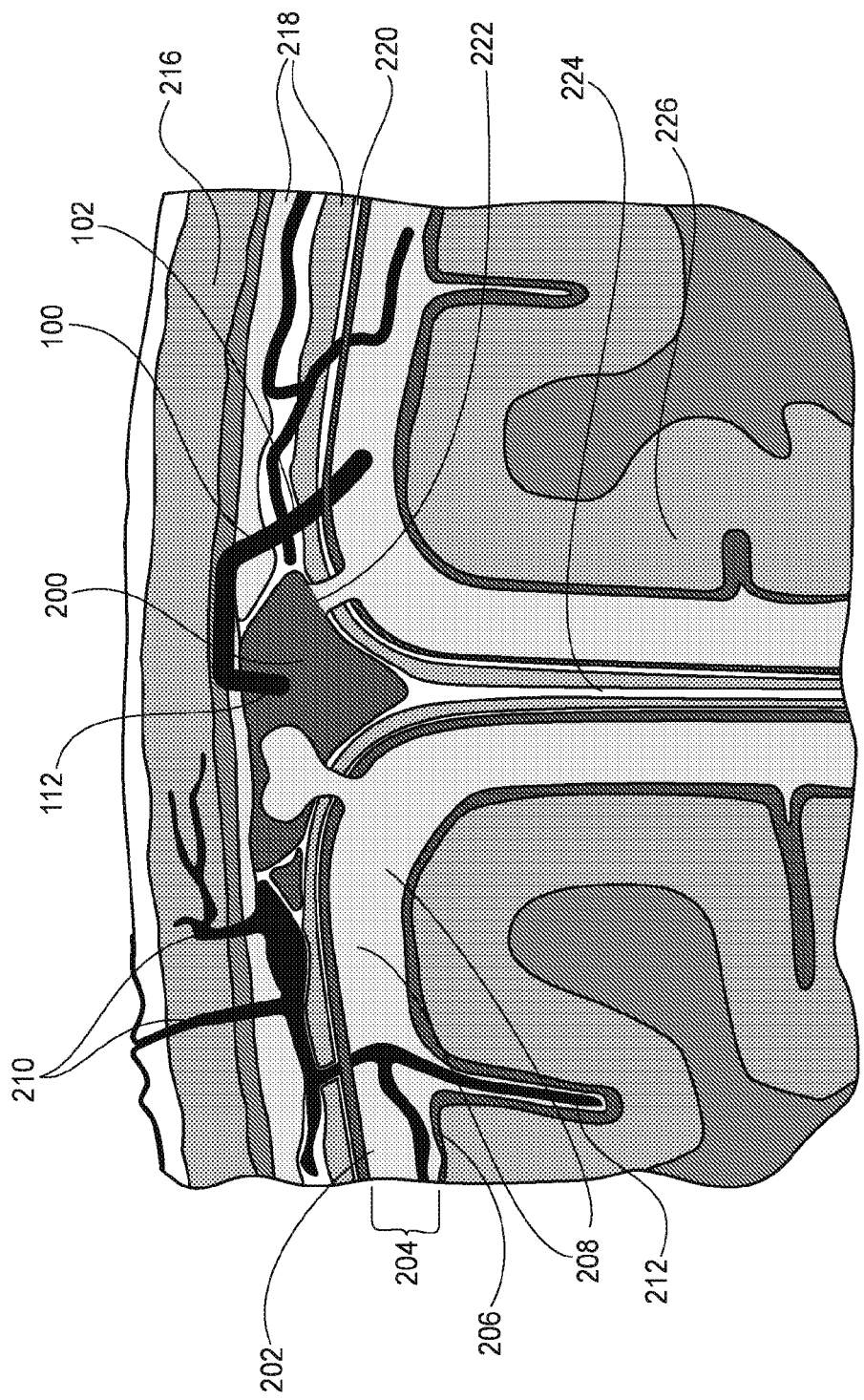
FIG. 33 depicts a view of an illustrative intracranial catheter in place in a subarachnoid space as seen in a coronal view of a subject's brain, according to one or more embodiments shown and described herein.

In some embodiments, a balloon may be used for obstruction of the blood flow when replacing the implantable device, specifically when the distal portion 2512 thereof is removed from the dural venous sinus (e.g., the sagittal sinus, the transverse sinus, and/or the like) for replacement or permanent replacement. FIGS. 31A and 31B depict an illustrative balloon 3140. More specifically, FIG. 31A depicts a single balloon 3140 that is placed around the circumference of the distal portion 2512 adjacent to the sinus wall 3303 (FIG. 33). The balloon 3140 may be placed adjacent to an exterior surface or an interior surface of the sinus wall 3303. When the balloon 3140 is inflated, it may compress the deformable region 2520 of the distal end 2512 such that fluid cannot flow therethrough. FIG. 31B depicts an alternative embodiment of the balloon 3140, wherein the balloon 3140 includes a first portion 3140a and a second portion 3140b. The first portion is placed around the distal portion 2512 adjacent to a first surface 3303a of the sinus wall 3303 and the second portion 3140b is placed around the distal portion 2512 adjacent to a second surface 3303b of the sinus wall 3303. The first and second portions 3140a, 3140b are then inflated to restrict fluid flow through the distal portion 2512 by compressing the deformable region 2520.

In operation, the implantable device 2500 is operable to cause drainage of various fluids, such as cerebrospinal fluid (CSF) for treatment of hydrocephalus. The implantable device 2500 may be inserted through a burr hole site such that the flat proximal portion is placed in a subarachnoid space and the distal portion of the catheter is placed in a venous sinus either with or against blood flow, thereby allowing the implantable device 2500 to drain fluid from the subarachnoid space into the venous sinus or transmit medication to the subarachnoid space and/or the venous sinus.

In some embodiments, it may be necessary to create the burr hole and place the implantable device 2500 in a particular location so as to ensure correct operation of the implantable device 2500, minimize injury to the subject, and/or the like. For example, the burr hole may be located in the frontal lobe or in the occipital lobe. Two illustrative locations, Location A and Location B of particular placement locations are depicted in FIGS. 32A-32C. The particular locations of Location A and Location B decrease a size and/or number of necessary incisions. As shown in FIGS. 32A and 32B, Location A may be at the axial center of the crown in the frontal lobe. As shown in FIGS. 32A and 32C, Location B may be in the occipital lobe region. It should be understood that Location A and Location B are merely illustrative, and other locations are contemplated.

FIG. 33 provides a more detailed view of insertion of the implantable device 2500 according to one or more embodiments. The various portions of a subject's intracranial area depicted in FIG. 33 include the superior sagittal sinus 3303, the arachnoid mater 3302, the subarachnoid space 3304, the pia mater 3306, the arachnoid trabeculae 3308, various veins 3310 including cerebral veins 3312, bone 106 (e.g., the skull), dura mater 3318, subdural space 3320, arachnoid granulation villi 3322, a longitudinal fissure 3324, and the cerebral cortex 3326.

As shown in FIG. 33, the implantable device 2500 is designed to slide over the surface of the brain and into the subarachnoid space 3304. The proximal portion 2502 of the implantable device 2500 is inserted into the subarachnoid space 3304 and the distal portion 2512 of the implantable device 2500 is inserted into the venous sinus of the brain (e.g., the superior sagittal sinus 3303) to allow drainage of the fluid (e.g., CSF) through the implantable device 2500 and into the blood system via the venous sinus.

Figure 34A:
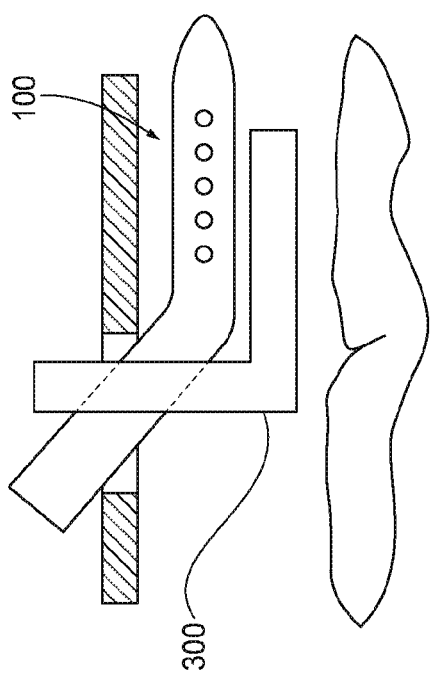
FIG. 34A depicts a side view of an illustrative tissue depressor that creates space for insertion of an intracranial catheter, according to one or more embodiments shown and described herein.
Figure 34C:
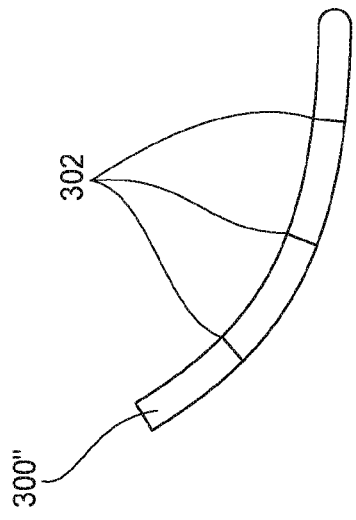
FIG. 34C depicts a side view of yet another illustrative tissue depressor, according to one or more embodiments shown or described herein.
Figure 34B:
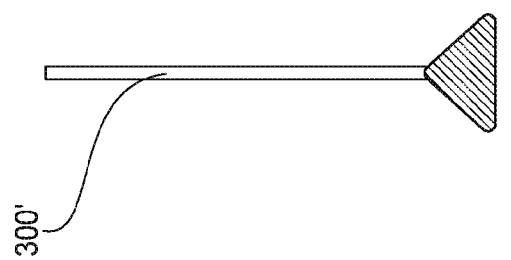
FIG. 34B depicts a side view of another illustrative tissue depressor, according to one or more embodiments shown or described herein.

In various embodiments, to ensure that the implantable device 2500 and/or a portion thereof is appropriately positioned (e.g., within the subarachnoid space 3304 and/or the superior sagittal sinus 3303 or other dural venous sinus) and/or prevent damage to tissue (e.g., the brain) when the implantable device 2500 is inserted, it may be necessary to compress tissue prior to insertion to create a space for the implantable device 2500 and/or a portion thereof. FIGS. 34A-34C depict illustrative examples of various tissue depressors 3400, 3400', 3400" (which may also be referred to as spatulas) that may be used to create such a space. As particularly indicated in FIG. 34A, a tissue depressor 3400 may be inserted into the target space (e.g., the subarachnoid space 3304) and may compress the tissue to create space for the implantable device 250. The implantable device 2500 is subsequently moved into position and the tissue depressor 3400 may then be removed. The tissue depressor 3400 depicted in FIG. 34A may be substantially L-shaped. However, it should be understood that the tissue depressor 3400 may have other shapes and/or sizes that may be more sufficient for compressing tissue and creating space for the implantable device, which may be based, for example, on the anatomy of the subject, the age of the subject, the location in which the implantable device 2500 is placed, and/or the like. For example, an alternative tissue depressor 3400' is depicted in FIG. 34B. The alternative tissue depressor 3400' may have a shape that differs from the L-shaped structure of the tissue depressor 3400 depicted in FIG. 34A (e.g., an inversely tapered shape). In another example, a third tissue depressor 3400" is depicted in FIG. 34C. The third tissue depressor 3400" may be curved. In some embodiments, any one of the various tissue depressors 3400, 3400', 3400" may have an offset angled handle to facilitate use. In some embodiments, any one of the various tissue depressors 3400, 3400', 3400" may have sidewalls that may be used to provide a guide for insertion of the implantable device 2500 so as to ensure the implantable device 2500 is accurately placed according to the sidewalls. In some embodiments, any one of the various tissue depressors 3400, 3400', 3400" may include one or more guide marks 3402 (FIG. 34C) thereon, where the guide marks 3402 correspond to a particular depth, location, and/or the like such that a user inserting the implantable device 2500 is guided to a particular depth, location, or the like via the guide marks 3402.

In addition to the various tissue depressors 3400, 3400', 3400", one or more other devices may also be used to assist in inserting the implantable device 2500. For example, a catheter introducer may be any device that can cannulate a venous channel and prevent the backflow of blood, air suction, and/or the like into the venous channel during insertion of the implantable device 2500. In some embodiments, such a catheter introducer may include one or more membranes that are particularly configured to prevent backflow of fluid. For example, a first membrane may have a permanent hole within and a second membrane may have a memory slit therein to allow the implantable device 2500 to be inserted.

In some embodiments, it may be necessary to abandon one or more portions of the implantable device 2500. As such, in addition to (or an alternative of) the plug 2832 (FIG. 28B), a chamber plug 3550 may be inserted. That is, the burr hole site (e.g., an opening 3502 in the bone 106) may receive the chamber plug 3550. The chamber plug 3550 may generally cover the burr hole site. The chamber plug 3550 may be used to prevent bone in-growth and allow for a mechanism to resonate the implantable device 2500 with radio frequency (RF), mechanical energy, and/or ultrasonic energy in order to control the flow within the implantable device 2500. For example, a transducer or an ultrasonic emitter 3552 may be attached to a bottom of the chamber plug 3550. The transducer or ultrasonic emitter 3552 may communicate with the resonant strips 2524 (FIG. 25B) located on the surface of the implantable device 2500 for resonation of the implantable device 2500. The ultrasonic emitter 3552 may also be used to image a morphology of the implantable device 2500 and determine if any obstruction is occurring at a particular location within the implantable device, such as, for example, the tip opening 2518 (FIG. 25A). The chamber plug 3550 may be constructed of one or more radiolucent and/or non-magnetic materials. A nonlimiting example of such a material may include polyether ether ketone (PEEK). Other materials are also contemplated.

Figure 35:
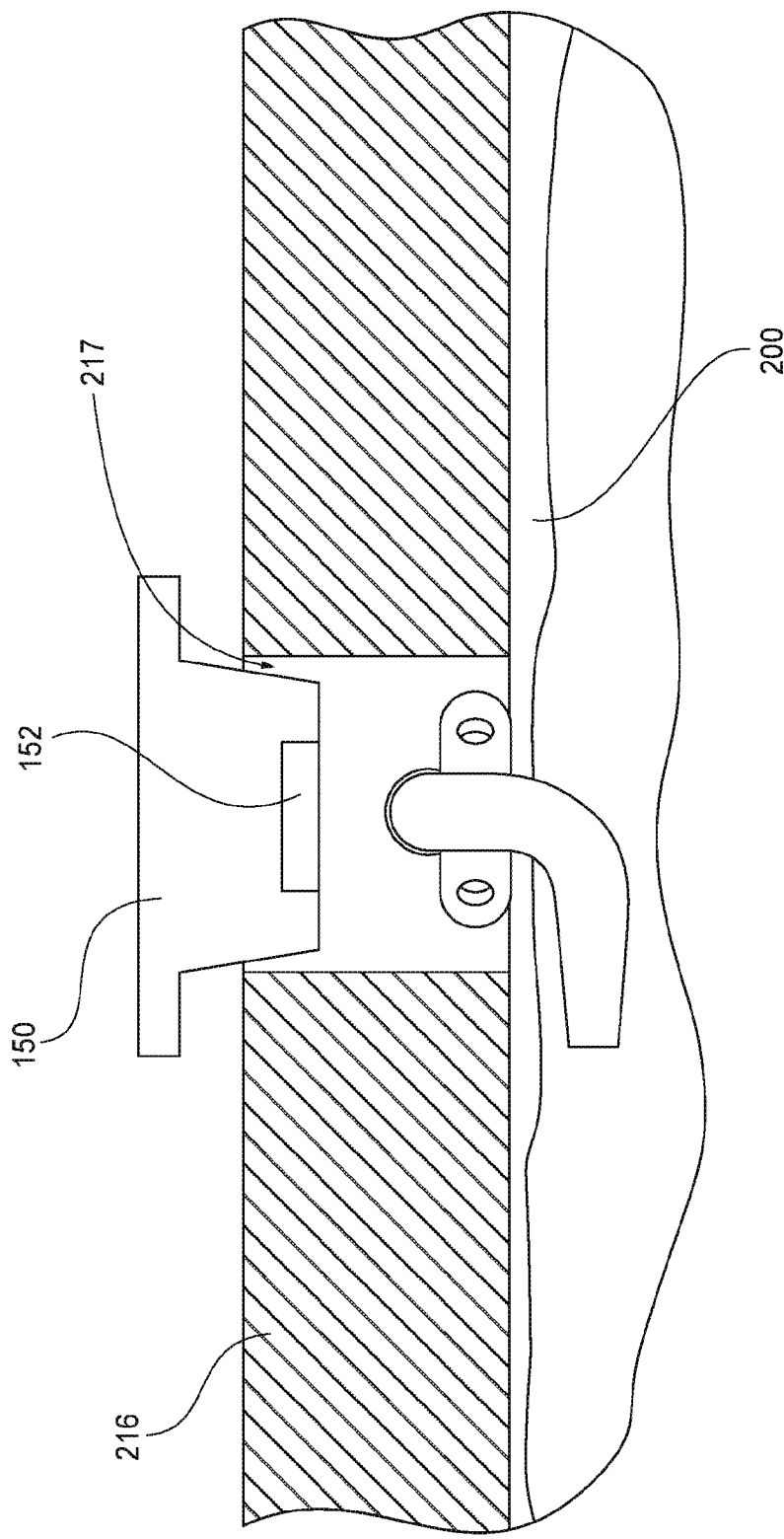
FIG. 35 depicts a cross-sectional side view of an illustrative burr hole site having an illustrative chamber plug that covers the burr hole site, according to one or more embodiments shown and described herein.

While not depicted in FIG. 35, the chamber plug 3550 may further be coupled to a transducer. The transducer may resonate the resonant strips 2524 on the implantable device 2500 for flow control or for imaging a morphology of the implantable device.

Figure 36:
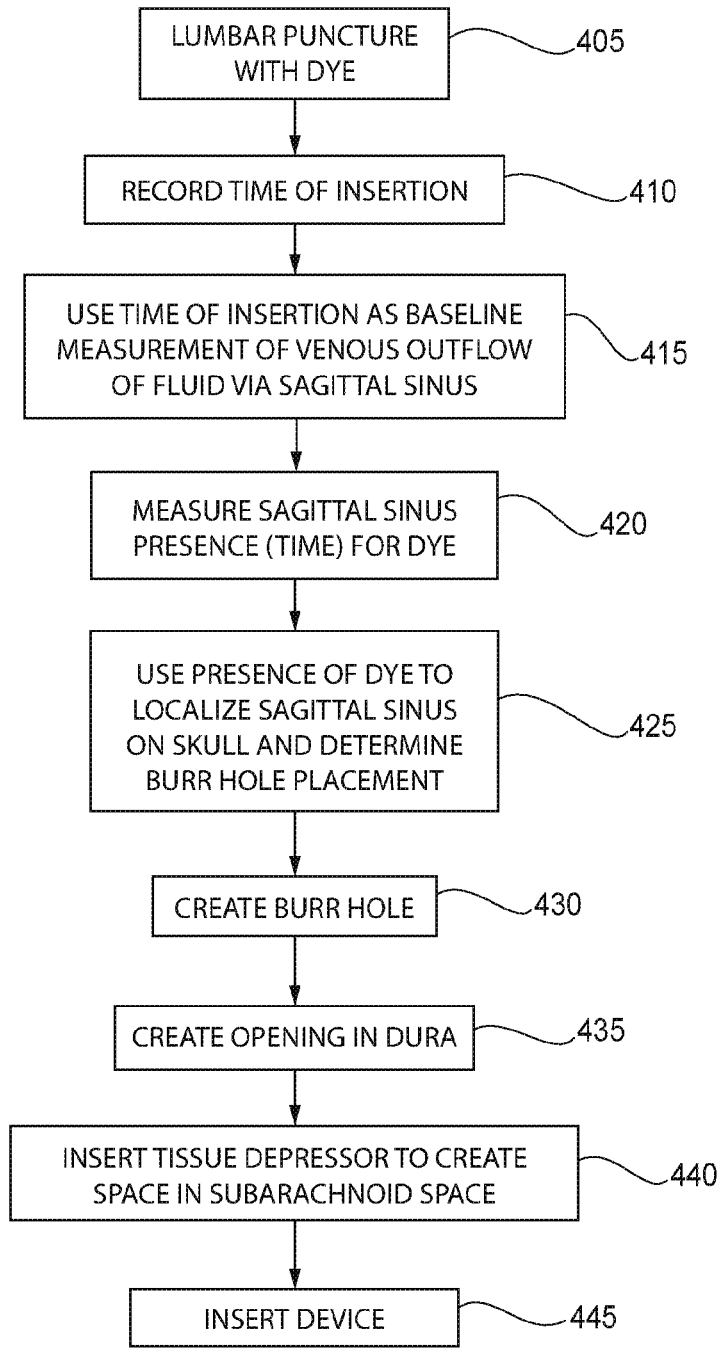
FIG. 36 depicts a flow diagram of an illustrative method of inserting an intracranial catheter, according to one or more embodiments shown and described herein.
Figure 37:
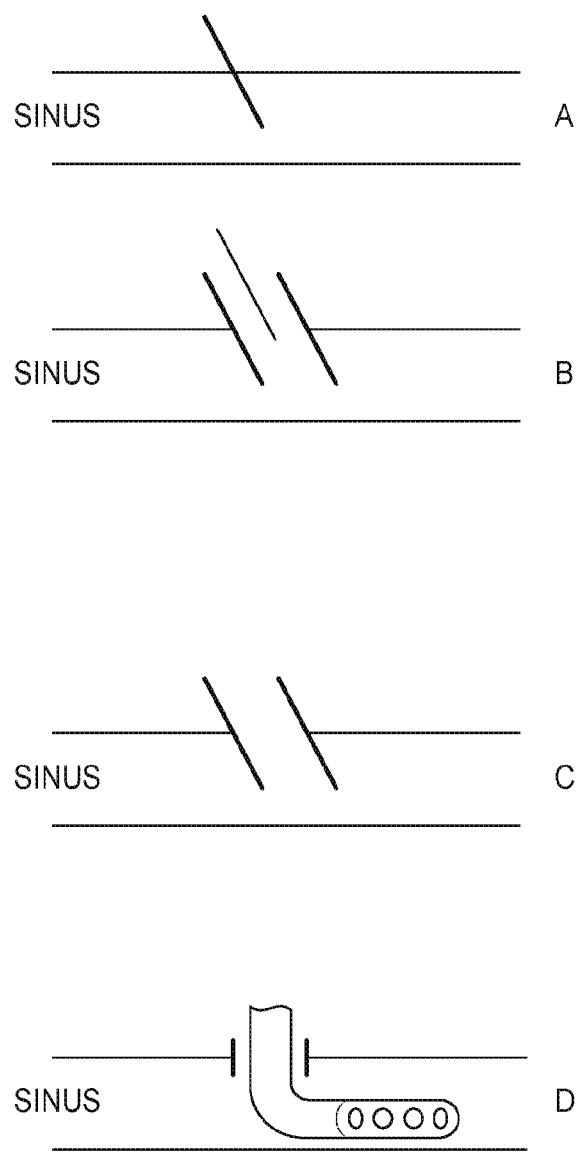
FIG. 37 depicts a side view of an illustrative method of inserting an intracranial catheter, according to one or more embodiments shown and described herein.

FIGS. 36 and 37 depict a method of inserting the implantable device 2500 according to various embodiments. For example, at step 3605, a lumbar puncture may be performed, as shown in part A of FIG. 37. Still referring to FIG. 36, in addition to the lumbar puncture, a radio-opaque, MRI contrast, or fluorescent dye may be injected. The dye may later be collected from a peripheral venous stick and tested for the function of the implantable device (e.g., to ensure the implantable device is appropriately placed). More specifically, at step 3610, the time the lumbar puncture is completed and the dye inserted is recorded and the recorded time is used as a baseline measurement of venous outflow of fluid via the dural venous sinus (e.g., the sagittal sinus, the transverse sinus, and/or the like) at step 3615. When dye is observed within the dural venous sinus, the time is measured at step 3620.

Further, utilizing x-ray, CT, Fluoroscopy, MRI, or other such imaging modalities, the presence of the dye is used to localize the dural venous sinus on the skull and determine an exact placement of a burr hole.

Once the placement is determined, the burr hole may be created at step 3630, as further indicated in part B of FIG. 37. Still referring to FIG. 36, this may generally be completed via any burr hole creation procedure now known or later developed. In some embodiments, creation of the burr hole may include creation of a linear incision of about 2 cm in length that is placed over the sinus. The burr hole may be, for example, an ellipsoid opening in the bone (coronal plane) that is sufficiently shaped and/or sized to receive the implantable device therein, as described herein. In addition to creating a burr hole, an opening in the dura may be created at step 3635. This may generally be completed via any dura opening procedure now known or later developed. The opening in the dura may also be shaped and/or sized to receive the implantable device 2500 therein, as described herein.

Part C of FIG. 37 shows an open space in the sinus for insertion of the implantable device 2500. However, if additional space is needed to insert the implantable device, the tissue depressor described herein may be inserted to create such a space in the subarachnoid space at step 3640 of FIG. 36. As such, a pressure may be applied to tissue to compress the tissue and create the necessary space. The implantable device 2500 may then be inserted at step 3645 and shown in part D of FIG. 37. Insertion of the implantable device 2500 may be assisted via ultrasound to isolate the sinus. In some embodiments, insertion of the implantable device 2500 may include creating a small slit in the adjacent dura to slide in the proximal portion 2502. The distal portion 2512 is connected to the central portion 2510, which is then secured to the proximal portion 2502. The distal catheter is then pushed into the dural venous sinus. A cover is then placed in the burr hole site. The wound is closed in a typical sterile fashion.

Insertion of the implantable device 2500 according to step 3645 may also be include passing a 22-25 solid gauge needle into the dural venous sinus, passing a dilator over the needle into the dural venous sinus while maintaining a tight internal seal around the needle and while producing both an internal and external flange seal to the dural venous sinus, withdrawing the needle with the internal seal maintaining control of any leakage of blood from the dural venous sinus, directionalizing the dilator such that its placement into the dural venous sinus is oriented in such a manner as to ensure proper orientation of the distal portion 2512 of the implantable device 2500 such that the tip opening thereof points into (against) the flow of venous blood. The dilator has an internal shape such that, when the distal portion 2512 of the implantable device 2500 is passed through the internal seal, it maintains a seal against any outward flow of blood while assuring that during implantable device 2500 insertion, the tip opening 2518 of the implantable device 2500 is pointed into the venous blood. In addition, the dilator may maintain a permanent elastic seal around the implantable device at all times. If replacement of the implantable device 2500 is ever required, the dilator will allow exchange of the original implantable device with a replacement without blood loss.

In some embodiments, insertion may further include use of an introducer device. The introducer device may cannulate the venous channel and prevent backflow of blood or air suction into the venous channel. The introducer device may further house two membranes inside the system. One membrane may have a permanent hole within and another membrane may have a memory slit to allow for device insertion.

In some embodiments, a bioseal or the like may be provided after insertion of the implantable device, so as to seal the dura and avoid leakage of fluid therefrom (e.g., CSF). Similarly, a bioseal adhesive may be used to seal the dural venous sinus from leaking fluid (e.g., blood).

Insertion of the device as described with respect to FIGS. 36 and 37 may allow the device to drain fluid as described herein and/or deliver medication to targeted areas as described herein. As such, the method may further include a step of draining the fluid from the subarachnoid space into the venous sinus, a transverse sinus, and/or a sigmoid sinus of the subject and/or delivering medication to the subarachnoid space, the venous sinus, a transverse sinus, and/or a sigmoid sinus of the subject.

It should be understood that other methods of inserting the implantable devices described herein are within the spirit and scope of the present disclosure. For example, implantable devices as described herein may be inserted utilizing guided navigation pre-surgery and/or post-surgery. As another example, anatomy landmark references may be used.

It should now be understood that the devices, systems, and methods described herein relate to implantable devices that are insertable into a subarachnoid space (SAS) and a dural venous sinus (DVS) of a subject. Systems including the implantable devices, when utilized as described herein, allow fluid, particularly CSF, to flow from the SAS into the DVS.

While particular embodiments and aspects of the present disclosure have been illustrated and described herein, various other changes and modifications can be made without departing from the spirit and scope of the disclosure. Moreover, although various aspects have been described herein, such aspects need not be utilized in combination. Accordingly, it is therefore intended that the appended claims cover all such changes and modifications that are within the scope of the embodiments shown and described herein.

Various aspects of the present disclosure are represented in the following enumerated clauses:

Clause 1: An instrument configured to exert positive control over dura displacement at all times during implantation.

Clause 2: The instrument of Clause 1, wherein positive control over dura displacement is realized via at least one of an adhesive, a surface tension, or a vacuum under a housing of the instrument such that the dura remains in direct contact with the housing and does not allow dura deflection during puncture.

Clause 3: An instrument configured to exhibit absolute control over depth of dura penetration, both subarachnoid space (SAS) and dural venous sinus (DVS).

Clause 4: An instrument configured to control displacement of the dura during cutting and/or insertion of the subarachnoid space (SAS) and dural venous sinus (DVS) portions.

Clause 5: The instrument of Clause 4, wherein controlled displacement of the dura during cutting and/or insertion is realized via at least one of a temporary vacuum, a temporary adhesive, or a very fine progressive puncture followed by upsized puncturing device.

Clause 6: A system including a needle and a sheath.

Clause 7: The system of Clause 6, wherein the system is a seldinger-like system.

Clause 8: A patch material configured to be glued to the dura to reinforce an area of puncture such that a tearing of the dura and/or a risk of subsequent bleeding and/or leakage of CSF is minimized.

Clause 9: The patch material of Clause 8, wherein the patch material is permanent or temporary.

Clause 10: The patch material of Clause 8, further comprising at least one of using a vacuum attaching instrument of Clause 5 with the patch material, using the patch material to provide suture attachment to instruments and/or a drainage apparatus, a "pursestring" device, reinforcing the patch material with an integral grommet, and wherein a geometry and/or size of the holes in the DVS and SAS are configured/designed to minimize tearing.

Clause 11: A system configured to interact with or attach to the bone to maintain position and control of a tube or a channel that allows for movement of CSF.

Clause 12: A system configured to serve as a channel or otherwise direct CSF from the SAS to the DVS when positioned above the dura.

Clause 13: A system including multiple openings or apertures or grommets in the dura to allow access to the SAS for CSF inflow.

Clause 14: The system of Clause 13, wherein the system is attached to a housing or channels or patch to direct CSF flow to the DVS.

Clause 15: A burr hole or template or router system configured for craniotomy that is circular but may also be oblong, squared, elliptical, or otherwise not circular.

Clause 16: A burr hole or template or router system configured to create two or more burr holes, wherein the burr holes do not overlap and define a removed bone-bridge between the burr holes or do overlap without defining a removed bone-bridge.

Clause 17: A burr hole or template or router system configured to guide a removal of a portion or all of a removed bone bridge.

Clause 18: An instrument configured to detect and to find locations appropriate for SAS and DVS access, and wherein the instrument is further configured to assist in creating access or directing instrumentation.

Clause 19: A system configured to detect and to find locations appropriate for SAS and DVS access, and wherein the system is further configured to assist in creating access or directing instrumentation.

Clause 20: An instrument designed to have positive positional control via an attachment to a cranium or an attachment to a location otherwise adjacent to a burr hole.

Clause 21: An instrument that centers an outlet in a lateral middle over a DVS, wherein a physical center of the instrument is equidistant to all walls of the DVS.

Clause 22: An instrument that centers an outlet in a correct orientation relative to venous blood flow.

Clause 23: An implant that is positionable within a constraining device that deploys within the DVS to ensure that an outlet is located in a physical center of the DVS, equidistant to all walls of the DVS, and to ensure a correct orientation relative to blood flow.

Clause 24: The implant of Clause 23, wherein the constraining device is an insertable, expandable cage, wherein the cage is configured to expand to the walls of the DVS.

Clause 25: A system comprising at least one of a patch, a housing, a grommet or a rigid device secured to a top of the DVS membrane to ensure that an outlet is located in a physical center of the DVS, equidistant to all walls of the DVS, and to ensure a correct orientation relative to blood flow.

Clause 26: A system including a variety of components that are varied and appropriately sized for at least one of subject size or variants in anatomy such as spatial relationship or depths of SAS and DVS.

Clause 27: A implant including an expandable ring grommet for creating a sealing connection to the dura, with an internal sealing membrane.

Clause 28: A implant including an expandable ring grommet for creating a sealing connection to the dura, without an internal sealing membrane.

Clause 29: An implant including a pigtail like tubing for security and directionality of DVS and SAS portions.

Clause 30: An implant including a mushroom like tubing for security and directionality of DVS and SAS portions.

Clause 31: A system including an integrated pump reservoir mechanism for at least one of purging, testing or cleaning all or a portion of the system.

Clause 32: The system of Clause 31, wherein the pump reservoir mechanism includes a soft walled manual pump for transferring fluids.

Clause 33: An implant comprising pulsed delivery of CSF to DVS to overcome a blockage.

Clause 34: A system including at least one of a channel, a housing, a grommet, a valve, and a catheter tip designed to provide a constant flow of CSF to prevent a blockage.

Clause 35: A system including at least one of an integrated inlet component or an integrated outlet component, with least one of the inlet component or the outlet component having a cover for purge access.

Clause 36: The system of Clause 35, wherein a housing or the cover is compliant and is designed to bulge, deform, or include deformable elements to allow tactile detection, instrument detection, sensor detection, or imaging detection of a function or a malfunction.

Clause 37: The system of Clause 35, wherein the cover is replaceable or includes components such that when the cover is replaced the system is effectively cleaned, maintained, or repaired.

Clause 38: The system of Clause 35, wherein a housing includes an element designed to inhibit bone growth and maintain a shape or patency of a burr hole.

Clause 39: The system of Clause 38, wherein the element includes a rigid perimeter.

Clause 40: The system of Clause 35, wherein a housing is constructed of sufficient dimensions to allow for bone growth or closure of a burr hole in a cranium.

Clause 41: The system of Clause 35, wherein the cover is designed to be rigidly secured to bone via screws.

Clause 42: The system of Clause 35, wherein the cover is designed to mechanically lock into another component(s) of an implant.

Clause 43: The system of Clause 35, whereon one or more housings are used.

Clause 44: A system including a modular implant, wherein components of the implant are replaceable for an exchange or interchange of components.

Clause 45: A system including an integrated housing configured for instrument access for at least one of testing, flushing or repair.

Clause 46: The system of Clause 45, wherein the instrument includes a needle.

Clause 47: A system including a housing sized, shaped and contouring to fit into and remain secure within a cranial burr hole.

Clause 48: The system of Clause 47, wherein the housing is shaped to aid in hemostatic or CSF leak control functions.

Clause 49: A system including an integrated housing designed to provide hemostatic seal of DVS and CSF leak control seal of SAS.

Clause 50: The system of Clause 49, wherein the housing includes at least one of integrated gaskets, valves, hemostatic agents, textures, surfaces, or porosity for tissue ingrowth which accomplishes to provide at least one of hemostatic seal of DVS and CSF leak control seal of SAS.

Clause 51: A system including a housing designed to be removable and replaceable in toto.

Clause 52: A system including at least one of an integrated housing, a fitting, a grommet, or a sealant to control at least one of length, position, or orientation of DVS.

Clause 53: A system including a housing having channels that at least one of directs or controls flow of CSF directionally or directs or controls flow in a manner that maintains patency or directs or controls flow to inhibits clogging or directs or controls flow to allow for an alternate path after clogging occurs.

Clause 54: The system of Clause 53, wherein the channels may also direct tubing or instrumentation.

Clause 55: The system of Clause 53, wherein a flow-control device may be incorporated or become activated as a flow in a channel changes.

Clause 56: A system including an integrated housing that provides a barrier above the dura to prevent accidental penetration by a needle or an instrument.

Clause 57: An implant that is designed to be indexable or positionable for antegrade flow or retrograde flow.

Clause 58: A system including an implant having components made of, or covered with at least one of bioresorbable materials or partially resorbable materials.

Clause 59: A system including at least one of guides, drills, lasers, tubes, valves, grommets, biologics, therapeutics and growth factors to create, allow for, or promote subject growth or development of channels and orifices, through native or created spaces, that allow CSF drainage into a vascular or other space.

Clause 60: An implant including a cranial plug that utilizes a channel, created in the cranium, to direct communication between the SAS and DVS and to drain CSF.

Clause 61: A system including a single or a plurality of burr holes to access the DVS and SAS and to individually connect them with an extra-cranial system, under the skin but over the bone.

Clause 62: A catheter comprising a tip including at least one of contours, openings, or valves to prevent thrombus formation.

Clause 63: A catheter tip that is double walled such that CSF is capable of flowing in a hollow area between the walls.

Clause 64: A system including at least one of an integrated housing, a fitting, a grommet, a gasket, or a plug, the system, when placed through a burr hole and into the SAS, providing atraumatic retraction of the brain to facilitate a constant opening to CSF.

Clause 65: A system, including a set of modular functional components, that when implanted and connected to form an assembly, drain excess CSF from a subarachnoid space to a dural sinus without having any of the modular functional components penetrating the gray matter of the brain.

Clause 66: A system, including a set of modular functional components, that when implanted and connected to form an assembly, allow for post-surgical access for servicing at least one of the modular functional components individually or the modular functional components in any combination, without penetrating the gray matter of the brain.

Clause 67: A set of implants as shown and described herein.

Clause 68: An instrument as shown and described herein.

Clause 69: A surgical method as shown and described herein.

The invention claimed is:

1. A subarachnoid space (SAS) implant plug, comprising: a generally cylindrical body having a top and a bottom, the body comprising an aperture, wherein the cylindrical body is dimensioned to interferingly fit substantially within a burr hole drilled in a subject's skull, and wherein the aperture is defined through a height of the generally cylindrical body from the bottom to the top; wherein the generally cylindrical body is defined by a first portion at the top that corresponds to a first burr hole portion, a second portion that corresponds to a second burr hole portion, and a third portion at the bottom that corresponds to a third burr hole portion, and wherein the third portion had a diameter less than a diameter of the first portion and the second portion tapers between the first portion and the third portion to control an insertion depth of the SAS implant plug; and further comprising cerebrospinal fluid inlet drains at the bottom, the drains being in fluid communication with the aperture.

2. The SAS implant plug of claim 1, wherein the drains extend beyond the third portion of the cylindrical body.

3. The SAS implant plug of claim 1, wherein the drains are disposed around a perimeter of the third portion of the cylindrical body.

4. The SAS implant plug according to claim 1, wherein the aperture comprises a membrane seal.

5. The SAS implant plug according to claim 1, wherein the aperture is defined by a diameter configured to accommodate a drain implant.

6. The SAS implant plug according to claim 1, wherein the aperture extends centrally through the generally cylindrical body.

7. The SAS implant plug according to claim 1, further comprising a generally elongate drain implant having a proximal portion at the generally cylindrical body and extending from the generally cylindrical body to a distal portion so as to form a SAS implant drain plug assembly, the distal portion of the drain implant having a plurality of cerebrospinal fluid inlet drains in fluid communication with the aperture.

8. The SAS implant plug according to claim 7, wherein the proximal portion of the drain implant plugs into the aperture.

9. The SAS implant plug according to claim 8, wherein the distal portion comprises a planar surface configured for insertion through a burr hole between the dura and the brain of a subject.

10. The SAS implant plug according to claim 9, wherein the planar surface is configured to depress the brain a predetermined amount from the dura to permit cerebrospinal fluid to flow into the drains.

11. The SAS implant plug according to claim 9, wherein the planar surface extends distally a predetermined distance to access cerebrospinal fluid.

12. The SAS implant plug according to claim 1, wherein the aperture comprises a membrane seal, an implant body having an aperture and distal inlet drain sections.

* * * * *